(12) United States Patent
Labrecque et al.

(10) Patent No.: US 6,274,620 B1
(45) Date of Patent: Aug. 14, 2001

(54) THIOPHENE INTEGRIN INHIBITORS

(75) Inventors: Denis Labrecque; Giorgio Attardo, both of Laval; Monica Bubenik, Montreal; Laval Chan, Kirkland; Sylvie Charron, Montreal; Réal Denis; Guy Falardeau, both of Laval; Serge Lamothe, Boisbriand; Patrice Préville, Blainville; Boulos Zacharie, Laval, all of (CA)

(73) Assignee: BioChem Pharma Inc., Laval (CA)

( * ) Notice: Subject to any disclaimer, the term of this patent is extended or adjusted under 35 U.S.C. 154(b) by 0 days.

(21) Appl. No.: 09/588,574

(22) Filed: Jun. 7, 2000

Related U.S. Application Data

(60) Provisional application No. 60/137,726, filed on Jun. 7, 1999.

(51) Int. Cl.[7] .......................... A61K 31/38; A61K 31/34; A61K 31/40; C07D 333/22; C07D 401/00
(52) U.S. Cl. .......................... 514/448; 514/471; 514/275; 514/423; 549/72; 549/487; 544/331; 548/537
(58) Field of Search .................................. 514/448, 471, 514/275, 241, 423; 549/72, 487; 544/331, 180; 548/537

(56) References Cited

U.S. PATENT DOCUMENTS

| | | | |
|---|---|---|---|
| 5,786,373 | * | 7/1998 | Hartman et al. ............... 514/326 |
| 6,040,311 | * | 3/2000 | Duggan et al. ................. 514/275 |

FOREIGN PATENT DOCUMENTS

| | | |
|---|---|---|
| 94/08577 | 4/1994 | (WO) . |
| WO 94/08577 | 4/1994 | (WO) . |
| WO 96/37492 | 11/1996 | (WO) . |
| 97/37655 | 10/1997 | (WO) . |
| WO 98/18461 | 5/1998 | (WO) . |
| WO 98/31359 | 7/1998 | (WO) . |
| WO 98/34935 | 8/1998 | (WO) . |
| WO99/59992 | * 11/1999 | (WO) . |
| 00/00486 | 1/2000 | (WO) . |

OTHER PUBLICATIONS

Vascular Indications for Integrin αv Antagonists, Currrent Pharmaceutical Design, 1997 vol. 3, No. 6 James Samanen et al. (40 pages).

Discovery of Potent Isoxazoline Glycoprotein lib/llla Receptor Antagonists, J. Med. Chem. 1997, 40 50–60; John Wityak et al. (6 pages).

* cited by examiner

Primary Examiner—Deborah C. Lambkin
(74) Attorney, Agent, or Firm—Arent Fox Kintner Plotkin & Kahn PLLC

(57) ABSTRACT

The present invention comprises compounds that are effective inhibitors of integrins, particularly αvβ3 and αvβ5 integrins. Particularly, the compounds are of formula I

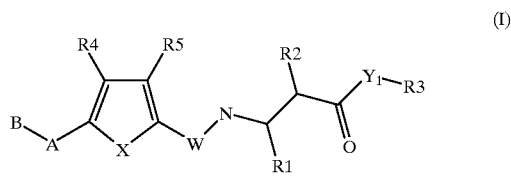

(I)

and pharmaceutically acceptable salts thereof wherein X, $Y_1$ W, R1 to R5, A and B are defined according to the disclosure herein.

38 Claims, No Drawings

THIOPHENE INTEGRIN INHIBITORS

CROSS REFERENCE TO RELATED APPLICATION

This application claims the benefit of provisional application 60/137,726 filed Jun. 7, 1999, the contents of which are fully incorporated by reference, herein.

BACKGROUND OF THE INVENTION

1. Field of the Invention

The present invention relates to compounds that inhibit certain integrins, particularly to compounds that inhibit $\alpha_v$ integrins.

2. Description of the Background Art

Integrins are a major family of adhesion receptors. They are produced by most cell types and are a means by which the cell senses its immediate environment and responds to changes in extracellular matrix (ECM) composition. ECM is composed of structural and regulatory molecules, some of which include laminin, collagen, vitronectin and fibronectin, as well as a variety of proteoglycans. These molecules, in cooperation with cell surface receptors, not only provide the basis for structural support, but also contribute to the transmission of biochemical signals from the ECM to the cells interior. Thus, integrins are cell adhesion receptors capable of mediating cell-extracellular matrix and cell-cell interactions. Integrins are implicated in the regulation of cellular adhesion, migration, invasion, proliferation, angiogenesis, osteoclast bone resorption, apoptosis and gene expression (P. C. Brooks, DN&P, 10(8), 456–61, 1997).

The integrin family is composed of 15 $\alpha$ and 8 $\beta$ subunits that are contained in over twenty different $\alpha\beta$ heterodimeric combinations on cell surfaces. Each heterodimers have distinct cellular and adhesive specificities. Integrins bind to extracellular matrix proteins or cell surface molecules through short peptides sequences present in the ligands. Although some integrins selectively recognize a single extracellular matrix protein ligand, other bind to two or more ligands. Several integrins recognize the tripeptide Arg-Gly-Asp (RGD), whereas others recognize alternative short peptide sequences. Combinations of different integrins on cell surfaces allow cells to recognize and respond to a variety of different extracellular matrix proteins (J. A. Varner and D. A. Cheresh, Curr. Opin. Cell Biol., 8, 724–30, 1996).

The $\alpha_v$-series integrins are a major subfamily of integrins. As well as classically mediating cell attachment and spreading, $\alpha_v$ integrins are implicated in cell locomotion, in ligand-receptor internalization, as virus co-receptors, in management of the extracellular protease cascades and as regulators of tumor progression, angiogenesis and apoptosis. The specificities of the five known $\alpha_v$-integrins, $\alpha_v\beta_1$, $\alpha_v\beta_3$, $\alpha_v\beta_5$, $\alpha_v\beta_6$ and $\alpha_v\beta_8$ have been defined and they exclusively recognize ligands via the tripeptide sequence RGD, including vitronectin ($\alpha_v\beta_1$, $\alpha_v\beta_3$, $\alpha_v\beta_5$), fibronectin ($\alpha_v\beta_1$, $\alpha_v\beta_5$, $\alpha_v\beta_6$), von Willibrand factor ($\alpha_v\beta_3$), fibrinogen ($\alpha_v\beta_3$) and osteopontin ($\alpha_v\beta_3$) (F. Mitjans, J. Cell. Science, 108, 2825–38, 1995).

In disease, adhesive function is frequently compromised and results in tissue disorder, aberrant cell migration and dysregulation of signaling pathways. It is well known that alterations in the composition and integrity of the ECM can significantly influence cellular behavior, which in turn may have an impact on a number of pathological processes such as tumor neovascularization, restenosis, arthritis, and tumor growth and metastasis. Thus, inhibiting the function of molecules that regulate these cellular events may have significant therapeutic benefit (P. C. Brooks, DN&P, 10(8), 456–61, 1997).

There are at least three major classes of reagents currently being developed as integrin antogonists, and these include antibodies (monoclonal, polyclonal and synthetic) and small synthetic peptides (synthetic cyclic RGD peptides), as well as a family of snake venom-derived proteins termed "disintegrins". The third major group of antagonists includes non-peptide mimetics and organic-type compounds.

Integrin $\alpha_v\beta_3$, the most promiscuous member of the integrin family, mediates cellular adhesion to vitronecin, fibronectin, fibrinogen, laminin, collagen, von Willibrand factor, osteopontin and adenovirus penton base. Expression of this integrin enables a given cell to adhere to, migrate on, or respond to almost any matrix protein it may encounter.

Integrins of the $\alpha_v$ subfamily are implicated in tumor development. Integrin $\alpha_v\beta_3$ is minimally, if at all expressed on resting, or normal, blood vessels, but is significantly upregulated on vascular cells within human tumors. In particular, both vertical progression of the primary melanoma and distant metastases are characterized histologically by an increased expression of $\alpha_v\beta_3$ integrin (B. Felding-Habermann et al., J. Clin. Invest., 89, 2018–22, 1992). A study involving human malignant melanoma, an increasingly prevalent and aggressive skin cancer, reported the use of monoclonal antibodies to block the $\alpha_v$ integrin-ligand interaction which resulted in severely disrupting the development of the tumor (F. Mitjans et al., J. Cell Sci., 108, 2825–38, 1995).

Another important physiological role played by integrin $\alpha_v\beta_3$ in cancer is within the process of angiogenesis. Angiogenesis, the formation of new blood vessels, allows the cancer to spread and grow. It was shown that blood vessels involved in angiogenesis have enhanced expression of $\alpha_v\beta_3$ (P. C. Brooks et al., Science, 264, 569–571, 1994; C. J. Drake et al., J. Cell Sci., 108, 2655–61, 1995). It was also shown that preventing the $\alpha_v\beta_3$ integrin from binding to their ligands caused apoptosis (programmed cell death) in the endothelial cells of newly formed blood vessels and inhibited neovascularization (P. C. Brooks et al., Cell, 79, 1157–64, 1994; M. Christofidou-Solomidou et al., Am. J. Pathol., 151(40), 975–83, 1997; J. Luna, Lab. Invest., 75(4), 563–73, 1996). Thus, antagonists of integrin $\alpha_v\beta_3$ may provide a powerful therapeutic approach for the treatment of neoplasia or other diseases characterized by angiogenesis.

Another pathological process which involves $\alpha_v\beta_3$ is coronary restenosis. Surgical trauma and/or injury to blood vessels may lead to the stimulation of smooth muscle cells resulting in an increase migration and proliferation of these cells, which causes an occlusion in the vessel wall and prevents blood flow. Following arterial injury, it was shown that there was early upregulation of integrin $\alpha_v\beta_3$ at sites of cell accumulation within the vessel wall and that selective blockade of $\alpha_v\beta_3$ was an effective anti-restenotic strategy (S. S. Srivatsa et al., Cardiovascul. Res., 36, 408–28, 1997).

$\alpha_v$ integrins are especially interesting targets since they are implicated in many metabolic processes, such as angiogenesis, bone resorption, and cellular migration and proliferation. Consequently, antagonists of $\alpha_v$ integrins have great therapeutic potential for diseases such as rheumatoid arthritis, psoriasis, eye diseases (diabetic retinopathy and macular degeneration), restenosis, neointimal hyperplasia, osteoporosis and more particularly against tumors, since they simultaneously strike at the developing tumor and at its blood supply (U.S. Pat. No. 5843906-WO 9736859/GD Searle & Co; EP 854140/Hoechst AG; WO 9733887-WO9637492/Du Pont Merck Pharm Co; WO 9844797-WO 9831359-WO 9818461-WO 9744333-WO 9737655-WO 9532710-WO 9408577).

There is thus a constant need to find other antagonists of $\alpha_v$ integrins in order to provide additional modes of treatments for many diseases that still have no cure. The present invention satisfies this and other need.

SUMMARY OF THE INVENTION

The present invention provides novel compounds that are effective inhibitors of integrins, particularly $\alpha_v$ integrins such as $\alpha_v\beta_3$ and $\alpha_v\beta_5$. Particularly, the compounds of the present invention are represented by formula I:

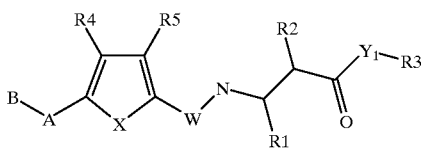

(I)

and pharmaceutically acceptable salts thereof, wherein:

X is selected from the group consisting of O and S;

$Y_1$ is selected from the group consisting of O, S and N;

W is selected from the group consisting of carbonyl and sulfonyl; R1 and R2 are independently selected from the group consisting of H, $C_{5-10}$aryl, $C_{5-10}$arylsulfonylamino, $C_{5-10}$cycloalkylsulfonylamino, $C_{5-10}$arylamino and $C_{5-10}$aryl$C_{1-6}$alkyl with the proviso that R1 and R2 are not both H; R3 is selected from the group consisting of H, halogen, $C_{1-18}$alkyl, $C_{1-18}$alkylamino $C_{0-18}$alkyl, $C_{1-18}$hydroxyalkyl, $C_{1-18}$alkylether, $C_{1-18}$alkylthioether, $C_{1-18}$alkyl-$Y_2$C(O)$Y_3$—$C_{0-18}$alkyl, $C_{1-18}$alkyl-C(O)$Y_3$—$C_{0-18}$alkyl, $C_{1-18}$alkyl-$Y_2$C(O)—$C_{0-18}$alkyl, $C_{5-12}$aryl, $C_{5-12}$aryl$C_{0-18}$alkyl-$Y_2$C(O)$Y_3$—$C_{0-18}$alkyl, $C_{1-18}$alkyl$C_{5-12}$aryl, and $C_{5-12}$aryl$C_{1-18}$alkyl, wherein $Y_2$ and $Y_3$ are independently O, S or N, —C(O) $C_{1-18}$alkenyl, $C_{0-18}$alkyl-$C_{3-12}$cycloalkyl, $C_{1-18}$haloalkyl, and $C_{1-18}$alkynyl;

R4 and R5 are independently selected from the group consisting of H, halogen, $C_{1-6}$alkyl and $C_{1-6}$alkoxy;

A is selected from the group consisting of $C_{1-6}$alkyl, $C_{2-6}$alkenyl, $C_{2-6}$alkynyl, $C_{5-10}$aryl and $C_{3-10}$cycloalkyl; and B is selected from the group consisting of amino, $C_{1-6}$aminoalkyl, $C_{5-10}$arylamino, guanidino, $C_{1-6}$guanidinoalkyl, cyclic guanidino, urea and cyclic urea.

Other embodiments of the present invention include specific compounds and general formulas disclosed in the detailed description below.

Another aspect of the invention is a process for preparing compounds of formula I or pharmaceutically acceptable salts thereof. The method comprises preparing the compounds according to anyone of the Schemes or processes disclosed in the detailed description below.

Another aspect of the present invention includes a method for treating cancer comprising administering a pharmaceutically effective amount of the compound of formula I or a pharmaceutically acceptable salt thereof to a mammal. Other embodiments of the invention include methods of treatment as set forth in the detailed description.

Yet another aspect of the present invention includes a method for treating solid tumors comprising administering a pharmaceutically effective amount of the compound of formula I or a pharmaceutically acceptable salt thereof to a mammal.

Yet another aspect of the present invention includes a method for treating osteoporosis comprising administering a pharmaceutically effective amount of the compound of formula I or a pharmaceutically acceptable salt thereof to a mammal.

Yet another aspect of the present invention includes a method for treating restenosis comprising administering a pharmaceutically effective amount of the compound of formula I or a pharmaceutically acceptable salt thereof to a mammal.

Yet another aspect of the present invention includes a method for treating ocular diseases in which abnormal neovascularization occurs comprising administering a pharmaceutically effective amount of the compound of formula I or a pharmaceutically acceptable salt thereof to a mammal.

Yet another aspect of the present invention includes a method for inhibiting an $\alpha_v$ integrin in vivo comprising administering a pharmaceutically effective amount of the compound of formula I or a pharmaceutically acceptable salt thereof to a mammal.

These and other features and advantages of the present invention will become apparent from the following detailed description of the invention which illustrate by way of example the principles of the invention.

DETAILED DESCRIPTION OF THE INVENTION

The present invention comprises compounds that are effective inhibitors of integrins including $\alpha_v$ integrins, as well as effective medicaments for the inhibition of angiogenesis and thereby useful for treating cancer. Other therapeutic applications include treating osteoporosis, restenosis, ocular neovascularization or any other disease in which antagonism of αv integrins would result into therapeutic benefit.

Particularly, the compounds are of formula I

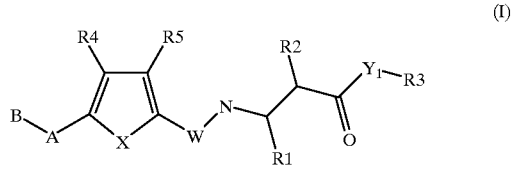

(I)

and pharmaceutically acceptable salts thereof wherein X, Y, W, R1, R2, R3, R4, R5, A and B are as previously defined.

In one embodiment, X is S.

In another embodiment, $Y_1$ is —NH—.

In another embodiment, $Y_1$ is —O—.

In another embodiment, $Y_1$ is —S—.

In another embodiment, R1 is represented by the formula N—$Y_4$—R6 wherein $Y_4$ is selected from the group consisting of —$CO_2$—, —$SO_2$— and —$(CH_2)_{0-2}$—; R6 is selected from the group consisting of:

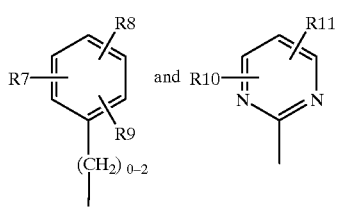

wherein R7, R8, R9, R10, R11 are independently selected from the group consisting of H, $C_{1-6}$alkyl, $C_{1-6}$alkoxy and halogen. In this embodiment, R2 is preferably H.

In another embodiment, R2 is represented by the formula N—$Y_4$—R6 wherein $Y_4$ is selected from the group consisting of —$CO_2$—, —$SO_2$— and —$(CH_2)_{0-2}$—; R6 is selected from the group consisting of:

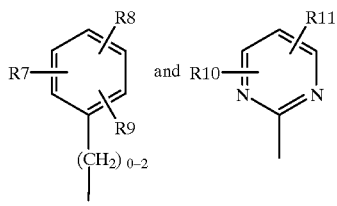

wherein R7, R8, R9, R10, R11 are independently selected from the group consisting of H, $C_{1-6}$alkyl, $C_{1-6}$alkoxy and halogen. In this embodiment, R1 is preferably H.

In yet another embodiment, R1 is H and R2 is $C_{5-10}$arylsulfonylamino.

In yet another embodiment, R1 is H and R2 is selected from the group consisting of phenylsulfonylamino and trimethylphenylsulfonylamino.

In yet another embodiment, R1 is H and R2 is $C_{5-10}$aralkyl.

In yet another embodiment, R1 is H and R2 is benzyloxycarbonyl.

In yet another embodiment, R1 is H and R2 is $C_{5-10}$arylamino.

In yet another embodiment, R1 is H and R2 is pyrimidinylamino.

R3 is selected from the group consisting of H, halogen, $C_{1-18}$alkyl, $C_{1-18}$alkylamino $C_{0-18}$alkyl, $C_{1-18}$hydroxyalkyl, $C_{1-18}$alkylether, $C_{1-18}$alkylthioether, $C_{1-18}$alkyl-$Y_2$C(O)$Y_3$—$C_{0-18}$alkyl, $C_{1-18}$alkyl-C(O)$Y_3$—$C_{0-18}$alkyl, $C_{1-18}$alkyl-$Y_2$C(O)—$C_{0-18}$alkyl, $C_{5-12}$aryl, $C_{5-12}$aryl$C_{0-18}$alkyl-$Y_2$C(O)$Y_3$—$C_{0-18}$alkyl, $C_{1-18}$alkyl$C_{5-12}$aryl, $C_{5-12}$aryl $C_{1-18}$alkyl, —C(O) $C_{1-18}$alkenyl, $C_{0-18}$alkyl-$C_{3-12}$cycloalkyl, $C_{1-18}$haloalkyl, and $C_{1-18}$alkynyl, wherein $Y_2$ and $Y_3$ are independently O, S or N.

In another embodiment, R3 is selected from the group consisting of H, halogen, $C_{1-10}$alkyl, $C_{1-10}$alkylamino $C_{0-10}$alkyl, $C_{1-10}$hydroxyalkyl, $C_{1-10}$alkylether, $C_{1-10}$alkylthioether, $C_{1-10}$alkyl-$Y_2$C(O)$Y_3$—$C_{0-10}$alkyl, $C_{1-10}$alkyl-C(O)$Y_3$—$C_{0-10}$alkyl, $C_{1-10}$alkyl-$Y_2$C(O)-$C_{0-10}$alkyl, $C_{5-12}$aryl, $C_{5-12}$aryl$C_{0-10}$alkyl-$Y_2$C(O)$Y_3$—$C_{0-10}$alkyl, $C_{1-10}$alkyl $C_{5-12}$aryl, $C_{5-12}$aryl$C_{1-18}$alkyl, —C(O)$C_{1-10}$alkenyl, $C_{0-10}$alkyl-$C_{3-12}$ cycloalkyl, $C_{1-18}$haloalkyl, and $C_{1-10}$alkynyl, wherein $Y_2$ and $Y_3$ are independently O, S or N, wherein $Y_2$ and $Y_3$ are independently O, S or N.

In another embodiment, R3 is selected from the group consisting of H, halogen, $C_{1-18}$alkyl, $C_{1-18}$alkylamino $C_{0-18}$alkyl, $C_{1-18}$hydroxyalkyl, $C_{1-18}$alkylether, $C_{1-18}$alkyl-C(O)$Y_3$—$C_{0-18}$alkyl, $C_{1-18}$ alkyl-$Y_2$C(O)-$C_{0-18}$alkyl, $C_{5-12}$aryl, $C_{1-18}$alkyl$C_{5-12}$aryl, $C_{5-12}$aryl $C_{1-18}$alkyl, —C(O) $C_{1-18}$alkenyl, $C_{0-18}$alkyl-$C_{3-12}$cycloalkyl, and $C_{1-18}$haloalkyl, wherein $Y_2$ and $Y_3$ are independently O, S or N.

In another embodiment, R3 is selected from the group consisting of H, $C_{1-18}$alkyl, $C_{1-18}$alkylamino $C_{0-18}$alkyl, $C_{1-18}$hydroxyalkyl, $C_{1-18}$alkylether, $C_{5-12}$aryl, $C_{1-18}$alkyl$C_{5-12}$aryl, and $C_{5-12}$aryl$C_{1-18}$alkyl.

In another embodiment, R3 is selected from the group consisting of H, $C_{1-18}$alkyl, $C_{1-18}$alkylamino $C_{0-18}$alkyl, $C_{1-18}$hydroxyalkyl, and $C_{1-18}$alkylether.

In another embodiment, R3 is $C_{1-18}$alkyl.

In another embodiment, R3 is selected from the group consisting of $C_{1-18}$alkyl-$Y_2$C(O)$Y_3$—$C_{0-18}$alkyl, $C_{1-18}$alkyl-C(O)$Y_3$—$C_{0-18}$ alkyl, $C_{1-18}$alkyl-$Y_2$C(O)$C_{0-18}$alkyl, $C_{5-12}$aryl$C_{0-18}$alkyl-$Y_2$C(O)$Y_3$—$C_{0-18}$ alkyl, wherein $Y_2$ and $Y_3$ are independently O, S or N.

In another embodiment, $Y_1$ is —NH— and R3 is $C_{1-18}$alkyl.

In another embodiment, $Y_1$ is —O— and R3 is $C_{1-18}$alkyl.

In another embodiment, R3 is H.

In another embodiment, R3 is selected from the group consisting of $C_{5-12}$aryl, $C_{1-18}$alkyl$C_{5-12}$aryl, and $C_{5-12}$aryl$C_{1-18}$alkyl.

In another embodiment, R4 and R5 are H.

In another embodiment, W is carbonyl.

In another embodiment, A is $C_{1-6}$alkyl.

In yet another embodiment, A is —$(CH_2)_{2-4}$—.

In yet another embodiment, A is —$(CH_2)_3$—.

In another embodiment, A is $C_{2-6}$alkenyl.

In yet another embodiment, A is —$(CH_2)_{0-2}$—C=C—$(CH_2)_{0-2}$—.

In yet another embodiment, A is —CH=CH—$CH_2$—.

In yet another embodiment, A is —$CH_2$—CH=CH—.

In another embodiment, A is $C_{2-6}$alkynyl.

In yet another embodiment, A is —$(CH_2)_{0-2}$—C≡C—$(CH_2)_{0-2}$—.

In yet another embodiment, A is —C≡C—$CH_2$—.

In yet another embodiment, A is —$CH_2$—C≡C—.

In another embodiment, A is —$C_{0-2}$alkyl-$C_{5-10}$aryl-$C_{0-2}$alkyl- wherein the aryl does not contain heteroatoms.

In another embodiment, A is —$C_{0-2}$alkyl-$C_{5-10}$aryl-$C_{0-2}$alkyl- wherein the aryl contains heteroatoms.

In yet another embodiment, A is selected from the group consisting of:

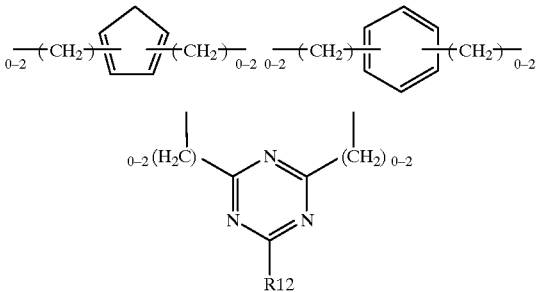

wherein $R_{12}$ is selected from the group consisting of H, $C_{1-6}$alkyl, $C_{1-6}$alkoxy and $NH_2$.

In yet another embodiment, A is

wherein $R_{12}$ is selected from the group consisting of H, $C_{1-6}$alkyl, $C_{1-6}$alkoxy and $NH_2$.

In yet another embodiment, A is

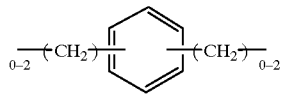

wherein $R_{12}$ is selected from the group consisting of H, $C_{1-6}$ alkyl, $C_{1-6}$alkoxy and $NH_2$.

In yet another embodiment, A is selected from the group consisting of:

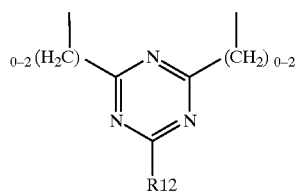

wherein $R_{12}$ is selected from the group consisting of H, $C_{1-6}$alkyl, $C_{1-6}$alkoxy and $NH_2$.

In yet another embodiment, A is selected from the group consisting of:

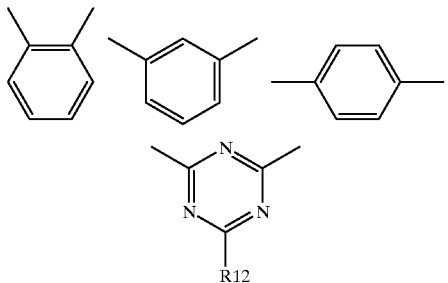

wherein $R_{12}$ is selected from the group consisting of H and $NH_2$.

In yet another embodiment, A is

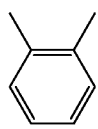

In yet another embodiment, A is

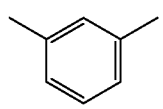

In yet another embodiment, A is

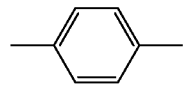

In yet another embodiment, A is

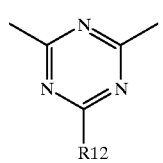

wherein $R_{12}$ is selected from the group consisting of H and $NH_2$.

In another embodiment, B is selected from the group consisting of guanidino and $C_{1-6}$guanidinoalkyl.

In another embodiment, B is selected from the group consisting of amino, $C_{1-6}$aminoalkyl, $C_{5-10}$arylamino.

Particular compounds according to the present invention include the following:

Compound B-3

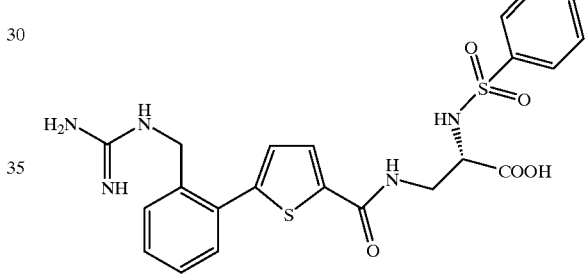

Compound C-3

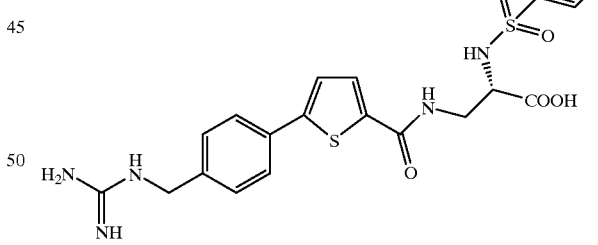

Compound C-4

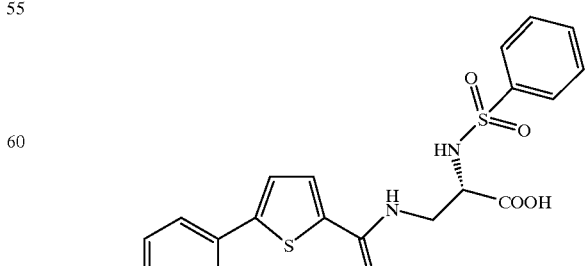

Compound E-2
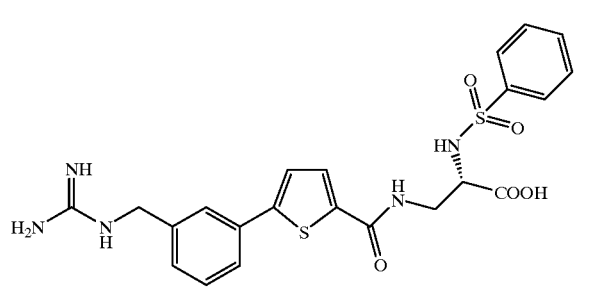
Compound K-3
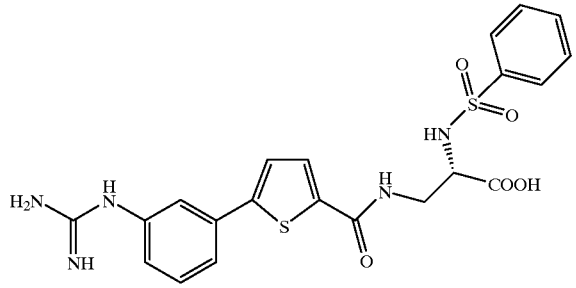
Compound F-2
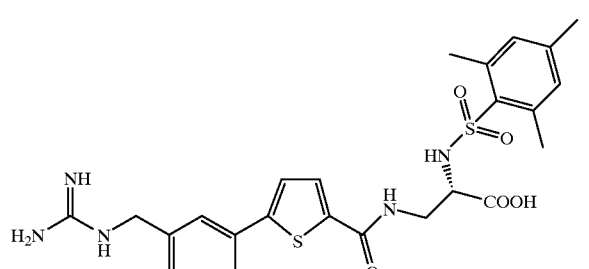
Compound L-3
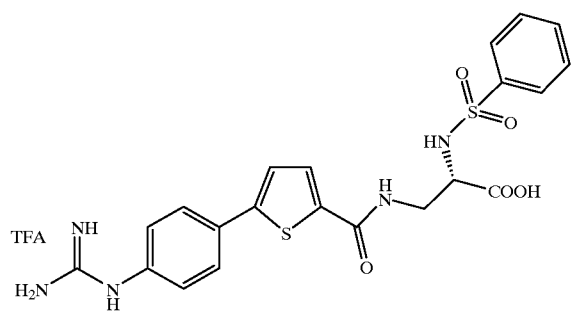
Compound H-3
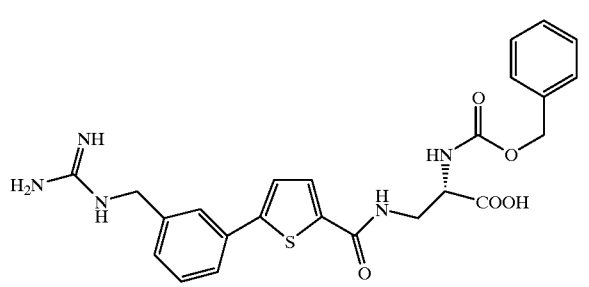
Compound M-3
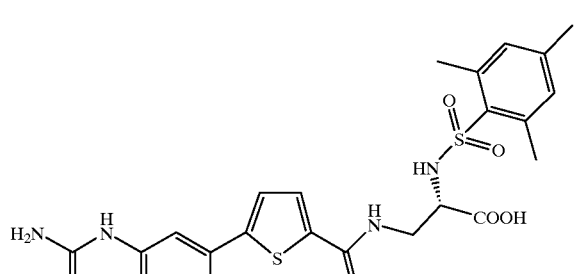
Compound I-3
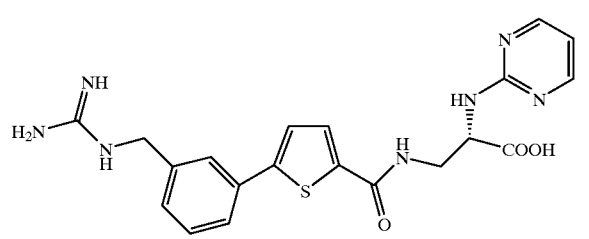
Compound O-6
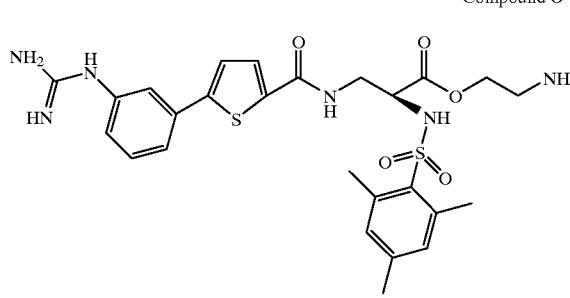
Compound J-3
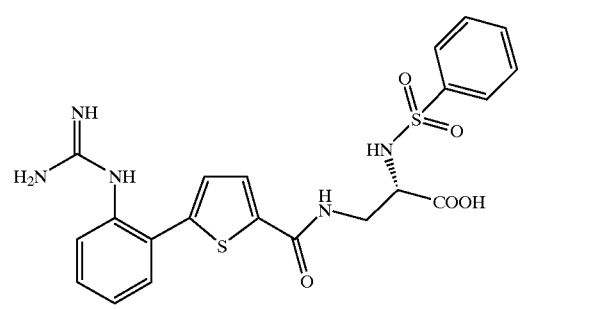
Compound P-5
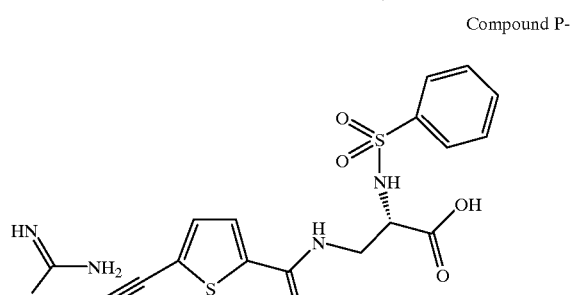

Compound P-8
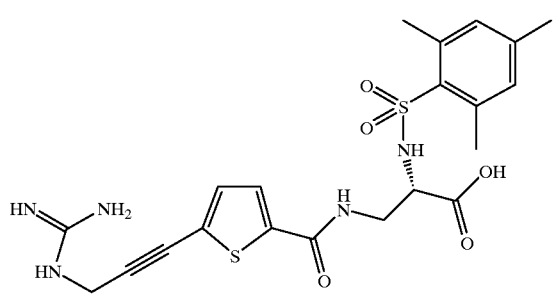
Compound Q-2
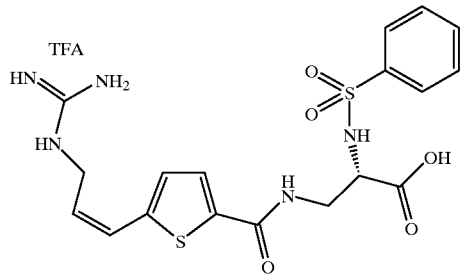
Compound R-2
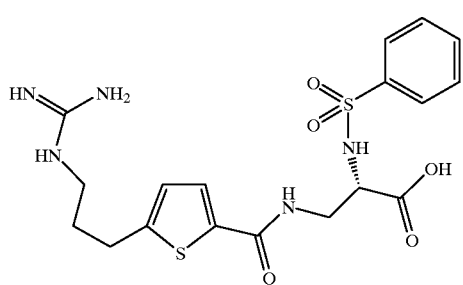
Compound S-3
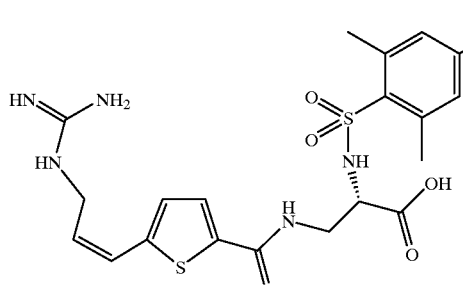
Compound S-4
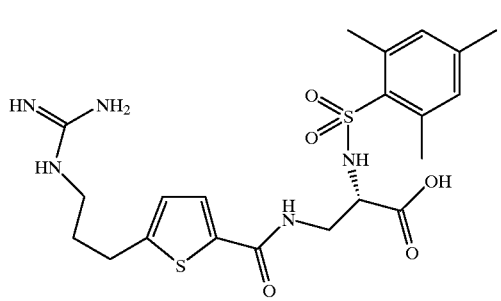
Compound T-10
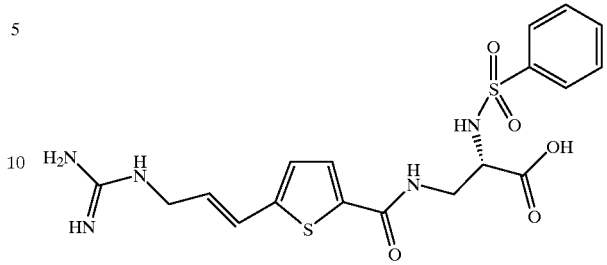
Compound T11
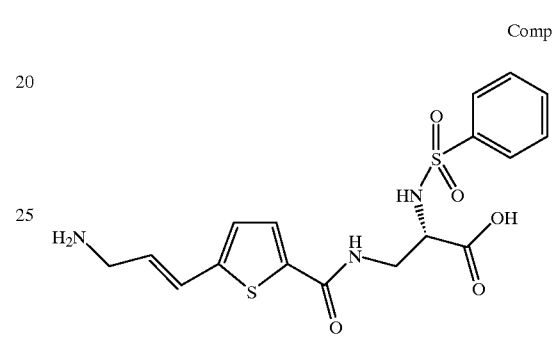
Compound U-2
Compound V-4
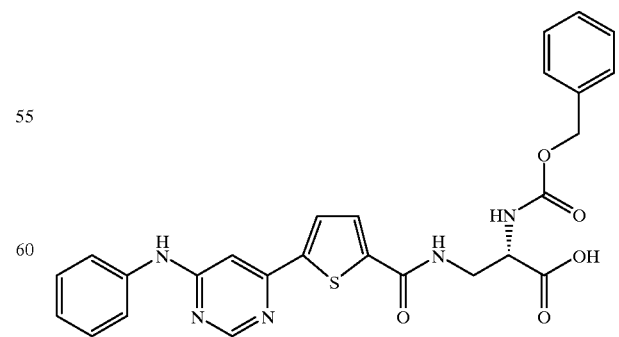

Compound W-4

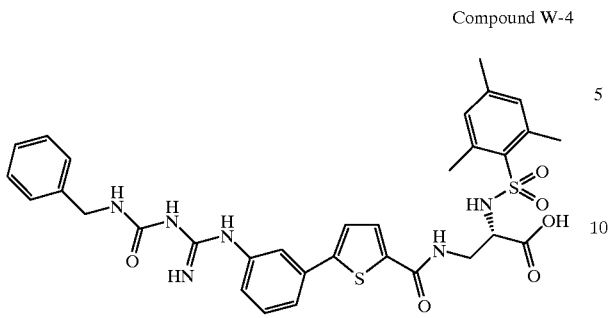

There is also provided pharmaceutically acceptable salts of the present invention. By the term pharmaceutically acceptable salts of compounds of general formula (I) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, trifluoroacetic, toluene-p-sulphonic, tartaric, acetic, citric, methanesulphonic, formic, benzoic, malonic, naphthalene-2-sulphonic and benzenesulphonic acids. Other acids such as oxalic, while not pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4+$ (where R is $C_{1-4}$alkyl) salts.

References hereinafter to a compound in certain embodiments of the invention includes compounds of the general formula (I) and their pharmaceutically acceptable salts.

As used in this application, the term "alkyl" represents an unsubstituted or substituted (by a halogen such as fluoro, alkenyl or alkynyl) straight or branched chain having a specified total number of carbon atoms.

The terms "alkenyl" and "alkynyl" represent an alkyl containing at least one unsaturated group (e.g. allyl).

The term "amino" includes primary amines i.e. $NH_2$, secondary amines i.e. NHR, or tertiary amines i.e. NRR, wherein R is an alkyl. Also encompassed by the term are quaternary amines such as $—NH_3^+$ or $—NR'_3^+$ wherein each R' is independently H or alkyl.

The term "aminoalkyl" refers to an alkyl group, wherein the alkyl group is covalently bonded to an adjacent element through a nitrogen atom(e.g., $—NCH_3$).

The term "alkoxy" refers to an alkyl group, wherein the alkyl group is covalently bonded to an adjacent element through an oxygen atom (e.g., methoxy and ethoxy).

The term "guanidino" refers to the following structure:

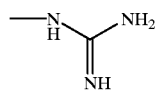

The term "guanidinoalkyl" refers to a guanidino group, wherein the guanidino group is covalently bonded to an adjacent element through an alkyl.

The term "cyclic guanidino" refers to the following structure:

wherein Q is an alkyl.
The term "urea" refers to the following structure:

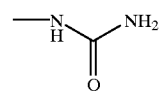

The term "cyclic urea" refers to the following structure:

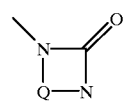

wherein Q is an alkyl.

The term "aryl" refers to an unsaturated carbocyclic moiety which is optionally interrupted with one or more heteroatoms selected from the group consisting of O, N, or S and which is optionally substituted by a halogen, nitro, $CONH_2$, alkyl, alkoxy, hydroxyl, amino, or COOQ, wherein Q is H or alkyl.

The term "carboaryl" refers to an unsaturated carbocyclic moiety which is optionally substituted by a halogen, nitro, $CONH_2$, alkyl, alkoxy, hydroxyl, amino, or COOQ, wherein Q is H or alkyl.

The term "heteroaryl" refers to an unsaturated carbocyclic moiety which is substituted with one or more heteroatoms selected from the group consisting of O, N, or S and which is optionally substituted by a halogen, nitro, $CONH_2$, alkyl, alkoxy, hydroxyl, amino, or COOQ wherein Q is H or alkyl.

The term "cycloalkyl" or "cyclic alkyl" refers to a saturated carbocyclic moiety which is optionally interrupted with one or more heteroatoms selected from the group consisting of O, N, or S and which is optionally substituted by a halogen, $CONH_2$, alkyl, alkoxy, hydroxyl, amino, or COOQ, wherein Q is H or alkyl.

The term "aralkyl" or "aryl alkyl" refers to an aryl group, wherein the aryl group is covalently bonded to an adjacent element through an alkyl.

The term "arylsulfonyl" refers to an aryl group, wherein the aryl group is covalently bonded to an adjacent element through a sulfonyl(e.g. $—SO_2—$).

The term "cycloalkylsulfonyl" refers to a cycloalkyl group, wherein the cycloalkyl group is covalently bonded to an adjacent element through a sulfonyl(e.g. $—SO_2—$).

The term "arylamino" refers to an aryl group, wherein the aryl group is covalently bonded to an adjacent element through a nitrogen atom.

The term "pyrimidinyl" represents a six member aryl that contains two nitrogen atoms separated by carbon.

The present invention also includes methods of making compounds of formula I or any of the other formulas disclosed herein. Compounds of the present invention can be synthesized using conventional preparative steps and recovery methods known to those skilled in the art of organic chemistry. A synthetic route according to one embodiment of the invention is illustrated in Scheme 1 and described as follows. As used herein, functional groups R1–R5, X, W and B are as previously defined.

Scheme 1

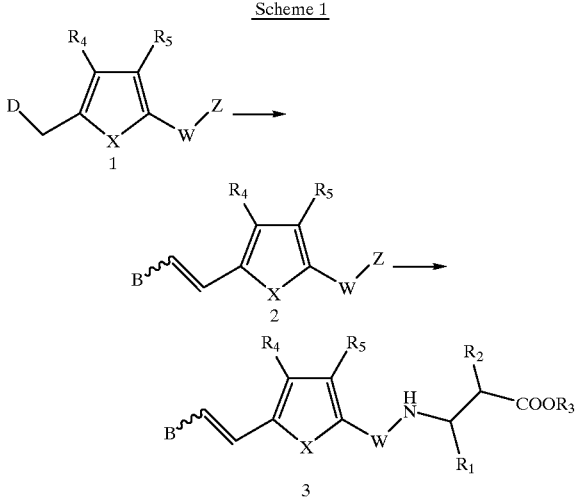

According to Scheme 1, Wittig reagent 1 (wherein D is a triarylphosphonium salt or phosphonate and Z is selected from the group consisting of halogen or hydroxy) is prepared from the corresponding 5-(halo-methyl)-substituted thiophene or furan derivative. Wittig, Wittig-Horner or Horner-Hemmons coupling reactions are carried out between reagent 1 and an appropriate aldehyde providing alkene 2. For example, reaction of chloroacetaldehyde with deprotonated 1 in tetrahydrofurane provides a chloromethylvinylthiophene 2 which is further reacted with a protected amino compound providing a protected aminomethylvinylthiophene 2 in good yield. Derivative 2 is coupled to a suitably functionalized 3-aminopropionic acid using standard peptidic coupling procedure providing vinylic thiophene 3.

Another synthetic route according to one embodiment of the invention is illustrated in Scheme 2 and described as follows. As used herein, functional groups R1–R5, X, W, Z and B are as previously defined.

Scheme 2

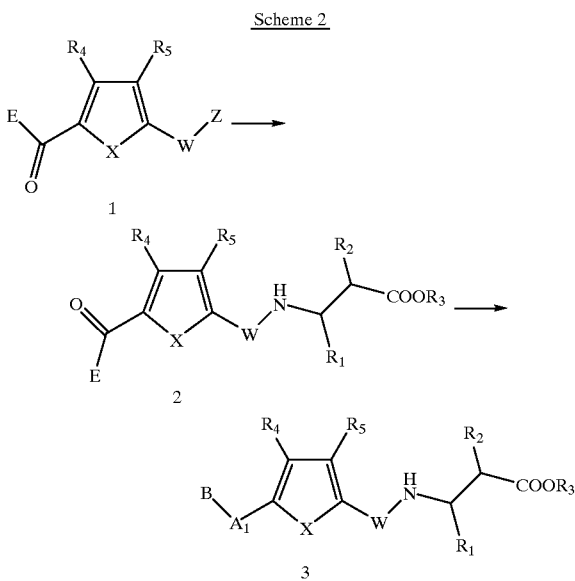

According to Scheme 2, 5-(carbonyl)-substituted thiophene or furan derivative 1 (wherein E is selected from the group consisting of N,O,H or halide) is coupled to a suitably protected 3-amino propionic acid using standard peptidic coupling procedures to provide the precursor thiophene 2 which is in turn modified in ways related to the work of Goddard (Goddard, Carl J., 5-Heteroaryl-2-thiophenecarboxylic acids: oxazoles and oxadiazoles., J. Heterocycl. Chem., (1991), 28(1), 17–28) or Kelarev (Kelarev V. I., Koshelev V. N., Morozova G. V., Karakhanov R. A., Remizov A. S., Khim Geterotsikl Soedin [KGSSAQ], 1995, (2), 214–223) or Furukawa (Hayashi S., Furukawa M., Fujino Y., Morishita H., Chem Pharm Bull [CPBTAL], 1971, 19, 1789) providing a heterobicyclic compound 3 (wherein A1 is an aryl form of A as herein defined). For example, carboxylic acid 2 (wherein E is OH) was coupled with phenyl-bisguanidine using standard peptidic coupling procedure and provided thienotriazine 3.

Another synthetic route according to one embodiment of the invention is illustrated in Scheme 3 and described as follows. As used herein, functional groups R1–R5, X, W, Z, A and B are as previously defined

Scheme 3

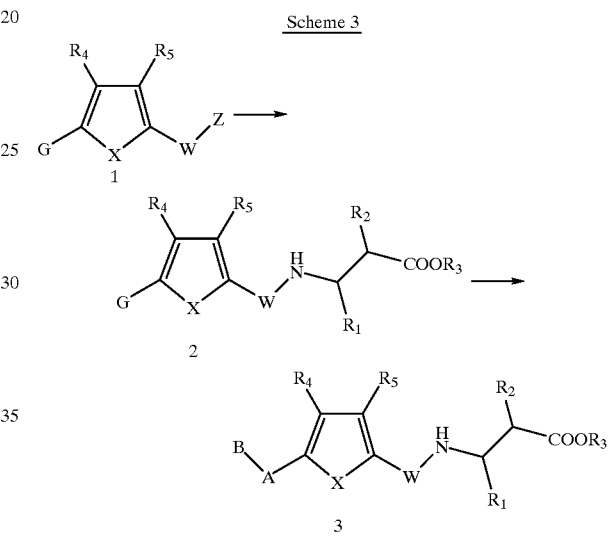

5-Halo-substituted thiophene or furan derivative 1 (wherein G is halogen) was coupled with a suitably functionalized 3-aminopropionic acid to give amide 2. Palladium cross coupling using either the methods developed by Stille (Stille J. K., Angew. Chem., 1986, 98, 504–519) or Suzuki (Miyaura N., Suzuki A., Chem. Rev., 1995, 95, 2457–2483) or Heck (Heck R. F., Palladium Reagents in Organic Syntheses, 1985, Academic Press) were then carried to link the aryl, alkenyl or alkynyl moiety to the thiophene or furan moiety. For example, reaction of a phenylboronic acid in the presence of a palladium catalyst under basic conditions gave the desired phenyl thiophene 3 in good yield. Where appropriate, the product was then converted into a suitably functionalized derivative. For example, cross coupling of an alkyne with compound 1 gave an alkynyl-thiophene derivative 3 which upon hydrogenation in the presence of a catalyst gave an alkenyl or alkyl derivative.

It will be appreciated by those skilled in the art that the compounds of formula I, depending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

One embodiment of the present invention comprises a method of inhibiting integrins using a compound of formula I or any other compound or formula disclosed herein.

Another embodiment of the present invention comprises a method of inhibiting $\alpha_v$ integrins using a compound of formula I or any other compound or formula disclosed herein.

Another embodiment of the present invention comprises a method of inhibiting $\alpha_v\beta_3$ integrin using a compound of formula I or any other compound or formula disclosed herein.

In yet another embodiment of the present invention comprises a method of inhibiting $\alpha_v\beta_5$ integrin using a compound of formula I or any other compound or formula disclosed herein.

Another embodiment of the present invention comprises a method for inhibiting angiogenesis using a compound of formula I or any other compound or formula disclosed herein.

Another embodiment of the present invention comprises a method for preventing a cell from binding to osteopontin using a compound of formula I or any other compound or formula disclosed herein.

Another embodiment of the present invention comprises a method for preventing a cell from binding to fibronectin, vitronectin, fibrinogen or any other ligand to $\alpha_v\beta_3$ and $\alpha_v\beta_5$ integrins using a compound of formula I or any other compound or formula disclosed herein.

Another embodiment of the present invention comprises a method for treating a tumor using a compound of formula I or any other compound or formula disclosed herein. In another aspect of this invention, the tumor is a solid tumor.

Another embodiment of the present invention comprises a method for treating cancer using a compound of formula I or any other compound or formula disclosed herein.

Another embodiment of the present invention comprises a method for treating foot and mouth disease using a compound of formula 1 or any other compound or formula disclosed herein.

Another embodiment of the present invention comprises a method for treating osteoporosis, restenosis, ocular neovascularization, or any other diseases in which $\alpha_v$ integrins are implicated, using a compound of formula I or any other compound or formula disclosed herein.

One embodiment of the present invention also provides compositions which comprise a pharmaceutically acceptable carrier or adjuvant and an effective amount of a compound of formula I to inhibit in a mammal angiogenesis, tumor growth, osteoporosis, restenosis, ocular neovascularization and/or any disease in which $\alpha_v$ integrins are implicated. The proportion of each carrier, diluent or adjuvant is determined by the solubility and chemical nature of the compound and the route of administration according to standard pharmaceutical practice.

Therapeutic and prophylactic methods of this embodiment of the invention comprise the step of treating patients in a pharmaceutically acceptable manner with those compounds or compositions. Such compositions may be in the form of tablets, capsules, caplets, powders, transdermal patches, granules, lozenges, suppositories, reconstitutable powders, or liquid preparations, such as oral or sterile parenteral solutions or suspensions.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrrolidone; fillers, such as lactose, sugar, maize-starch, calcium phosphate, sorbitol or glycine; tableting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. The amount of active ingredient administered parenterally will be approximately 0.01 to 250 mg/kg/day, preferably about 0.05 to 10 mg/kg/day, more preferably about 0.5 to 30 mg/kg/day, and more most preferably about 1–20 mg/kg/day.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound.

The solid oral compositions may be prepared by conventional methods of blending, filling, tableting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate of sorbic acid; and, if desired, conventional flavoring or coloring agents.

For parenteral administration, fluid unit dosage forms may be prepared by utilizing the compound of the present invention and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the peptide should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical composition of this invention comprise a compound of formula I and a pharmaceutically acceptable carrier, diluent or adjuvant. Typically, they contain from about 1% to about 99% by weight of active compound, and preferably from about 10% to about 60% by weight depending on which method of administration is employed.

Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on disease stage, the weight of the patient, the relative efficacy of the compound and the judgment of the treating physician. Such therapy may extend for several weeks or months, in an intermittent or uninterrupted manner.

To further assist in understanding the present invention, the following non-limiting examples are provided.

EXAMPLES

Example 1

Synthesis of the Compounds

2-Benzenesulfonylamino-3-[(5-bromo-thiophene-2-carbonyl)-amino]-propionic acid -tert-butyl ester (A-1)

A mixture of 5-bromothiophene-2-carboxylic acid (3.1 g, 15 mmol), 2-benzenesulfonylamino-2-tert-butoxycarbonyl-ethyl-ammonium chloride (4.58 g, 13.6 mmol), 1-[3-(dimethylamino)propyl]-3-ethylcarbodiimide hydrochloride (2.87 g, 15 mmol), 1-hydroxybenzotriazole (2.01 g, 15 mmol) and 4-methylmorpholine (3 mL, 27.3 mmol) in dry dimethylformamide (DMF, 36 mL) was stirred at room temperature for 16 h. The DMF was removed and the mixture was dissolved in ethyl acetate (400 mL), washed with water (25 mL), saturated NaCl solution (25 mL), 5% $KHSO_4$ (25 mL), saturated NaCl solution (25 mL) and saturated $NaHCO_3$-saturated NaCl mixture (1:1) (25 mL), dried and evaporated. The crude was passed through a column of silica gel with $CH_2Cl_2$-acetone (95:5 and 90:10) as eluents yielding 6 g of compound A-1(90% yield).

$^1$HNMR (400 MHz, $CD_3OD$) δ: 1.26 (s, 9H), 3.47 (dd, J=7.7, 13.5 Hz, 1H), 3.64 (dd, J=6.2, 13.5 Hz, 1H), 4.11 (dd, J=6.2, 7.6 Hz, 1H), 7.16 (d, J=4.0 Hz, 1H), 7.41 (d, J=4.0 Hz, 1H), 7.48–7.58 (m, 3H), 7.84–7.86 (m, 2H).

3-[(5-Bromo-thiophene-2-carbonyl)-amino]-2-(2,4,6-trimethylbenzenesulfonyl amino)-propionic acid tert-butyl ester (A-2)

4-methylmorpholine (3.6 mL, 32.7 mmol) was added to a mixture of 5-bromothiophene-2-carboxylic acid (3.6 g; 17.4 mmol), 2-tert-butoxycarbonyl-2-(2,4,6-trimethyl-benzenesulfonylamino)-ethyl-ammonium chloride (6.0 g; 15.85 mmol), 1-[3-(dimethylamino)propyl]-3-ethylcarbodiimide hydrochloride (3.34 g; 17.4 mmol) and 1-hydroxybenzotriazole (2.35 g; 17.4 mmol) in dry DMF (45 mL). The mixture was stirred at room temperature for 16 h. DMF was removed and the crude mixture was dissolved in ethyl acetate (400 mL). The solution was washed with water (25 mL), saturated NaCl (25 mL), 5% $KHSO_4$ (25 mL), saturated NaCl (25 mL), saturated $NaHCO_3$-saturated NaCl mixture (1:1) (25 mL), dried and evaporated. The crude was passed through a column of silica gel and the column was eluted with hexane-EtOAc mixtures (10% to 30% EtOAc) yielding 7.9 g of compound A-2 containing trace amount of ethyl acetate (90% yield).

$^1$H NMR (400 MHz, $CD_3OD$) δ: 1.28 (s, 9H), 2.24 (s, 3H), 2.62 (s, 6H), 3.42 (dd, J=8.3, 13.5 Hz, 1H), 3.64 (dd, J=6.0, 13.5 Hz, 1H), 4.03 (dd, J=6.0, 8.3 Hz, 1H), 6.91 (s, 2H), 7.15 (d, J=4.0 Hz, 1H), 7.34 (d, J=4.0 Hz, 1H).

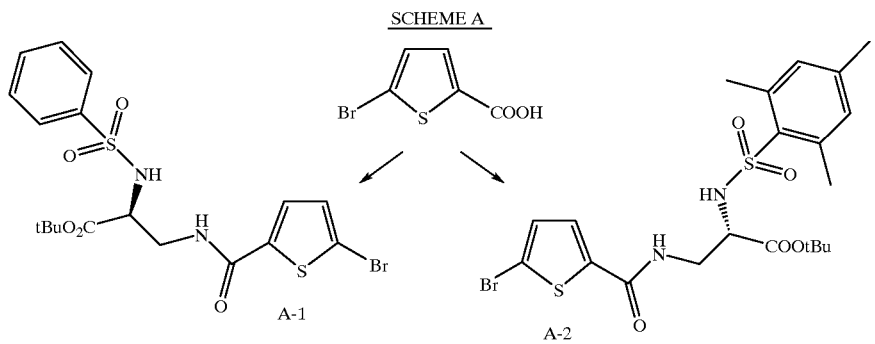

SCHEME A

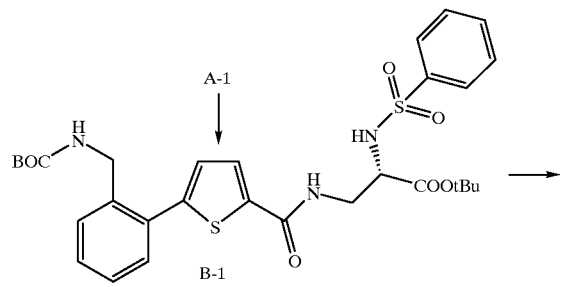

SCHEME B

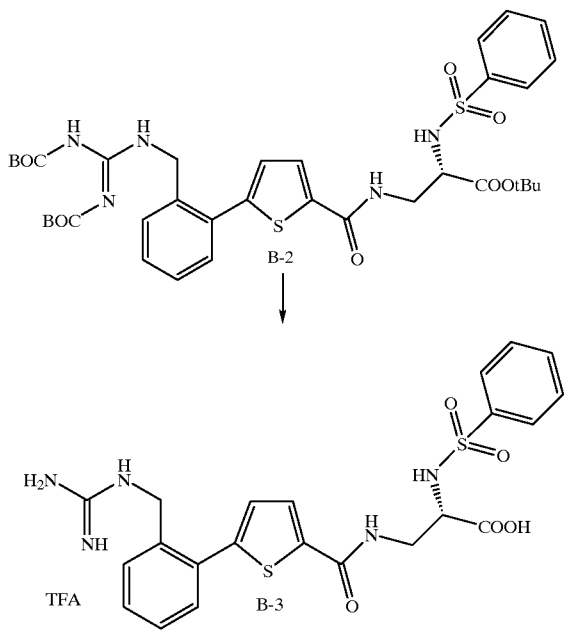

2-Benzenesulfonylamino-3-({5-[2-(tert-butoxycarbonylamino-methyl)-phenyl]-thiophene-2-carbonyl}-amino) propionic acid tert-butyl ester (B-1)

Compound A-1 (247 mg, 0.50 mmol), (2-bromobenzyl)-carbamic acid tert-butyl ester (434 mg, 1.51 mmol), hexa-n-butylditin (1.02 mL, 2.02 mmol) and bis-(triphenylphospine)palladium(II) chloride (11 mol, 39 mg) was placed in 1,4 dioxane (35 mL). The reaction system was degassed and stirred at 90° C. for 3 h. The reaction mixture was concentrated and the residue chromatographed. Elution with 26% ethyl acetate in hexane gave compound B-1 as a yellow residue (118 mg, 38% yield).

$^1$H NMR (300 MHz, CDCl$_3$) δ: 1.29 (s, 9H, tBu), 1.43 (s, 9H, BOC), 3.61 (m, 1H), 3.90 (m, 2H), 4.38 (d, J=5.3 Hz, 2H, CH$_2$), 4.78 (br s, 1H, NH), 5.83 (d, J=7.8 Hz, 1H, NH), 6.74 (br s, 1H, NH), 6.98 (d, J=3.6 Hz, lH), 7.2–7.6 (m, 8H, ArH), 7.86 (d, J=7.2 Hz, 1H (Ar).

2-Benzenesulfonylamino-3-{[5-(2-(bis-tert-butoxycarbonyl)-guanidinomethyl-phenyl-thiophene-2-carbonyl]-amino}-propionic acid tert-butyl ester (B-2)

Compound B-1 (118 mg, 0.19 mmol) in HCl/dioxane (4 M, 2 mL) was left to stand at room temperature for 10 min. The solvent was removed in vacuo to give a white solid which was then dissolved in dry DMF (2.0 mL) along with (tert-butoxycarbonylimino-pyrazol-1-yl-methyl)-carbamic acid tert-butyl ester (71 mg, 0.23 mmol), diisopropylethylamine (0.066 mL, 0.38 mmol) and stirred at room temperature for 2 days. The reaction mixture was concentrated and the residue chromatographed. Elution with 28% ethyl acetate in hexane gave compound B-2 as a white foam (114 mg, 79% yield).

$^1$H NMR (300 MHz, CDCl$_3$) δ: 1.31 (s, 9H, tBu), 1.47 (s, 9H, BOC), 1.50 (s, 9H, BOC), 3.60 (m, 1H), 3.91 (m, 2H), 4.70 (d, J=6 Hz, 2H, CH$_2$), 5.78 (d, J=7.5 Hz, 1H, NH), 6.71 (br s, 1H, NH), 7.04 (d, J=3 Hz,), 7.3–7.6 (m, 8H, ArH)), 7.87 (d, J=9 Hz, 2H, ArH), 8.58 (br s, 1H, NH).

2-Benzenesulfonylamino-3-{[5-(2-guanidinomethyl-phenyl)-thiophene-2-carbonyl]-amino}-propionic acid trifluoroacetic acid salt (B-3)

Compound B-2 (114 mg, 0.15 mmol) was dissolved in trifluoroacetic acid in dichloromethane (1:1, 1 mL) and left to stir for 5 hrs at room temperature. The mixture was concentrated and triturated with diethyl ether to give compound B-3 as a white powder (78 mg, 85% yield).

$^1$H NMR (400 MHz, CD$_3$OD) δ: 3.50 (m, 1H), 3.75 (dd, J=5.0, 13.5 Hz, 1H), 4.19 (dd, J=5.0, 8.5 Hz, 1H), 1H), 4.48 (s, 2H, CH$_2$), 7.13 (s, 1H,), 7.4–7.6 (m, 7H, ArH), 7.65 (d, J=3.8 Hz, 1H, ArH), 7.86 (d, J=7.2 Hz, 2H (Ar); ms (m/z): 502.2 (M+1).

SCHEME C

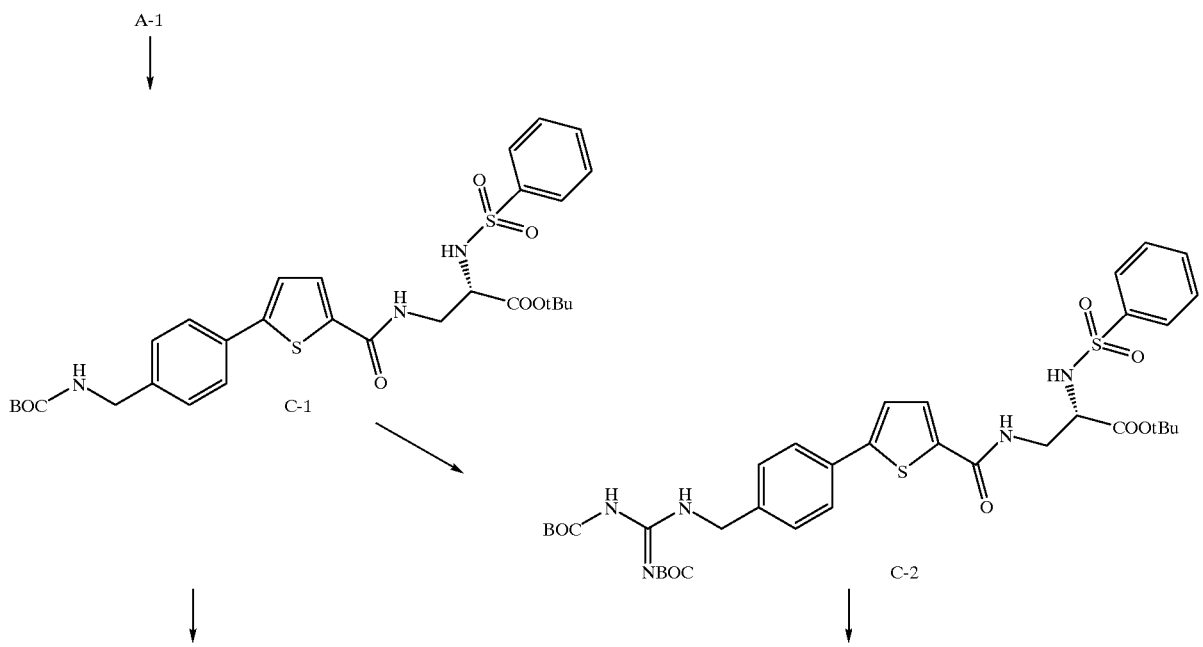

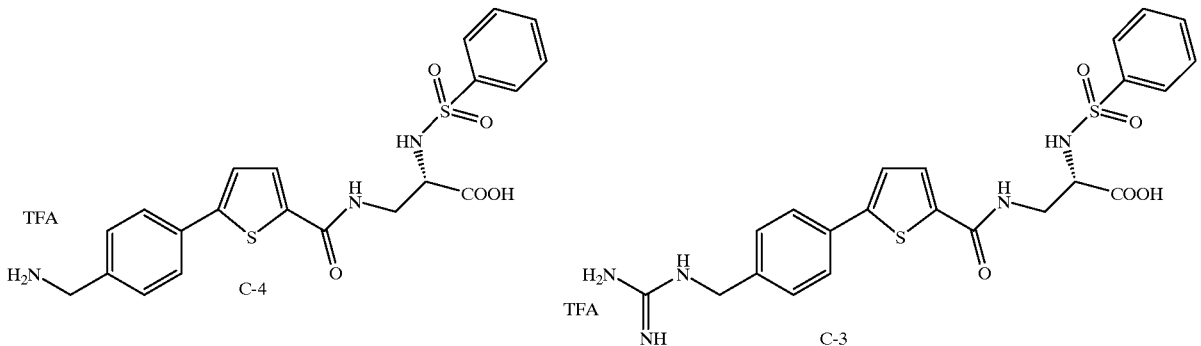

2-Benzenesulfonylamino-3-({5-[4-(tert-butoxycarbonylamino-methyl)-phenyl]-thiophene-2-carbonyl}-amino)-propionic acid tert-butyl ester (C-1)

Compound A-1 (150 mg, 0.31 mmol), (4-bromobenzyl)-carbamic acid tert-butyl ester (262 mg, 0.92 mmol), hexa-n-butylditin (0.62 mL, 1.22 mnmol) and bis-(triphenylphospine)palladium(II) chloride (11 mnmol, 23 mg) was placed in 1,4 dioxane (18 mL). The reaction system was degassed and stirred at 90° C. for 5.5 h. The reaction mixture was concentrated and the residue chromatographed. Elution with 30% ethyl acetate in hexanes gave compound C-1 as a yellow residue (63 mg, 34% yield).

$^1$H NMR (300 MHz, CDCl$_3$) δ: 1.30 (s, 9H, tBu), 1.48 (s, 9H, BOC), 3.59 (m, 1H), 3.90 (m, 2H), 4.36 (m, 2H, CH$_2$), 4.91 (br s, 1H, NH), 5.74 (d, J=5 Hz, 1H, NH), 6.68 (br s, 1H, NH), 7.28 (m, 3H, ArH), 7.56 (m, 6H, ArH), 7.88 (d, J=5.4 Hz, 2H, ArH).

2-Benzenesulfonylamino-3-{[5-(3-(bis-tert-butoxycarbonyl)-guanidinomethyl-phenyl)-thiophene-2-carbonyl]-armno}-propionic acid tert-butyl ester (C-2)

Compound C-1 (63 mg, 0.10 mmol) in HCl/dioxane (4 M, 1 mL) was left to stand at room temperature for 15 min. The solvent was removed in vacuo to give a white solid which was then dissolved in dry DMF (1.5 mL) along with (tert-butoxycarbonylimino-pyrazol-1-yl-methyl)-carbamic acid tert-butyl ester (38 mg, 0.12 mmol), diisopropylethylamine (0.035 mL, 0.20 mmol) and stirred at room temperature overnight. The reaction mixture was concentrated and the residue chromatographed. Elution with 30% ethyl acetate in hexanes gave compound C-2 as a white foam (47 mg, 62% yield).

$^1$H NMR (300 MHz, CDCl$_3$) δ: 1.28 (s, 9H, tBu), 1.48 (s, 9H, BOC), 1.52 (s, 9H, BOC), 3.60 (m, 1H), 3.90 (m, 1H), 4.64 (d, J=5 Hz, 2H, CH$_2$), 5.76 (d, J=7 Hz, 1H, NH), 6.70 (br s, 1H, NH), 7.25 (m, 2H, ArH), 7.35 (d, J=9 Hz, 2H, ArH), 7.45–7.63 (m, 5H, ArH), 7.86 (d, J=6.0 Hz, 2H, (Ar), 8.64 (br s, 1H, NH).

2-Benzenesulfonylamino-3-{[5-(4-guanidinomethyl-phenyl)-thiophene-2-carbonyl]-amino}-propionic acid trifluoroacetic acid salt (C-3)

Compound C-2 (47 mg, 0.062 mmol) was dissolved in trifluoroacetic acid in dichloromethane (1:1, 1 mL) and left to stir for 3 hrs at room temperature. The mixture was concentrated and triturated with diethyl ether to give compound C-3 as a white powder (35 mg, 92% yield).

$^1$H NMR (400 MHz, CD$_3$OD) δ: 3.50 (m, 1H), 3.74 (m, 1H), 4.21 (m, 1H), 4.46 (s, 2H, CH$_2$), 7.4–7.6 (m, 7H, ArH), 7.74 (d, J=7.9 Hz, 2H, ArH), 7.85 (d, J=7.3 Hz, 2H).

2-Benzenesulfonylamino-3-({5-[4-(methyl)-phenyl]-thiophene-2-carbonyl}-amino)-propionic acid trifluoroacetic acid salt (C-4)

Compound C-1 (6.8 mg, 0.011 mmol) was dissolved in trifluoroacetic acid in dichloromethane (1:1, 1 mL) and left to stir for 3 hrs at room temperature. The mixture was concentrated and triturated with diethyl ether to give compound C-4 as a beige powder (5.3 mg, 84% yield).

$^1$H NMR (300 MHz, CD$_3$OD) δ: 3.33 (m, 1H), 3.50 (m, 1H), 3.72 (m, 1H), 4.12 (s, 2H), 7.5–7.8 (m, 11H, ArH).

SCHEME D

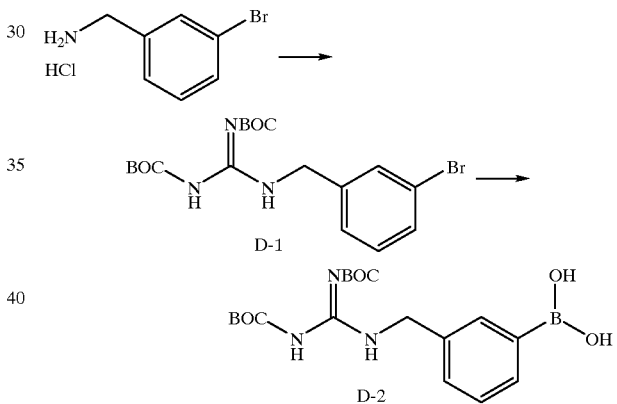

N-(3-Bromo-benzyl)-bis-(tert-butoxycarbonyl) guanidine (D-1)

A mixture of 3-bromobenzylamine hydrochloride (4.9 g, 22.02 mmol), (tert-butoxycarbonylimino-pyrazol-1-yl-methyl)-carbamic acid tert-butyl ester (6.2 g, 20.0 mmol) and diisopropylethylamine (7 mL, 40.2 mmol) in dimethylformamide(20 mL) was stirred for 72 hrs at room temperature. The solvent was removed and the crude reaction product was taken up in ethyl acetate (400 mL). The solution was washed with 0.1 N hydrochloric acid and with saturated sodium bicarbonate-saturated sodium chloride solution (1:1) (30 mL), dried over sodium sulfate and evaporated. The solid thus obtained was triturated with cold hexane-ether mixture (4:1) yielding 6 g of compound D-1. The soluble part left after filtration of the solid was chromatographed over silica gel (hexane-ethyl acetate=85:15 as eluent) and 2.2 g of compound D-1 was obtained (total yield 8.2 g, 95% yield)

¹HNMR (400 MHz, CD₃OD) δ: 1.48 (s, 9H), 1.55 (s, 9H), 4.58 (s, 2H), 7.26–7.33 (m, 2H), 7.44–7.46 (m, 1H), 7.53 (s, 1H)

3-Bis(tert-butoxycarbonyl)guanidinomethyl phenylboronic acid (D-2)

To a slurry of compound D-1 (12.58 g, 29.39 mmol) in ether (150 mL) at 78° C. was added dropwise methyllithium (1.4 M in ether, 63 mL, 88.18 mmol) while maintaining the internal temperature at below −65° C. The mixture slowly became homogeneous upon addition of methyllithium. After complete addition, the mixture was allowed to stir for 30 min. tert-Butyllithium (1.7 M in pentane, 52 mL, 88.18 mmol) was then added dropwise again maintaining the temperature below −65° C. After stirring for 30 min, triisopropyl borate (68 mL, 294 mmol) was then added dropwise while keeping the temperature at less than −65° C. After complete addition, the cooling bath was removed and the reaction mixture was allowed to warm to room temperature and stirred overnight. The mixture was then cooled to about −30° C. and a potassium hydrogen sulfate solution (5%, 200 mL) was then cautiously added. The reaction mixture was then allowed to room temperature and solid potassium hydrogensulfate was added until pH 2. The mixture was then stirred at room temperature for 2 h and the two phases were allowed to separate. The aqueous layer was further extracted with ethyl acetate (3×100 mL). The combined extracts were then washed with brine, dried (Na₂SO₄), filtered and concentrated. Purification by chromatography eluting with 25–30% acetone in hexane gave compound D-2 as a white foam (7.6 g, 65% yield).

¹H NMR (400 MHz, CDCl₃) δ: 1.50 (s, 9 H), 1.56 (s, 9 H), 4.77 (d, 2 H, CH₂, J=5.0 Hz), 7.35 (m, 1 H), 7.60 (m, 1 H), 8.16 (s, 1 H), 8.20 (d, 1 H, J=7.3 Hz), 8.69 (br s, 1H, NH), 11.79 (s, 1 H, NH).

SCHEME E

A-1

↓

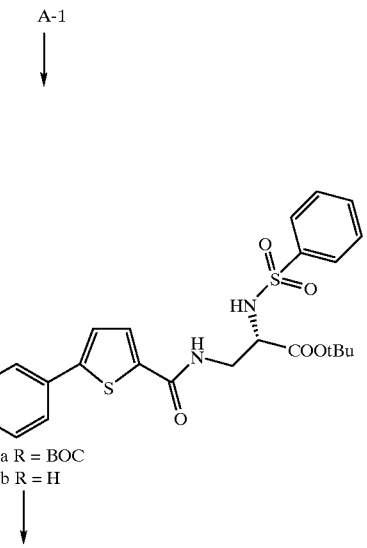

E-1a R = BOC
E-1b R = H

↓

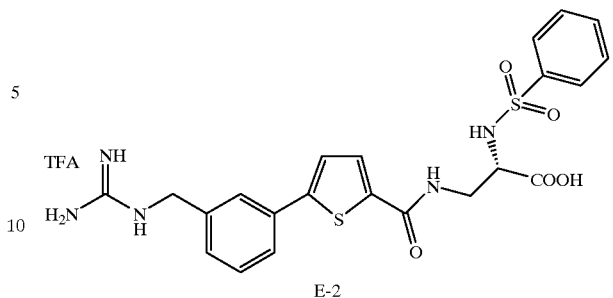

E-2

2-Benzenesulfonylamino-3-{[5-(3-(bis-tert-butoxycarbonyl)-guanidinomethyl-phenyl)-thiophene-2-carbonyl]-amino}-propionic acid tert-butyl ester (E-1a) and 2-benzenesulfonylamino-3-{[5-(3-(tert-butoxycarbonyl)-guanidinomethyl-phenyl)-thiophene-2-carbonyl]-amino}-propionic acid tert-butyl ester (E-1b)

Compound D-2 (4.01 g, 10.2 mmol), compound A-1 (4.16 g, 8.5 mmol), tetrakistriphenylphosphine palladium (295 mg, 0.255 mmol) and aqueous sodium carbonate (1 M, 42 mL) were placed in DME (100 mL). The system was degassed and stirred at 57° C. under nitrogen for overnight. The reaction mixture was concentrated, dissolved in ethyl acetate, washed with water, brine and dried over sodium sulfate. Removal of solvent in vacuo gave a yellow foam which was chromatographed. Elution with 40% ethyl acetate in hexanes gave compound E-1a as a white foam (1.87 g, 29% yield).

¹H NMR (400 MHz, CDCl₃) δ: 1.32 (s, 9H, t-Bu), 1.50 (s, 9H, BOC), 1.54 (s, 9H, BOC), 3.62 (m, 1H), 3.90 (m, 2H), 4.67 (s, 2H, CH₂), 5.78 (s, 1H, NH), 6.70 (s, 1H, NH), 7.27–7.60 (m, 9H), 7.88 (d, J=7.5 Hz, 2H), 8.66 (s, 1H, NH), 11.57 (s, 1H, NH).

Further elution with 15% methanol in dichloromethane gave a foam which solidified upon addition of dichloromethane giving compound E-1b (1.49 g, 25% yield).

¹H NMR (CD₃OD) δ: 1.26 (s, 9H, t-Bu), 1.47 (s, 9H, BOC), 3.51 (dd, J=7.6 Hz, 13.3 Hz, 1H), 3.67 (dd, J=6.1, 13.5 Hz, 1H), 4.14 (m, 1H), 4.48 (s, 2H, CH₂), 7.33 (d, J=7.4 Hz, 1H), 7.40–7.66 (m, 8H, ArH), 7.85 (d, J=7.4 Hz, 2H, ArH).

2-Benzenesulfonylamino-3-{[5-(3-guanidinomethyl-phenyl)-thiophene-2-carbonyl]-amino}-propionic acid trifluoroacetic acid salt (E-2)

Compound E-1b (1.49 g, 2.26 mmol) was dissolved in trifluoroacetic acid in dichloromethane (1:1, 20 mL) and left to stir for 6 hrs at room temperature. The mixture was concentrated and triturated with diethyl ether to give compound E-2 as a white powder (1.39 g, >99% yield).

¹H NMR (400 MHz, CD₃OD) δ: 3.50 (dd, J=8.5, 13.6 Hz, 1H), 3.74 (dd, J=5.0, 13.6 Hz, 1H), 4.17 (dd, J=5.1, 8.5 Hz, 1H), 4.49 (s, 2H, CH₂), 7.35 (d, J=8.0 Hz, 1H), 7.43–7.51 (m, 5H, ArH), 7.59 (d, J=3.8 Hz, 1H, ArH), 7.69 (m, 2H, ArH), 7.86 (m, 2H, ArH); ms(m/z): 502.3 (M+1).

SCHEME F

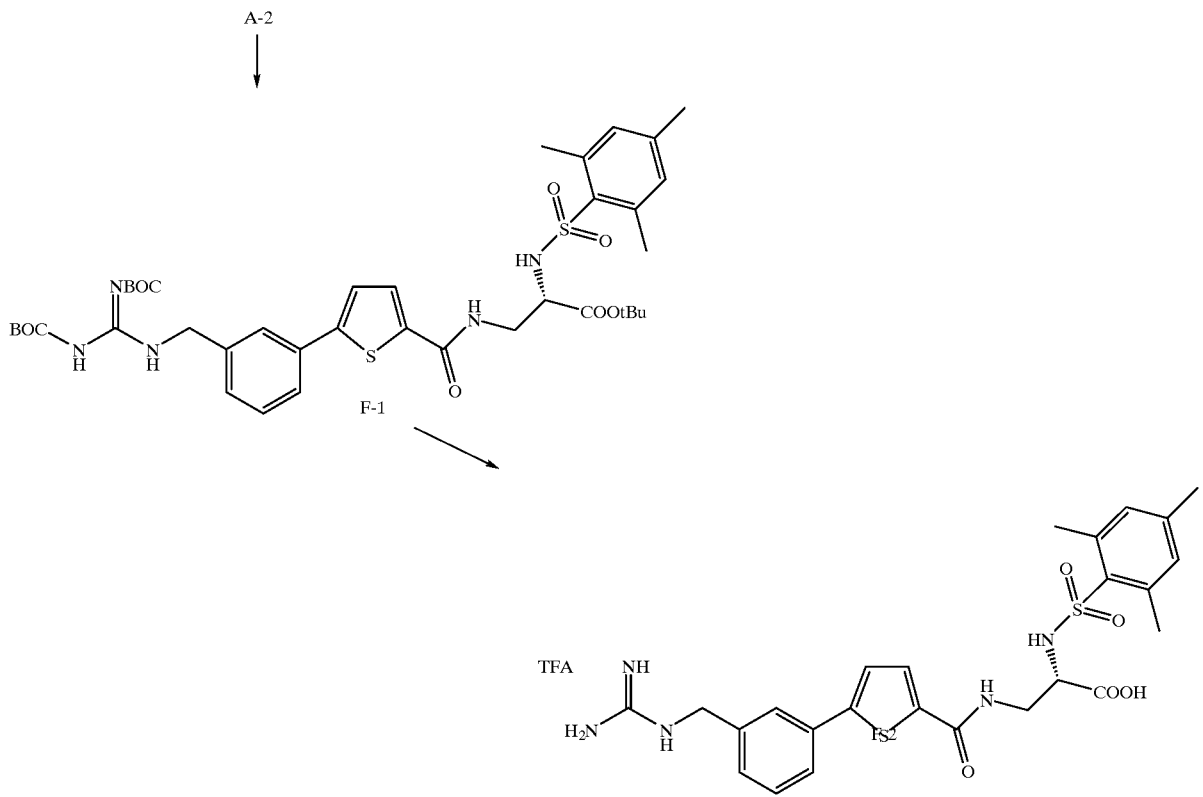

3-{[5-(3-(Bis tert-butoxycarbonyl-guanidinomethyl-phenyl)-thiophene-2-carbonyl]-amino}-2-(2,4,6-trimethyl-benzenesulfonylamino)-propionic acid tert-butyl ester (F-1)

A mixture of compound D-2 (3.60 g, 9.16 mmol), compound A-2 (3.89 g, 7.33 mmol) and tetrakistriphenylphosphine palladium (0) (850 mg, 0.73 mmol) in ethylene glycol dimethyl ether (70 mL) and aqueous sodium carbonate (1 M, 29.3 mL, 29.3 mmol) was degassed by 3 freeze/thaw cycles. The mixture was then stirred at 55° C. for 8 h. The reaction mixture was then concentrated and the residue was then partitioned between ethyl acetate (150 mL) and water (50 mL). The aqueous layer was further extracted with ethyl acetate (3×50 mL). The combined extracts were then washed with brine (100 mL), dried ($Na_2SO_4$), filtered, and concentrated to dryness. Purification by chromatography eluting with 25–50% ethyl acetate in hexane gave compound F-1 as a foam (4.2 g, 72% yield).

$^1$H NMR (400 MHz, $CDCl_3$) δ: 1.35 (s, 9 H), 1.51 (s, 9 H), 1.55 (s, 9 H), 2.29 (s, 3 H), 2.66 (s, 3 H), 2.67 (s, 3 H), 3.6 (m, 1 H), 3.8 (m, 1 H), 3.9 (m, 1 H), 4.72 (d, 2 H, $CH_2$, J=4.4 Hz), 5.80 (d, 1 H, NH, J=7.1 Hz), 6.71 (br t, 1 H, NH, J=4.9 Hz), 6.96 (s, 2 H), 7.29 (m, 1 H), 7.41 (t, 1 H, J=7.7 Hz), 7.52 (d, 1 H, J=3.9 Hz), 7.56 (d, 1 H, J=7.9 Hz), 7.62 (s, 1 H), 8.73 (s, 1 H, NH), 11.56 (s, 1 H, NH).

3-{[5-(3-Guanidinomethyl-phenyl)-thiophene-2-carbonyl]-amino}-2-(2,4,6-trimethyl-benzenesulfonylamino)-propionic acid trifluoroacetic acid salt (F-2)

A solution of compound F-1 (4.2 g, 5.25 mmol) in a mixture of trifluoroacetic acid and dichloromethane (1:1, 60 mL) was stirred at room temperature for 4 h. The solution was then concentrated and the resulting solid was triturated with ether and dried under high vacuum. Compound F-2 was obtained as a beige solid (3.3 g, 96% yield).

$^1$H NMR (400 MHz, $CD_3OD$) δ: 2.14 (s, 3 H), 2.61 (s, 3 H), 2.62 (s, 3 H), 3.49 (m, 1 H), 3.74 (m, 1 H), 4.15 (m, 1 H), 4.50 (s, 2 H, $CH_2$), 6.84 (s, 2 H), 7.35 (d, 1 H, J=7.5 Hz), 7.41 (d, 1 H, J=4.1 Hz), 7.50 (m, 2 H), 7.68 (m, 2 H), 8.40 (t, 1 H, J=5.7 Hz).

SCHEME G

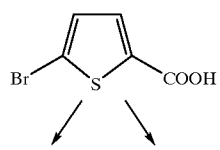

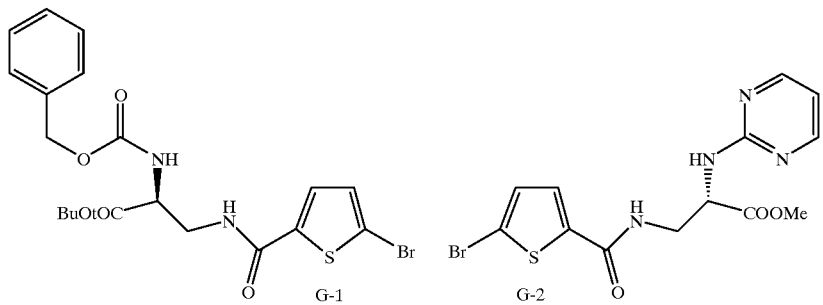

2-Benzyloxycarbonylamino-3-[(5-bromo-thiophene-2-carbonyl)-anino]-propionic acid tert-butyl ester (G-1)

4-methylmorpholine 0.70 mL, 6.38 mmol) was added to a mixture of compound A-1 (660 mg, 3.19 mmol), 3-Amino-2-benzyloxycarbonylamino-propionic acid tert-butyl ester (1.05 g, 3.19 mmol), 1-[3-(dimethylamino)propyl]-3-ethylcarboiimide hydrochloride (611 mg, 3.19 mmol) and 1-hydroxybenzotriazole (431 mg, 3.19 mmol) in dry DMF (10 mL). The mixture was stirred at room temperature overnight. The reaction mixture was concentrated and dissolved in ethyl acetate (100 mL) and washed with 5% citric acid (50 mL). The aqueous layer was extracted 2× with ethyl acetate. The combined organic layers were dried over sodium sulfate, solvent removed, and the residue chromatographed. Elution with 10% ethyl acetate in hexanes gave compound G-1 as a white syrup (1.25 g, 86% yield).

$^1$H NMR (300 MHz, CDCl$_3$) δ: 3.70 (m, 1H), 3.81 (m, 1H), 4.42 (m, 1H), 5.12 (d, J=1.5 Hz, 2H, CH$_2$), 5.80 (d, J=2.0 Hz, 1H, NH), 6.91 (br s, 1H, NH), 7.00 (d, J=1.8 Hz, 1H), 7.15 (d, J=1.8 Hz, 1H), 7.33 (m, 5H, ArH).

3-[(5-Bromo-thiophene-2-carbonyl)-amino]-2-(pyrimidin-2-ylamino)-propionic acid methyl ester (G-2)

4-methylmorpholine (0.23 mL, 2.10 mmol) was added to a mixture of 5-bromothiophene-2-carboxylic acid (124 mg, 0.60 mmol), 3-amino-2-(pyrimidin-2-ylamino)-propionic acid methyl ester bis-hydrochloride salt (161 mg, 0.60 mmol), 1-[3-(dimethylamino)propyl]-3-ethylcarboiimide hydrochloride (115 mg, 0.60 mmol) and 1-hydroxybenzotriazole (81 mg, 0.60 mmol) in dry DMF (2 mL). The mixture was stirred at room temperature overnight. The reaction mixture was concentrated, solvent removed in vacuo and the residue chromatographed. Elution with 5% methanol in dichloromethane gave compound G-2 as a yellow foam (186 mg, 81% yield).

$^1$H NMR (300 MHz, CDCl$_3$) δ: 3.79 (s, 3H, Me), 3.95 (m, 2H), 4.84 (m, 1H), 6.65 (t, J=1.9 Hz, 1H, NH, 6.99 (d, J=2 Hz, 2H), 7.34 (d, J=2.0 Hz, 2H, ArH), 8.33 (m, 5H, ArH).

SCHEME H

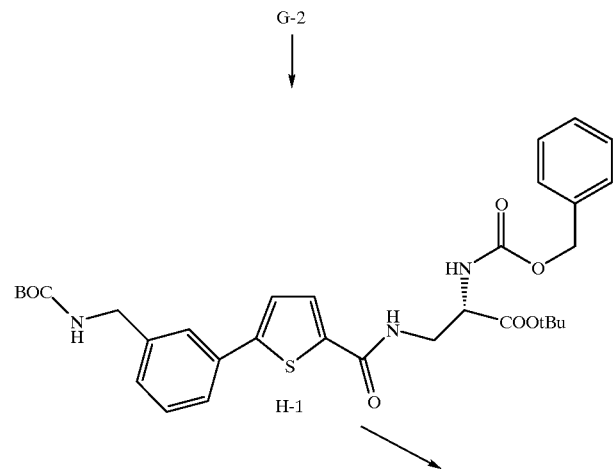

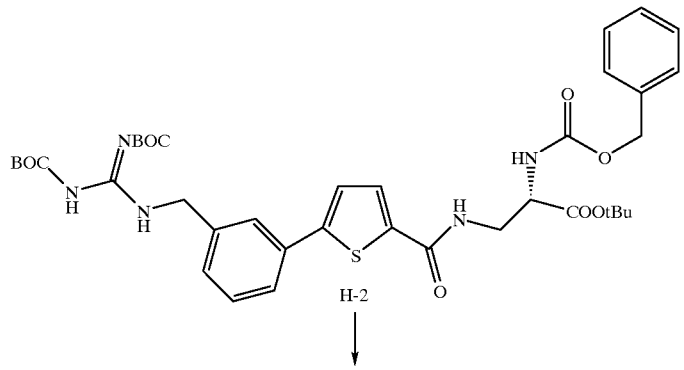

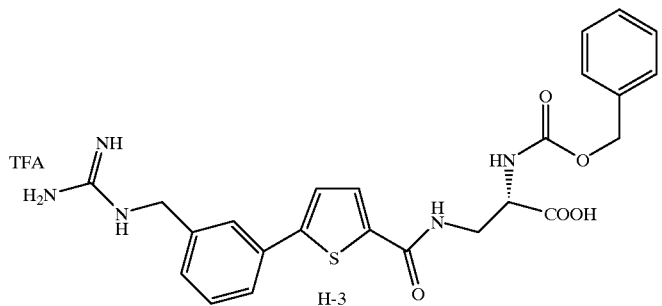

2-Benzyloxycarbonylamino-3-({5-[3-(tert-butoxycarbonylamino-methyl)-phenyl]-thiophene-2-carbonyl}-amino)-propionic acid tert-butyl ester (H-1)

A mixture of compound G-2 (155 mg, 0.32 mmol), (3-bromo-benzyl)-carbamic acid tert-butyl ester (275 mg, 0.96 mmol), hexa-n-butylditin (1.28 mmol, 0.65 mL) and bis-(triphenylphospine)palladium(II) chloride (11 mmol, 25 mg) in 1,4 dioxane (18 mL) was degassed and stirred at 90° C. for 3 h. The reaction mixture was concentrated and the residue chromatographed. Elution with 30% ethyl acetate in hexanes gave compound H-1 as a yellow residue (65 mg, 33% yield).

$^1$H NMR (300 MHz, CDCl$_3$) δ: 1.48 (s, 18H tBu and BOC), 3.83 (m, 2H), 4.37 (d, J=6.0 Hz, 2H, CH$_2$), 4.46 (m, 1H), 4.92 (br s, 1H, NH), 5.15 (s, 2H CH$_2$), 5.85 (d, J=6.0 Hz, 1H, NH), 6.87 (br s, 1H, NH), 7.2–7.4 (m, 9H, ArH), 7.53 (m, 2H, ArH).

2-Benzyloxycarbonylamino-3-{[5-(3-(bis-tert-butoxycarbonyl)-guanidinomethyl-phenyl)-thiophene-2-carbonyl]-amino}-propionic acid tert-butyl ester (H-2)

Compound H-1 (65 mg, 0.11 mmol) in HCl/Dioxane (4 M, 1 mL) was left to stand at room temperature for 15 min. The solvent was removed in vacuo to give a residue (59 mg, 0.10 mmol) which was then dissolved in dry DMF (1.5 mL) along with (tert-butoxycarbonylimino-pyrazol-1-yl-methyl)-carbamic acid tert-butyl ester (40 mg, 0.12 mmol), diisopropylethylamine (0.037 mL, 0.20 mmol) and stirred at room temperature overnight. The reaction mixture was concentrated and the residue chromatographed. Elution with 27% ethyl acetate in hexanes gave compound H-2 as a white foam (47 mg, 61% yield).

$^1$H NMR (300 MHz, CDCl$_3$) δ: 1.46 (s, 18H, tBu, BOC), 1.52 (s, 9H, BOC), 3.82 (m, 2H), 4.44 (m, 1H), 4.69 (d, J=6.0 Hz, 2H, CH$_2$), 5.12 (s, 2H, CH$_2$), 5.85 (d, J=6.1 Hz, 1H, NH), 6.88 (br s, 1H, NH), 7.2–7.4 (m, 9H, ArH), 7.53 (d, J=9.1 Hz, 1H, ArH), 7.60 (s, 1H, ArH), 8.70 (br s, 1H, NH).

2-Benzyloxycarbonylamino-3-{[5-(3-guanidinomethyl-phenyl)-thiophene-2-carbonyl]-amino}-propionic acid (trifluoroacetic acid salt) (H-3)

Compound H-2 (47 mg, 0.062 mmol) was dissolved in trifluoroacetic acid in dichloromethane (1:1, 1 mL) and left to stir for 3 hrs at room temperature. The mixture was concentrated and triturated with diethyl ether to give compound H-3 as a white powder (31 mg, 82% yield).

$^1$H NMR (400 MHz, CD$_3$OD) δ: 3.74 (m, 1H), 3.84 (m, 1H), 4.48 (m, 3H), 7.2–7.4 (m, 6H, ArH), 7.44 (d, J=3.9 Hz, 1H, ArH), 7.49 (t, J=7.7 Hz, 1H, ArH), 7.5–7.7 (m, 3H); ms: (m/z) 496.6 (M+1).

SCHEME I

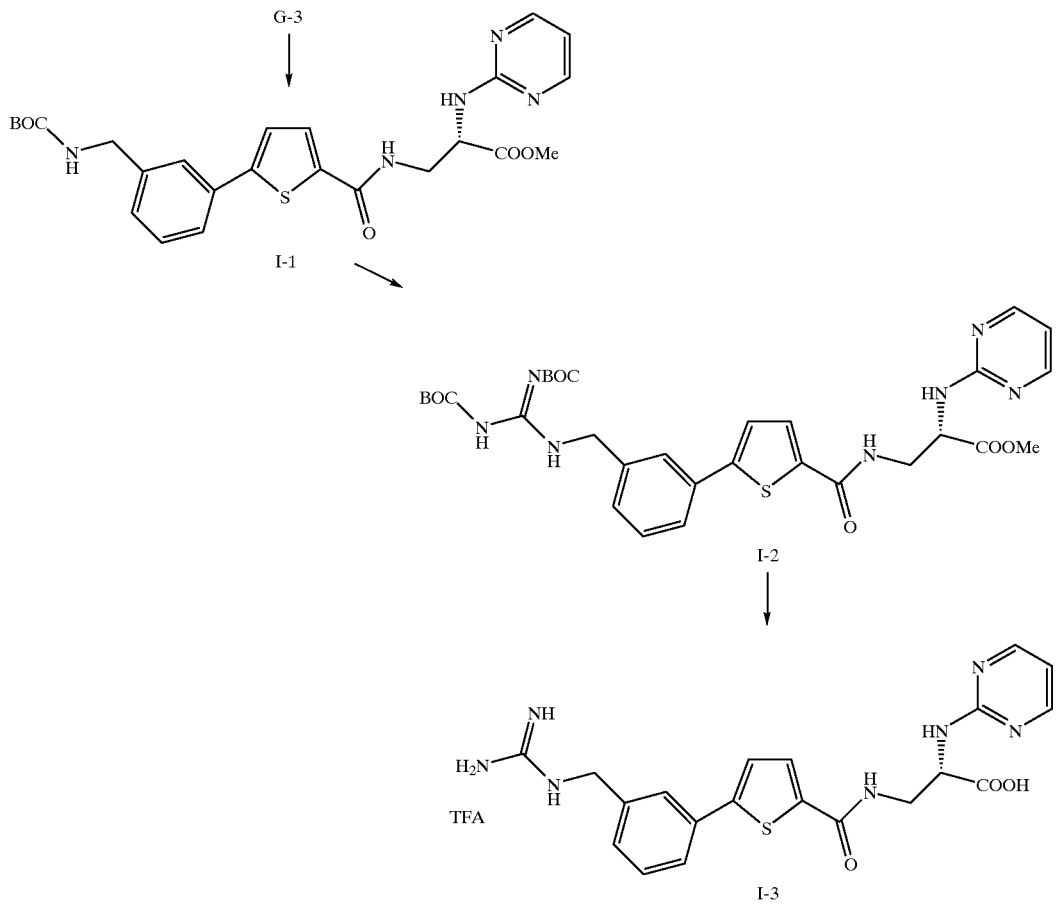

3-({5-[3-(tert-Butoxycarbonylamino-methyl)-phenyl]-thiophene-2-carbonyl}-amino)-2-(pyrimidin-2-ylamino)-propionic acid methyl ester (I-1)

Compound G-3 (186 mg, 0.48 mmol), (3-bromo-benzyl)-carbamic acid tert-butyl ester (285 mg, 1.44 mmol), hexan-butylditin (0.97 mL, 1.92 mmol) and bis-(triphenylphospine) palladium(II) chloride (11 mmol, 37 mg) were placed in 1,4 dioxane (35 mL). The reaction system was degassed and stirred at 90° C. for 5 h. The reaction mixture was concentrated and the residue chromatographed. Elution with 1% methanol in dichloromethane gave compound I-1 as a yellow foam (72 mg, 29% yield).

$^1$H NMR (300 MHz, CDCl$_3$) δ: 3.81 (s, 3H, Me), 3.96 (m, 2H), 4.32 (d, J=6.0 Hz, 2H, CH$_2$), 4.86 (br s, 1H, NH), 4.92 (m, 1H), 6.64 (br s, 1H, NH), 7.2–7.6 (m, 9H C, ArH), 8.31 (br s, 1H, NH).

3-{[5-(3-(bis-tert-Butoxycarbonyl)-guanidinomethyl-phenyl)-thiophene-2-carbonyl]-amino}-2-(pyrimidin-2-ylamino)-propionic acid methyl ester (I-2)

Compound I-1 (72 mg, 0.14 mmol) in HCl/dioxane (4 M, 1.5 mL) was left to stand at room temperature for 15 min. The solvent was removed in vacuo and dissolved in dry DMF (2.0 mL) along with (tert-butoxycarbonylimino-pyrazol-1-yl-methyl)-carbamic acid tert-butyl ester (52 mg, 0.17 mmol), diisopropylethylamine 0.049 mL, 0.28 mmol) and stirred at room temperature overnight. The reaction mixture was concentrated and the residue chromatographed. Elution with 1% methanol in dichloromethane gave compound I-2 as a white foam (57 mg, 62% yield).

$^1$H NMR (300 MHz, CDCl$_3$) δ: 3.82 (s, 3H, Me), 3.97 (m, 3H), 4.66 (d, J=6.0 Hz, 2H (CH$_2$), 4.88 (br s, 1H, NH), 6.65 (br s, 1H, NH), 7.2–7.6 (m, 9H, ArH), 8.64 (br s, 1H, NH).

3-{[5-(3-Guanidinomethyl-phenyl)-thiophene-2-carbonyl]-amino}-2-(pyrimidin-2-ylamino)-propionic acid trifluoroacetic acid salt (I-3)

Compound I-2 (56 mg, 0.088 mmol) and lithium hydroxide monohydrate (7.3 mg, 0.176 mmol) in THF:H$_2$O (4:1, 1 mL) was stirred at room temperature for 4 hrs. The reaction mixture was then diluted with chloroform (3 mL) and acidified with 5% citric acid (2 mL). The aqueous layer was extracted 2× with chloroform (3 mL) and the combined organic layers dried over sodium sulfate. The solvent was removed in vacuo to give a yellow foam which was dissolved in trifluoroacetic acid in dichloromethane (1:1, 1 mL) and left to stir for 3 hrs at room temperature. The mixture was concentrated, triturated with diethyl ether, and lyophilyzed to give compound I-3 as a white powder (29 mg, 60% yield).

$^1$H NMR (400 MHz, CD$_3$OD) δ: 3.50 (m, 1H), 3.90 (m, 1H), 4.03 (m, 1H), 4.47 (s, 2H, CH$_2$), 7.34 (d, J=7.3 Hz, 2H), 7.4–7.7 (m, 9H, ArH); ms: (m/z) 440.2 (M+1).

SCHEME J

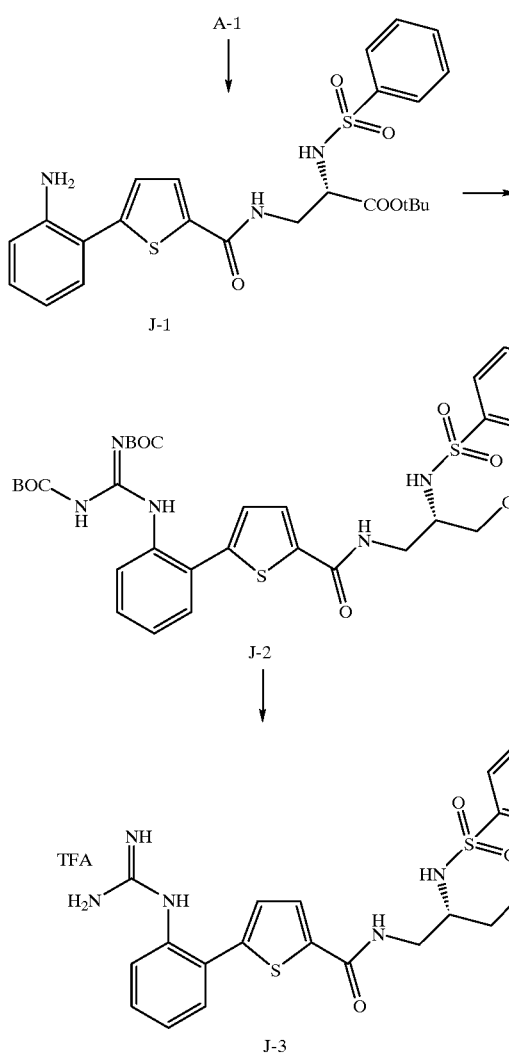

3-{[5-(2-Amino-phenyl)-thiophene-2-carbonyl]-amino}-2-benzenesulfonylamino-propionic acid tert-butyl ester (J-1)

Compound A-1 (343 mg, 0.701 mmol), 2-bromoaniline (724 mg, 4.20 mmol), hexa-n-butylditin (1.41 mL, 2.80 mmol) and bis-(triphenylphospine)palladium(II) chloride (11 mmol, 54 mg) was placed in 1,4 dioxane (50 mL). The reaction system was degassed and stirred at 90° C. overnight. The reaction mixture was concentrated and the residue chromatographed. Elution with 30% ethyl acetate in hexanes gave compound J-1 as a yellow foam (120 mg, 34% yield).

$^1$H NMR (400 MHz, CDCl$_3$) δ: 1.27 (s, 9H, tBu), 3.60 (m, 1H), 3.90 (m, 2H), 5.88 (d, J=8.4 Hz, 1H, NH), 6.80 (d, J=7.5 Hz, 2H), 7.1–7.7 (m, 7H, ArH), 7.87 (d, J=6.9 Hz, 2H, ArH).

2-Benzenesulfonylamino-3-{[5-(2-(bis-tert-butoxycarbonyl)-guanidino-phenyl)-thiophene-2-carbonyl]-amino}-propionic acid tert-butyl ester (J-2)

Compound J-1 (120 mg, 0.24 mmol) in dry DMF (2.0 mL) along with (tert-butoxycarbonylimino-pyrazol-1-yl-methyl)-carbamic acid tert-butyl ester (149 mg, 0.48 mmol), diisopropylethylamine (0.083 mL, 0.48 mmol) and stirred at 57° C. overnight. The reaction mixture was concentrated and the residue chromatographed. Elution with 25% ethyl acetate in hexanes gave compound J-2 as a white foam (25 mg, 14% yield).

$^1$H NMR (400 MHz, CDCl$_3$) δ: 1.31 (s, 9H, tBu), 1.48 (s, 18H, BOC), 3.62 (m, 1H), 3.85–4.00 (m, 2H), 5.79 (d, J=7.2 Hz, 1H, NH), 6.66 (t, J=5.5 Hz, 1H, NH), 7.4–7.6 (m, 9H, ArH), 7.86 (d, J=7.2 Hz, 2H, ArH).

2-Benzenesulfonylamino-3-{(5-(2-guanidino-phenyl)-thiophene-2-carbonyll-amino}-propionic acid trifluoroacetic acid salt (J-3)

Compound J-2 (24 mg, 0.032 mmol) was dissolved in trifluoroacetic acid/dichloromethane (1:1, 1 mL) and left to stir for 4 hrs at room temperature. The mixture was concentrated and triturated with diethyl ether to give compound J-3 as a white powder (19 mg, >99% yield).

$^1$H NMR (400 MHz, CD$_3$OD) δ: 3.60 (m, 1H), 3.82 (m, 1H), 3.94 (m, 1H), 7.36 (d, J=3.7 Hz, 2H), 7.4–7.6 (m, 6H, ArH), 7.8–7.9 (m, 3H, ArH); ms(m/z) 488.2 (M+1).

SCHEME K

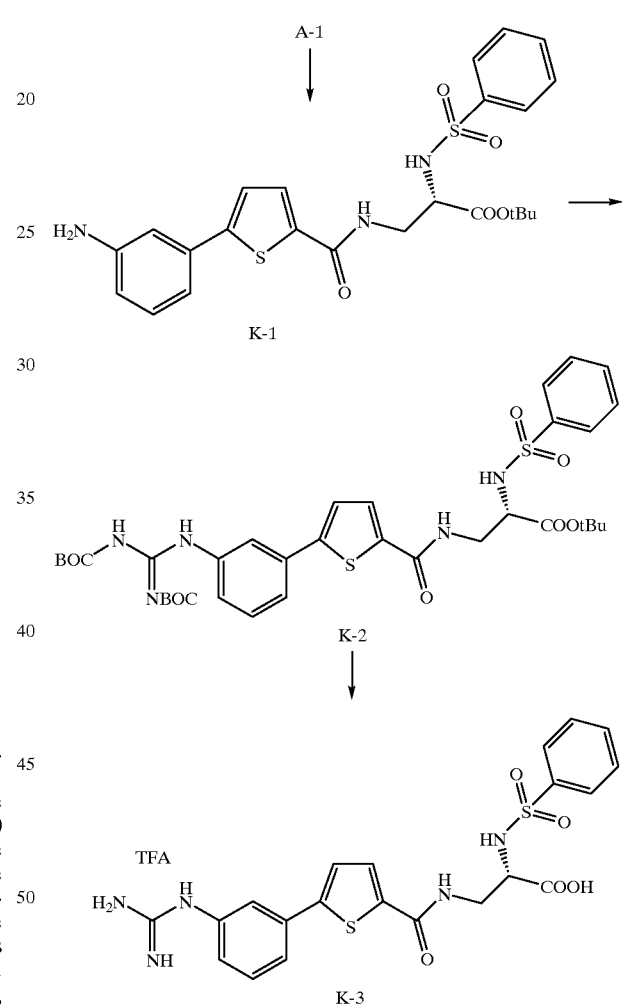

3-{[5-(3-Amino-phenyl)-thiophene-2-carbonyl]-amino}-2-benzenesulfonylamino-propionic acid tert-butyl ester (K-1)

Compound A-1 (4.10 g, 8.4 mmol), tetrakistriphenylphosphine palladium (290 mg, 0.25 mmol) and aqueous sodium carbonate (2 M, 42 mL, 84 mmol) were placed in DMF (100 mL). The system was degassed and stirred at 80° C. under nitrogen for 2 hours. The reaction mixture was concentrated, dissolved in ethyl acetate, washed with water, brine and dried over sodium sulfate. Removal of solvent in vacuo gave K-1 as a beige foam (4.16 g, >99% yield).

2-Benzenesulfonylamino-3-{[5-(3-(bis-tert-butoxycarbonyl)-guanidino-phenyl)-thiophene-2-carbonyl]-amino}-propionic acid tert-butyl ester (K-2)

Compound K-1 (8.38 mmol, (tert-butoxycarbonylimino-pyrazol-1-yl-methyl)-carbamic acid tert-butyl ester (3.11 g, 10.0 mmol), diisopropylethylamine (2.91 mL, 16.7 mmol) and DMAP (20 mmol, 204 mg, 1.67 mmol) were placed in dry THF (40 mL) and stirred at 55° C. overnight. The reaction mixture was concentrated and the residue chromatographed. Elution with 40% ethyl acetate in hexanes gave compound K-2 as a white foam (3.33 g, 53% yield).

$^1$H NMR (400 MHz, CDCl$_3$) δ: 1.32 (s, 9H, t Bu), 1.55 (s, 18 H, 2 BOC), 3.64 (m, 1H), 3.84 (m, 1H), 3.95 (m, 1H), 5.95 (s, 1H, NH), 6.41 (s, 1 H, NH), 6.69 (s, 1H), 7.37 (d, J=4.8 Hz, 2H (CH=C, ArH), 7.50 (m, 3H, ArH), 7.67 (m, 2H, ArH), 7.88 (m, 3H, ArH), 10.42 (s, 1H, NH), 11.64 (s, 1H, NH).

2-Benzenesulfonylamino-3-{[5-(3-guanidino-phenyl)-thiophene-2-carbonyl]-amino}-propionic acid (trifluoroacetic acid salt)(K-3)

Compound R-2 (3.33 g, 4.48 mmol) was dissolved in trifluoroacetic acid/dichloromethane (1:1, 30 mL) and left to stir for 6 hrs at room temperature. The mixture was concentrated and triturated with diethyl ether to give compound K-3 as a white powder (2.68 g, 99% yield).

$^1$H NMR (400 MHz, CD$_3$OD) δ: 3.50 (dd, J=8.5, 13.6 Hz, 1H), 3.73 (dd, J=5.0, 13.6 Hz, 1H), 4.18 (dd, J=5.0, 8.5 Hz, 1H), 7.30 (d, J=7.9 Hz, 1H (CH=C), 7.50 (m, 7H, ArH), 7.71 (d, J=7.8 Hz, 1H, ArH), 7.85 (d, J=7.4 Hz, 2H, ArH); ms: (m/z) 488.3 (M+1)

SCHEME L

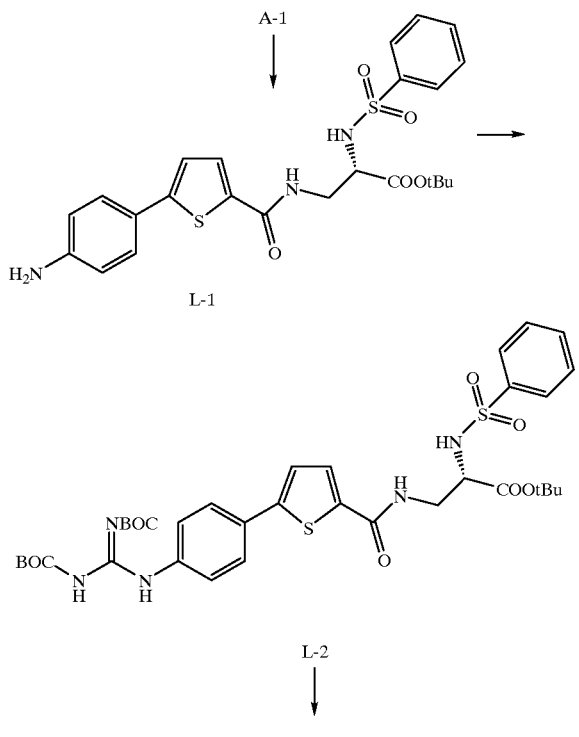

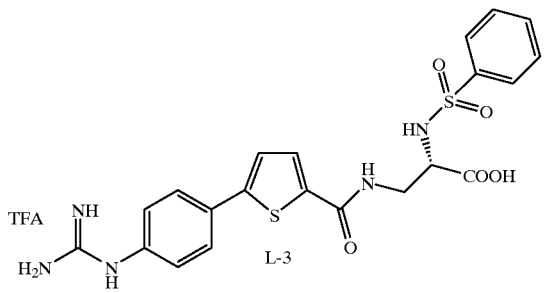

3-{[5-(4-Amino-phenyl)-thiophene-2-carbonyl]-amino}-2-benzenesulfonylamino-propionic acid tert-butyl ester (L-1)

Compound A-1 (200 mg, 0.41 mmol), 4-bromoaniline (422 mg, 2.45 mmol), hexa-n-butylditin (0.82 mL, 1.63 mmol) and bis-(triphenylphospine)palladium(II) chloride (11 mmol, 31 mg) was placed in 1,4 dioxane (30 mL). The reaction system was degassed and stirred at 90° C. for 2 days. The reaction mixture was concentrated and the residue chromatographed. Elution with 45–50% ethyl acetate in hexanes gave a yellow residue consisting of a 1:1 mixture of compound L-1 contaminated with thiophene dimer (58 mg) which was used directly in the next step.

2-Benzenesulfonylamino-3-{[5-(4-(bis-tert-butoxycarbonyl)-guanidino-phenyl)-thiophene-2-carbonyl]-amino}-propionic acid tert-butyl ester (L-2)

Crude compound L-1 (58 mg) in dry DMF (1.0 mL) along with (tert-butoxycarbonylimino-pyrazol-1-yl-methyl)-carbamic acid tert-butyl ester (72 mg, 0.23 mmol), diisopropylethylamine 0.040 mL, 0.23 mmol) and stirred at 55° C. overnight. The reaction mixture was concentrated and the residue chromatographed. Elution with 26% ethyl acetate in hexanes gave compound L-2 as a white foam (7.0 mg, 2% yield over 2 steps).

$^1$H NMR (300 MHz, CDCl$_3$) δ: 1.29 (s, 9H, tBu), 1.51 (s, 18H, BOC), 3.61 (m, 1H), 3.88 (m, 2H), 5.87 (d, J=7.5 Hz, 1H, NH), 6.66 (br s, 1H, NH), 7.20 (d, J=3.6 Hz, 1H), 7.4–7.6 (m, 6H, ArH), 7.67 (d, J=6.9 Hz, 2H, ArH), 7.86 (d, J=6.9 Hz, 2H, ArH).

2-Benzenesulfonylamino-3-{[5-(4-guanidino-phenyl)-thiophene-2-carbonyl]-amino}-propionic acid trifluoroacetic acid salt (L-3)

Compound L-2 (7.0 mg, 0.009 mmol) was dissolved in trifluoroacetic acid in dichloromethane (1:1, 1 mL) and left to stir for 3 hrs at room temperature. The mixture was concentrated and triturated with diethyl ether to give compound L-3 as a white powder (5 mg, 93% yield).

$^1$H NMR (400 MHz, CD$_3$OD) δ: 3.50 (d, J=6.7 Hz, 1H), 3.72 (m, 1H), 4.15 (m, 1H), 7.36 (d, J=8.1 Hz, 2H), 7.4–7.6 (m, 6H, ArH), 7.8–7.9 (m, 3H, ArH); ms (m/z): 488.2 (M+1).

Scheme M

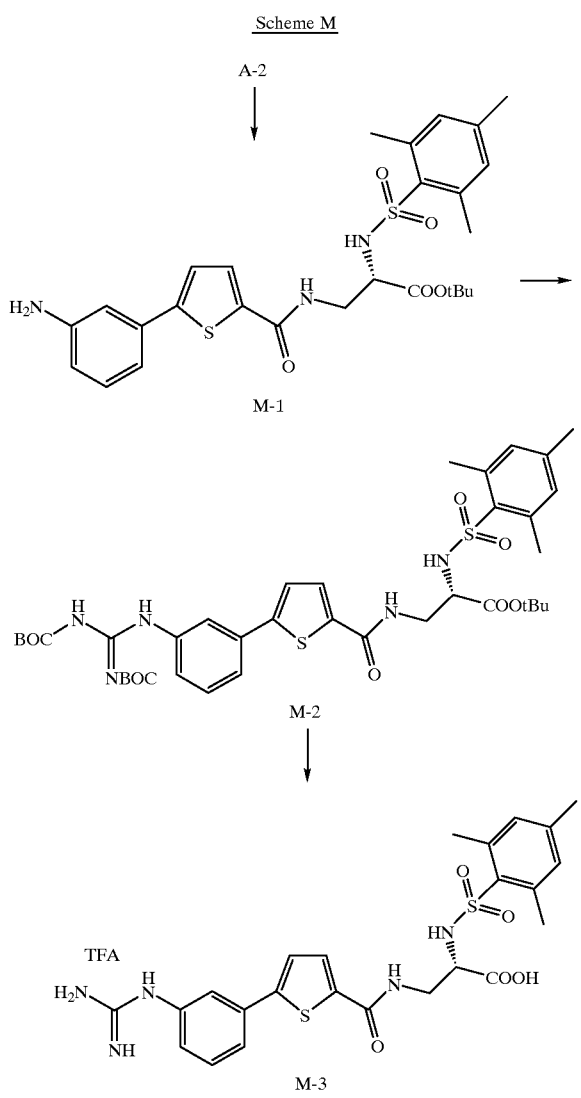

3-{[5-(3-Amino-phenyl)-thiophene-2-carbonyl]-amino}-2-(2,4,6-trimethyl-benzenesulfonylamino)-propionic acid tert-butyl ester (M-1)

3-Aminophenylboronic acid hemnisulfate (3.33 g, 17.92 mmmol), compound A-2 (7.93 g, 14.93 mmol), tetrakistriphenylphosphine palladium (517 mg, 0.447 mmol) and aqueous sodium carbonate (2 M, 75 mL) were placed in DMF (180 mL). The system was degassed and stirred at 80° C. under nitrogen for one hour. The reaction mixture was concentrated, dissolved in ethyl acetate, washed with water, brine and dried over sodium sulfate. Removal of solvent in vacuo gave compound M-1 as a beige foam containing fine black particles (degraded catalyst) (yield >99%). $^1$H NMR (400 MHz, CD$_3$OD) δ: 1.28 (s, 9H, t-Bu), 2.19 (s, 3H, CH$_3$), 2.63 (s, 6H, 2CH$_3$), 3.46(dd, J=8.2, 13.5 Hz, 1H), 3.67 (dd, J=6.0, 13.5 Hz, 1H), 4.06 (dd, J=6.1, 8.1 Hz, 1H), 6.72 (d, J=1.9, 8.0 Hz, 1H), 6.90 (s, 2H), 7.00 (d, J=7.7 Hz, 1H ArH), 7.04 (s, 1H, ArH), 7.15 (t, J=7.8 Hz, 1H, ArH), 7.30 (d, J=4.0 Hz, 1H, ArH), 7.50 (d, J=4.0 Hz, 1H, ArH).

3-{[5-(3-(bis-tert-butoxycarbonyl)-guanidino-phenyl)-thiophene-2-carbonyl]-amino}-2-(2,4,6-trimethyl-benzenesulfonylamino)-propionic acid tert-butyl ester (M-2)

Compound M-1 (14.93 mmol (assuming 100% conversion), (tert-butoxycarbonylimino-pyrazol-1-yl-methyl)-carbamic acid tert-butyl ester (5.55 g, 14.93 mmol), diisopropylethylamine (5.20 mL, 29.9 mmol) and DMAP (364 mg, 2.98 mmol) were placed in dry THF (70 mL) and stirred at 55° C. overnight. The reaction mixture was concentrated and the residue chromatographed. Elution with 35% ethyl acetate in hexanes gave compound M-2 as a white foam (5.97 g, 51% yield).

$^1$H NMR (400 MHz, CDCl$_3$) δ: 1.30 (s, 9H, t-Bu), 1.53 (s, 18H, 2 BOC), 2.25 (s, 3H, CH$_3$), 2.64 (s, 6H, CH$_3$), 3.64 (m, 1H), 3.80 (m, 2H), 6.34 (s, 1H, NH), 6.92 (s, 2H), 6.95 (d, J=5.7 Hz, 1H ArH), 7.22 (d, J=4.0 Hz, 1H ArH), 7.34 (d, J=4.9 Hz, 2H, ArH), 7.45 (d, J=4.0 Hz, 1H, ArH), 7.61 (d, J=2.0 Hz, 2H, ArH), 7.63–7.67 (m, 1H, ArH), 7.83 (s, 1H, ArH), 10.39 (s, 1H, NH), 11.62 (s, 1H, NH).

3-{[5-(3-Guanidino-phenyl)-thiophene-2-carbonyl]-amino}-2-(2,4,6-trimethyl-benzenesulfonylamino)-propionic acid (trifluoroacetic acid salt) (M-3)

Compound M-2 (5.97 g, 7.60 mmol) was dissolved in trifluoroacetic acid in dichloromethane (1:1, 60 mL) and left to stir for 4 hrs at room temperature. The mixture was concentrated and triturated with diethyl ether to give compound M-3 as a white powder (4.46 g, 91% yield).

$^1$H NMR (400 MHz, CD$_3$OD) δ: 2.15 (s, 3H, (CH$_3$), 2.62 (s, 6H, 2CH$_3$), 3.46 (dd, J=9.4, 13.6 Hz, 1H), 3.72 (dd, J=4.6, 13.6 Hz, 1H), 4.11 (dd, J=4.5, 9.0 Hz, 1H), 6.88 (s, 2H), 7.30 (d, J=7.9 Hz, 1H, ArH), 7.4–7.6 (m, 4H, ArH), 7.70 (d, J=7.8 Hz, 1H, ArH); ms: (m/z) 530.3 (M+1).

Scheme N

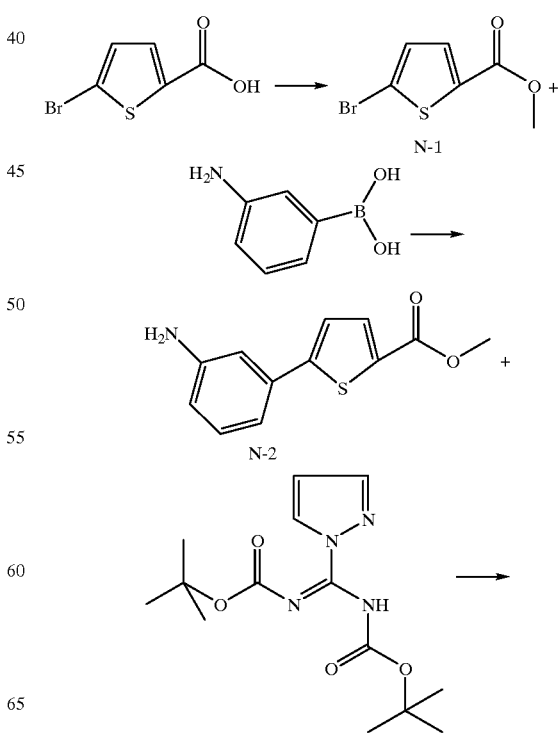

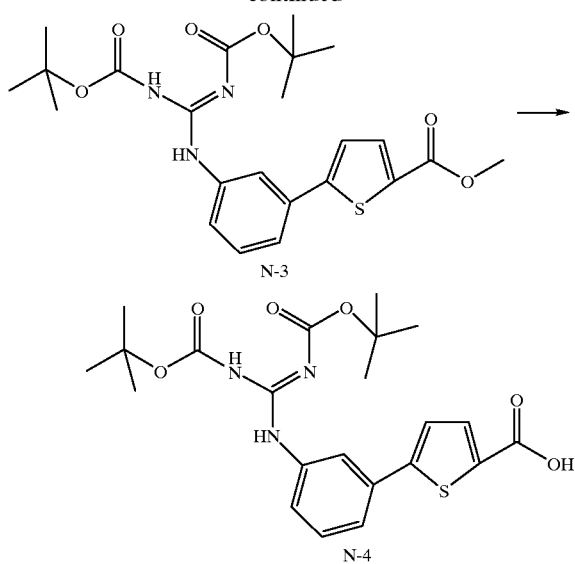

5-Bromo-thiophene-2-carboxylic acid methyl ester (N-1)

A mixture of 5-Bromo-thiophene-2-carboxylic (2.5 g, 12.00 mmol), (trimethylsilyldiazomethane (1.379 g, 12.00 mmol) in dioxane:Methanol (9:1, 15 ml) was stirred for 24 hrs at room temperature. The solvent was removed and the crude reaction product was taken up in ethyl acetate (40 mL). The solution was washed with 5% solution of sodium bicarbonate (30 mL), then with saturated sodium chloride solution (30 mL), dried over sodium sulfate and evaporated. This gave 1.6 g of compound N-1 (62% yield).

$^1$HNMR (400 MHz, CDCl$_3$) δ: 3.82 (s, 3H), 7.05 (d, 2H), 7.58 (d, 2H).

5-(3-Amino-phenyl)-thiophene-2-carboxylic acid methyl ester (N-2)

A mixture of compound N-1 (1.6 g, 7.20 mmol), 3-aminophenylboronic acid hemisulfate (1.60 g, 8.60 mmol), Palladium tetrakis triphenylphosphine (0.25 g, 0.216 mmol), sodium carbonate (40 mL, 2M, 82 mmol) in DMF (100 mL) was stirred for 2 hrs at 80° C. overnight. The solvent was removed and the crude reaction product was taken up in ethyl acetate (40 mL). The solution was washed with 5% solution of hydrochloric acid (30 mL), then with saturated sodium chloride solution (30 mL), dried over sodium sulfate and evaporated. Purification of the residue on silica gel (1:1 hexanes-EtOAc) gave 0.790 g of compound N-2 (48% yield).

$^1$HNMR (300 MHz, CDCl$_3$) δ: 3.78 (bs, 2H), 3.88 (s, 3H), 6.65 (d, 1H), 6.83 (t, 1H), 7.03 (d, 1H), 7.17–7.19 (m, 1H), 7.22 (d, 1H), 7.78 (d, 2H).

5-(3-N,N-ditertbutoxycarbonyl Guanidino-phenyl)-thiophene-2-carboxylic acid methyl ester (N-3)

A mixture of compound N-2 (1.00 g, 4.29 mmol), N,N-Diboc-1H-pyrazole-1-carboxamidine (1.60 g, 5.15 mmol), Dimethylaminopyridine (0.210 g, 1.71 mmol), diisopropylethylamine (3 mL, 1.1 mmol) in THF (100 mL) was stirred for 24 hrs at 55° C. overnight. The solvent was removed and the crude reaction product was taken up in ethyl acetate (40 mL). The solution was washed with 5% solution of hydrochloric acid (30 mL), then with saturated sodium chloride solution (30 mL), dried over sodium sulfate and evaporated. Purification of the residue on silica gel (1:2 hexanes-EtOAc) gave 0.790 g of compound N-3 (54% yield).

$^1$HNMR (300 MHz, CDCl$_3$) δ: 3.82 (s, 3H), 7.21 (d, 1H), 7.26 (m, 2H), 7.60 (m, 1H), 7.68 (d, 1H), 7.93 (s, 1H), 10.40 (s, 1H).

5-(3-N,N-ditertbutoxycarbonyl Guanidino-phenyl)-thiophene-2-carboxylic acid (N-4)

A mixture of compound N-3 (0.20 g, 0.42 mmol), Lithium hydroxide (0.15 g, 6.00 mmol), in acetonitrile (10 mL) was stirred for 4 hrs at room temperature. The solvent was removed and the crude reaction product was taken up in ethyl acetate (40 mL). The solution was neutralized with acetic acid (1.3 mL). Solvent was than dried over sodium sulfate and evaporated. Purification of the residue on silica gel (10% MeOH-EtOAc) gave 0.152 g of pure compound N-4 (78% yield).

$^1$HNMR (300 MHz, CD$_3$OD) δ: 1.50 (d, 18H), 7.41 (m, 2H), 7.55 (m, 2H), 7.70 (d, 1H), 7.99 (d, 1H).

Scheme O

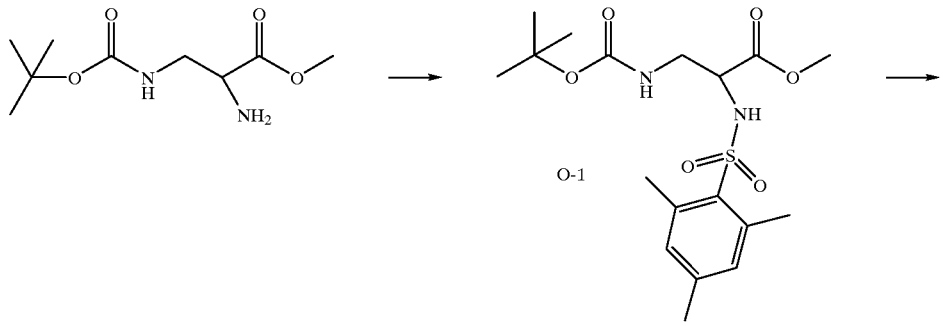

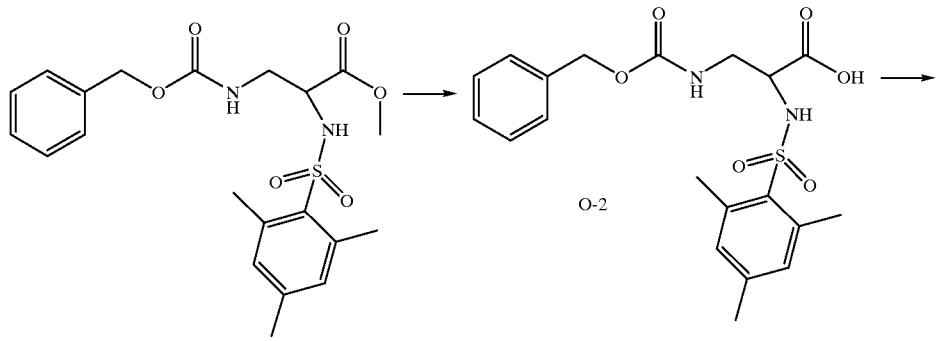
-continued
O-2
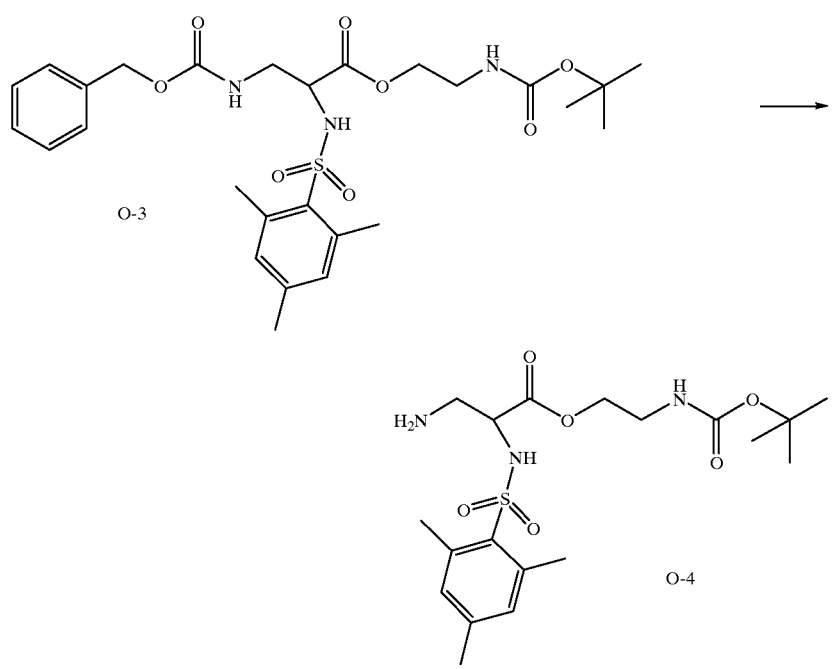
O-3
O-4
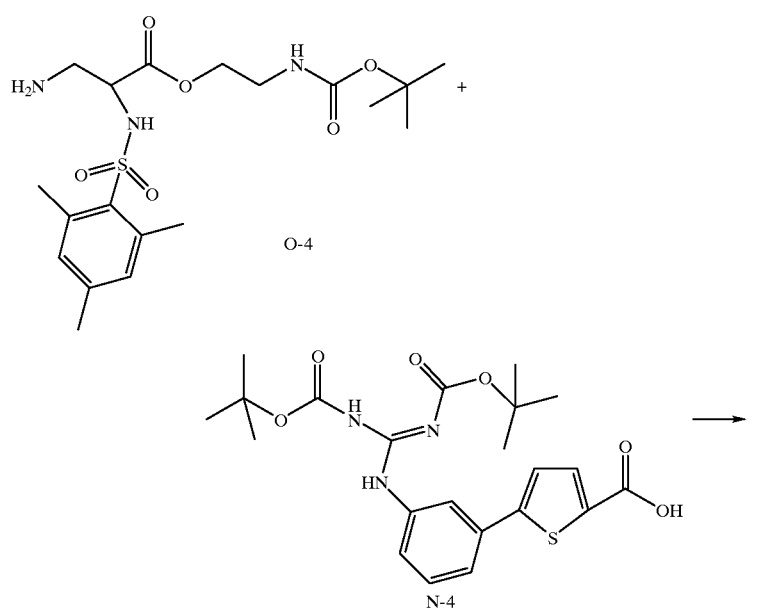
O-4
N-4

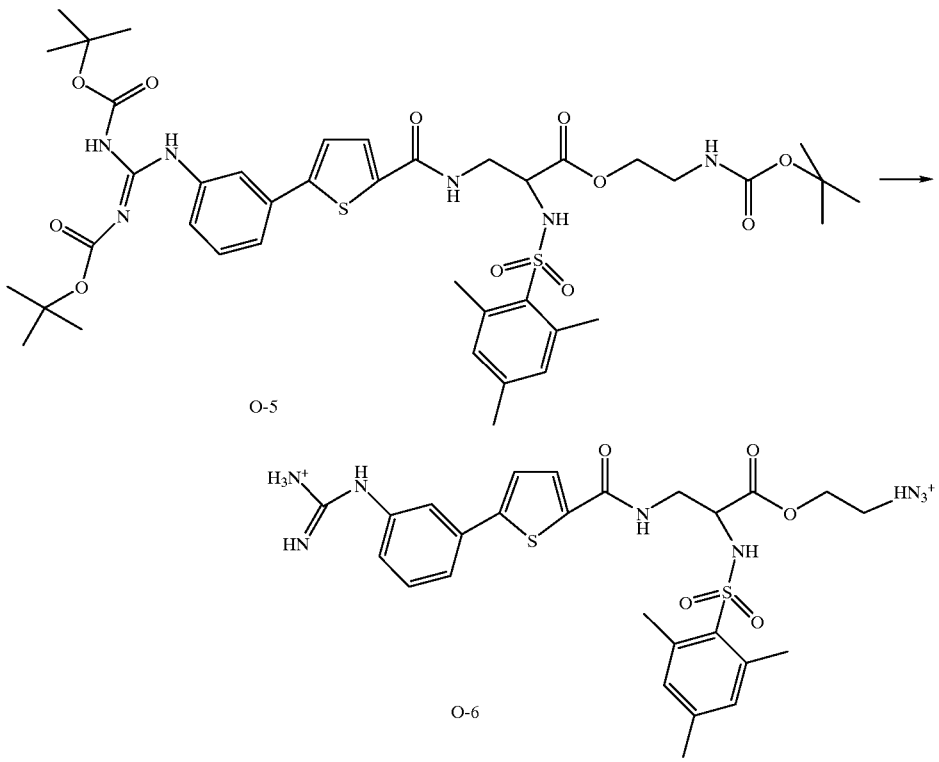

3-tert-Butoxycarbonylamino-2-(2,4,6-trimethyl-benzenesulfonylamino)-propionic acid methyl ester (O-1)

A mixture of 3-tert-Butoxycarbonylamino-2-aminopropionic acid methyl ester (3.5 g, 13.7 mmol), mesitylsulfonyl chloride (3.9 g, 17.8 mmol), DIEA (7.2 mL, 41.1 mmol) in dichloromethane (100 mL) was stirred at 0° C. for one hour and overnight at room temperature. The solvent was removed and the crude reaction product was taken up in ethyl acetate (340 mL). The solution was washed with 5% solution of sodium carbonate (30 mL), 5% solution of hydrochloric acid (30 mL), with saturated sodium chloride solution (30 mL). Solvent was than dried over sodium sulfate and evaporated. Purification of the residue on silica gel (10%MeOH-EtOAc) gave 5.00 g of pure compound O-1 (84% yield).

$^1$HNMR (300 MHz, CDCl$_3$) δ: 1.41 (s, 9H), 2.22 (s, 3H), 2.62 (s, 6H), 3.43 (m, 2H), 3.55 (s, 3H), 3.83 (m, 1H), 6.90 (s, 2H).

3-tert-Butoxycarbonylamino-2-(2,4,6-trimethyl-benzenesulfonylamino)-propionic acid methyl ester (O-2)

A mixture of compound O-1 (5.00 g, 12.4 mmol), Lithium hydroxide (5.5 g, 228 mmol), in acetonitrile (100 mL) was stirred for 4 hrs at room temperature. The solvent was removed and the crude reaction product was taken up in ethyl acetate (100 mL). The solution was neutralized with acetic acid (10.3 mL). Solvent was than dried over sodium sulfate and evaporated. Purification of the residue on silica gel (10%MeOH-EtOAc) gave 4.2 g of pure acid (87% yield). The Boc group was removed by treating the Boc derivative in TFA/CH$_2$Cl$_2$ (50 mL, 1:1) at room temperature overnight. The resulting salt (10 mmol) was than dissolved in 2N NaOH (8 mL) and cooled in an ice-water bath and stirred at this temperature. Benzyl chlorocarbonate (1.87 g, 1.58 mL, 11 mnmol) was added and the reaction mixture remained alkaline. The temperature was kept between 5 to 10° C. for 3 hrs. The alkaline solution was extracted with ether (200 mL), and the ether extract was discarded. EtOAc (200 mL) was added and the solution was than acidified with 5N HCl to congo blue. Evaporation of the organic layer afforded pure compound O-2 (4.25 g, 94% yield).

$^1$HNMR (300 MHz, CD$_3$OD) δ: 2.22 (s, 3H), 2.63 (s, 6H), 3.20–46 (m, 2H), 3.25 (s, 3H), 3.93 (m, 1H), 6.99 (s, 2H), 7.32 (s, 5H).

3-(1-Phenylmethyloxycarbonylamino)-2-(2,4,6-trimethyl-benzenesulfonylamino)-propionic acid 2-tert-butoxycarbonylamino-ethyl ester (O-3)

A mixture of compound O-2 (1.00 g, 2.18 mmol), ethanolamine (440 mg, 2.73 mmol), triethylamine (0.76 mL, 5.47 mmol) were dissolved in DMF (8 mL) and treated with benzotriazol-1-yloxytris(dimethylamino)phosphonium hexafluorophosphate (1.2 g, 2.73 mmol). The mixture was stirred at room temperature for 13 hrs. The solvent was removed and the crude reaction product was taken up in ethyl acetate (50 mL). The solution was washed with saturated sodium chloride solution (2×50 mL), 5% sodium bicarbonate solution (50 mL), saturated sodium chloride solution (2×50 mL), dried over sodium sulfate and evaporated. Purification of the residue on silica gel (EtOAc) gave 670 mg of pure compound O-3 (52% yield).

$^1$HNMR (300 MHz, CDCl$_3$) δ: 1.43 (s, 9H), 2.22 (s, 3H), 2.63 (s, 6H), 3.20 (m, 2H), 3.44 (m, 1H), 3.72–3.98 (m, 3H), 4.21 (m, 1H), 5.03 (s, 2H), 5.22–5.34 (m, 2NH), 5.80 (d, 1NH), 6.99 (s, 2H), 7.40 (s, 5H).

3-amino-2-(2,4,6-trimethyl-benzenesulfonylamino)-propionic acid 2-tert-butoxycarbonylamino-ethyl ester (O-4)

To a mixture of compound O-3 (1.00 g, 1.77 mmol) in methanol (40 mL), was added excess Pd/C. The reaction was kept under an atmosphere of hydrogen and stirred overnight at room temperature. The catalyst was removed by filtration and the solvent was evaporated. Purification of the residue on silica gel (1:5 MeOH:EtOAc) gave 630 mg (82% yield) of pure compound O-4.

¹HNMR (300 MHz, CD₃OD) δ: 1.43 (s, 9H), 2.22 (s, 3H), 2.61 (s, 6H), 2.82–3.10 (m, 2H), 3.18 (m, 2H), 3.25–3.60 (m, 2H), 3.98 (m, 1H), 7.00 (s, 2H).

3-{[5-(3-N,N-tert-butoxycarbonylguanidino-phenyl)-thiophene-2-carbonyl]-amino}-2-(2,4,6-trimethyl-benzenesulfonylamino)-propionic acid 2-tert-butoxycarbonylamino-ethyl ester (O-5)

To a mixture of 5-(3-N,N-ditertbutoxycarbonyl Guanidino-phenyl)-thiophene-2-carboxylic acid (300 mg, 0.65 mmol), compound O-4 (280 mg, 0.65 mmol), hydroxybenzotriazole (104 mg, 0.77 mmol) in DMF (70 mL), was added 1-(3-dimethylamino) propyl)-3-ethylcarbodiimide hydrochloride (150 mg, 0.77 mmol). The reaction was stirred overnight at room temperature. Insolubles were removed by filtration and the solvent was evaporated. Purification of the residue on silica gel (1:4 hexanes:EtOAc) gave 332 mg (60% yield) of pure compound O-5.

¹HNMR (300 MHz, CDCl₃) δ: 1.36 (s, 9H), 1.46(d, 18H), 2.22 (s, 3H), 2.63 (s, 6H), 3.24 (m, 2H), 3.45–3.99(m, 5H), 6.95(s, 2H), 7.20–7.85 (m, 6H).

Trifluoroacetate salt of 3-{[5-(3-Guanidino-phenyl)-thiophene-2-carbonyl]-amino}-2-(2,4,6-trimethyl-benzenesulfonylamino)-propionic acid 2-aminoethyl ester (O-6)

Compound O-4 (300 mg, 0.34 mmol) was mixed with a mixture of (1:1)TFA/CH₂Cl₂ (30 mL) and the reaction mixture was stirred at room temperature overnight. The solvent was evaporated and the residue was tritured with dry ether (2×30 mL). This gave 173 mg (88% yield) of pure compound O-6. (Solubility: 25 g/mL) (10% EtOH/saline).

¹HNMR (300 MHz, CD₃OD) δ: 2.19 (s, 3H), 2.59 (s, 6H), 3.16 (m, 2H), 3.47–3.72(m, 3H), 4.44–4.89(m, 2H), 6.87 (s, 2H), 7.29–7.90 (m, 6H).

SCHEME P

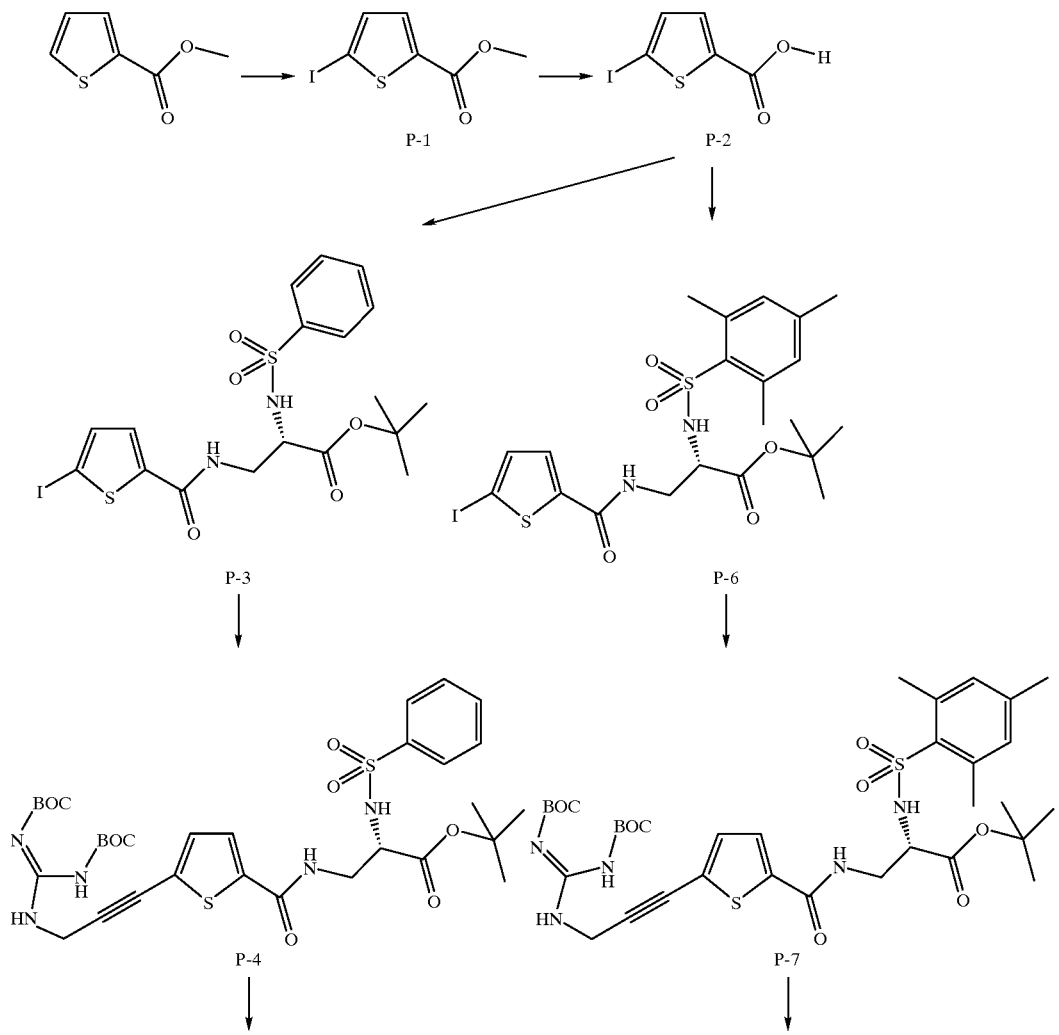

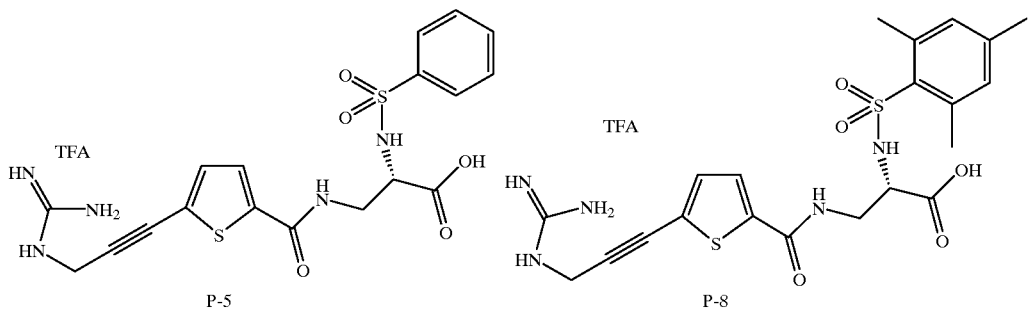

5-Iodo-thiophene-2-carboxylic acid methyl ester (P-1).

To a solution of thiophene-2-carboxylic acid methyl ester (5.0 g, 28.7 mmol) in 35 mL of anhydrous carbon tetrachloride was added iodine (3.65 g, 14.37 mmol) and [Bis(trifluoroacetoxy)iodo] benzene (6.67 g, 15.52 mmol). This mixture was stirred overnight at room temperature. Dichloromethane was then added and the mixture was extracted with a solution of sodium thiosulfate 10%. The organic layer was evaporated and the residue was purified flash chromatography (hexane 40%:chloroform 60%) to give a solid which was triturated with pentane in order to remove remaining starting material affording compound P-1 as a white solid (4.8 g, 63% yield).

$^1$H NMR (400 MHz, CDCl$_3$) d 3.89 (s, 3H), 7.28 (d, J=3.9 Hz, 1H), 7.45 (d, J=3.9 Hz, 1H).

5-Iodo-thiophene-2-carboxylic acid (P-2).

To a solution of lithium hydroxide (0.45 g, 11.19 mmol) in 17.5 mL of water was added compound P-1 (1.0 g, 3.73 mmol) in 35 mL of tetrahydrofuran. The resulting mixture was stirred for 4 hours at room temperature and was then acidified to pH 4 and extracted with ethyl acetate. The organic layer was dried (MgSO$_4$), filtered and evaporated to yield 0.86 g (91% yield) of compound P-2 as a white solid.

$^1$H NMR (400 MHz, CD$_3$OD) d 7.35 (d, J=3.8 Hz, 1H), 7.43 (d, J=3.9 Hz, 1H).

(S)-2-Benzenesulfonylamino-3-[(5-iodo-thiophene-2-carbonyl)-amino]-propionic acid tert-butyl ester (P-3).

Compound P-2 (0.40 g, 1.57 mmol) and the hydrochloric acid salt of (S)-3-amino-2-benzenesulfonylamino-propionic acid tert-butyl ester (0.64 g, 1.89 mmol) were added to a solution of N,N-Diisopropylethylamine (0.55 mL) in 50 mL of N,N-dimethylformamide. O-(7-Azabenzotriazole-1-yl)-N,N,N',N'-tetramethyluronium hexafluoro-phosphate (0.72 g, 1.89 mmol) was then added and the reaction mixture was stirred at room temperature for 5 h. After the solvent was evaporated, an extraction was done with ethyl acetate, citric acid 10% and a saturated solution of sodium bicarbonate. The organic fractions were dried over magnesium sulfate. After the filtration and evaporation of the solvent, purification on silica gel (Hex 60%:AcOEt 40%) provided 0.84 g (quantitative yield) of compound P-3 as a white solid.

$^1$H NMR (400 MHz, CDCl$_3$) d 1.25 (s, 9H), 3.60 (m, 1H), 3.78 (m, 1H), 4.06 (m, 1H), 6.40 (d, J=8.6 Hz, 1H), 7.08 (d, J=3.9 Hz, 1H), 7.17 (d, J=3.9 Hz, 2H), 7.41 (m, 2H), 7.48 (m, 1H), 7.82 (d, J=7.3 Hz, 2H).

(S)-2-Benzenesulfonylamino-3-{[5-(3-(N,N-Bis-BOC-guanidino)-prop-1-ynyl)-thiophene-2-carbonyl]-amino}-propionic acid tert-butyl ester (P-4).

To a solution of N-Prop-2-ynyl-(N,N-Bis-BOC-guanidine) (0.133 g, 0.45 mmol) in 3.5 mL of N,N-dimethylformamide were added compound P-3 (0.20 g, 0.37 mmol), triethylamine (0.10 mL), tetrakistriphenylphosphine palladium(0) (0.043 g, 0.037 mmol) and copper iodide (0.014 g, 0.075 mmol). The resulting yellow mixture was stirred overnight at room temperature. Evaporation of the solvent followed by a flash chromatography (CH$_2$Cl$_2$ 97%:acetone 3%) provided 0.22 g (83% yield) of compound P-4 as a clear oil.

$^1$H NMR (400 MHz, CDCl$_3$) d 1.29 (s, 9H), 1.51 (s, 9H), 1.52 (s, 9H), 3.59 (m, 1H), 3.84 (m, 1H), 3.95 (m, 1H), 4.51 (d, J=5.0 Hz, 2H), 6.00 (d, J=7.8 Hz, 1H), 6.89 (t, J=5.7 Hz, 1H), 7.10 (d, J=3.9 Hz, 1H), 7.39 (d, J=3.9 Hz, 1H), 7.48 (m, 2H), 7.56(m, 1H), 7.85 (m, 2H), 8.56 (m, 1H), 11.49 (m, 1H).

(S)-2-Benzenesulfonylamino-3-{[5-(3-guanidino-prop-1-ynyl)-thiophene-2-carbonyl]-amino}-propionic acid, trifluoroacetic acid salt (P-5).

To a solution of compound P-4 (0.009 g, 0.012 mmol) in 0.75 mL of anhydrous dichloromethane was added 0.75 mL of trifluoroacetic acid. After the mixture was stirred overnight, the solvent was evaporated. The residue was then triturated with diethyl ether and dissolved in methanol. Evaporation of the solvent gave 5.0 mg (72% yield) of compound P-5 as a white powder.

$^1$H NMR (400 MHz, CD$_3$OD) d 3.56 (m, 1H), 3.67 (m, 1H), 3.75 (m, 1H), 4.32 (s, 2H), 7.22 (d, J=3.9 Hz, 1H), 7.49 (m, 2H), 7.55 (m, 2H), 7.86 (d, J=7.1 Hz, 2H).

(S)-3-[(5-Iodo-thiophene-2-carbonyl)-amino]-2-(2,4,6-trimethyl-benzenesulfonylamino)-propionic acid tert-butyl ester (P-6).

Compound P-2 (0.056 g, 0.22 mmol) and the hydrochloric acid salt of (S)-3-amino-2-(2,4,6,-trimethyl-benzyloxycarbonylamino)-propionic acid tert-butyl ester (0.10 g, 0.26 mmol ) were added to N,N-Diisopropylethylamine (0.08 mL) in 7 mL of N,N-dimethylformamide. O-(7-Azabenzotriazol-1-yl)-N,N,N',N'-tetramethyluronium hexafluorophosphate (0.099 g, 0.26 mmol) was then added and the reaction mixture was stirred at room temperature for 5 h. After the solvent was evaporated, an extraction was done with ethyl acetate, citric acid 10% and a saturated solution of sodium bicarbonate. The organic layer were combined, dried (MgSO$_4$), filtered and concentrated. Purification of the residue on silica gel (60% hexane:40% ethyl acetate) provided 0.124 g (98% yield) of compound P-6 as a white solid.

$^1$H NMR (400 MHz, CDCl$_3$) d 1.31 (s, 9H), 1.51 9s, 9H), 1.52 (s, 9H), 2.28 (s, 3H), 2.64 (s, 6H), 3.56 (m, 1H), 3.84 (m, 2H), 4.51 (d, J=5.0 Hz, 2H), 5.85 (d, J=7.3 Hz, 1H), 6.81 (t, J=4.9 Hz, 1H), 6.93 (s, 2H), 7.13 (d, J=3.9 Hz, 1H), 7.39 (d, J=3.9 Hz, 1H), 8.56 (m, 1H), 11.50 (m, 1H).

(S)-3-{[5-(3-(N,N-Bis-BOC-Guanidino)-prop-1-ynyl)-thiophene-2-carbonyl]-amino}-2-(2,4,6-trimethyl-benzenesulfonylamino)-propionic acid tert-butyl ester (P-7).

To a solution of N-Prop-2-ynyl-(N,N-Bis-BOC-guanidine) (0.076 g, 0.257 mmol) in 2 mL of N,N- dimethylformamide were added compound P-6 (0.124 g, 0.214 mmol), triethylamine (0.06 mL), tetrakistriphenylphosphine palladium(0) (0.025 g, 0.0214 mmol) and copper iodide (0.0082 g, 0.0428 mmol). The resulting yellow mixture was stirred overnight at room temperature. Evaporation of the solvent followed by a flash chromatography (CH$_2$Cl$_2$ 97%: acetone 3%) gave 0.096 g (60% yield) of compound P-7 as a clear oil.

$^1$H NMR (400 MHz, CDCl$_3$) d 1.31 (s, 9H), 1.51 9s, 9H), 1.52 (s, 9H), 2.28 (s, 3H), 2.64 (s, 6H), 3.56 (m, 1H), 3.84 (m, 2H), 4.51 (d, J=5.0 Hz, 2H), 5.85 (d, J=7.3 Hz, 1H), 6.81 (t, J=4.9 Hz, 1H), 6.93 (s, 2H), 7.13 (d, J=3.9 Hz, 1H), 7.39 (d, J=3.9 Hz, 1H), 8.56 (m, 1H), 11.50 (m, 1H).

(S)-3-{[5-(3-Guanidino-prop-1-ynyl)-thiophene-2-carbonyl]-amino}-2-(2,4,6-trimethyl-benzenesulfonylamino)-propionic acid, trifluoroacetic acid salt (P-8).

To a solution of compound P-7 (0.009 g, 0.012 mmol) in 0.75 mL of anhydrous dichloromethane was added 0.75 mL of trifluoroacetic acid. After the mixture was stirred overnight, the solvent was evaporated. The residue was then triturated with diethyl ether and dissolved in methanol. Evaporation of the solvent gave 4.55 mg (65% yield) of compound P-8 as a white powder.

$^1$H NMR (400 MHz, CD$_3$OD) d 2.24 (s, 3H), 2.64 (s, 6H), 3.50–3.68 (m, 3H), 4.33 (s, 2H), 6.92 (s, 2H), 7.21 (d, J=3.9 Hz, 1H), 7.47 (d, J=3.9 Hz, 1H).

SCHEME Q

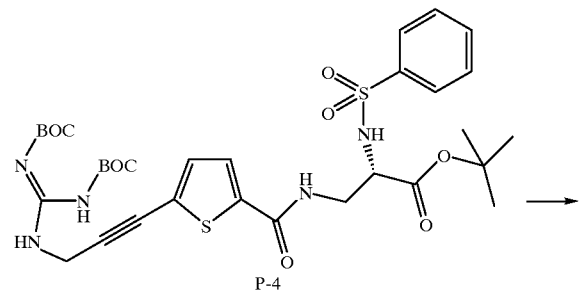

P-4

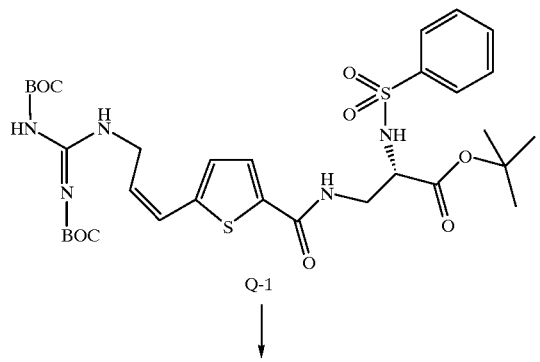

Q-1

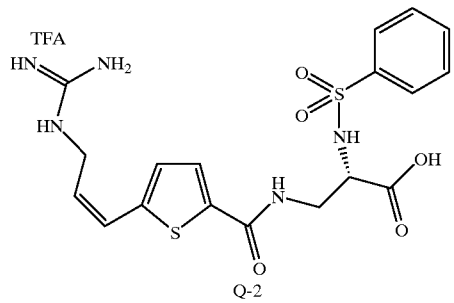

Q-2

(S)-2-Benzenesulfonylamino-3-{[5-(3-(N,N-Bis-BOC-guanidino)-(Z)-propenyl)-thiophene-2-carbonyl]-amino}-propionic acid tert-butyl ester (Q-1).

To a solution of compound P-4 (0.024 g, 0.034 mmol) in 0.8 mL of anhydrous tetrahydrofuran was added 5% palladium/charcoal (0.0077 g), one drop of thiophene and ethanol (0.4 mL). The resulting mixture was stirred for 60 minutes at room temperature under an hydrogen atmosphere. This was followed by the filtration of the mixture and evaporation of the solvent. A flash chromatography (pentane 45%:dichloromethane 45%:acetone 10%) provided 5 mg (20% yield) of compound Q-1 as a clear oil.

$^1$H NMR (400 MHz, CDCl$_3$) d 1.32 (s, 9H), 1.51 (s, 9H), 1.53 (s, 9H), 3.60 (m, 1H), 3.90 (m, 2H), 4.46 (m, 2H), 5.75 (m, 2H), 6.62 (m, 2H), 6.98 (d, J=3.9 Hz, 1H), 7.46 (d, J=3.9 Hz, 1H), 7.52 (m, 2H), 8.87 (t, J=7.4 Hz, 1H), 8.52 (m, 1H), 11.53 (m, 1H).

(S)-2-Benzenesulfonylamino-3-{[5-(3-guanidino-(Z)-propenyl)-thiophene-2-carbonyl]-amino)-propionic acid, trifluoroacetic acid salt (Q-2).

To a solution of compound Q-1 (5.0 mg, 0.007 mmol) in 1.5 mL of anhydrous dichloromethane was added 1.5 mL of trifluoroacetic acid. After stirring at room temperature for 12 hours, the solvent was evaporated. The residue was then triturated with diethyl ether and dissolved in methanol. Evaporation of the solvent gave 5.0 mg (quantitative yield) of compound Q-2 as a white powder.

$^1$H NMR (400 MHz, CD$_3$OD) d 3.51 (m, 1H), 3.71 (dd, J=13.5, 5.0 Hz, 1H), 4.05 (dd, J=8.2, 5.0 Hz, 1H), 4.23 (dd, J=6.4, 1.8 Hz, 2H), 5.76 (m, 1H), 6.80 (m, 1H), 7.10 (d, J=3.9 Hz, 1H), 7.45–7.58 (m, 4H), 7.85 (m, 2H).

SCHEME R

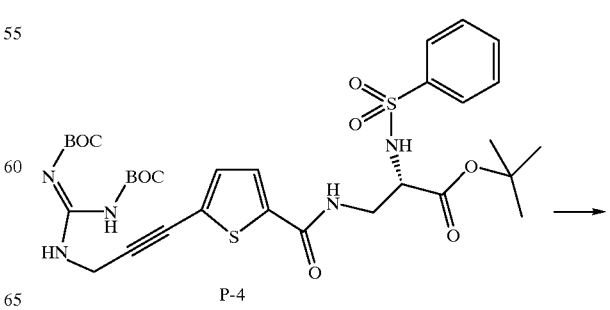

P-4

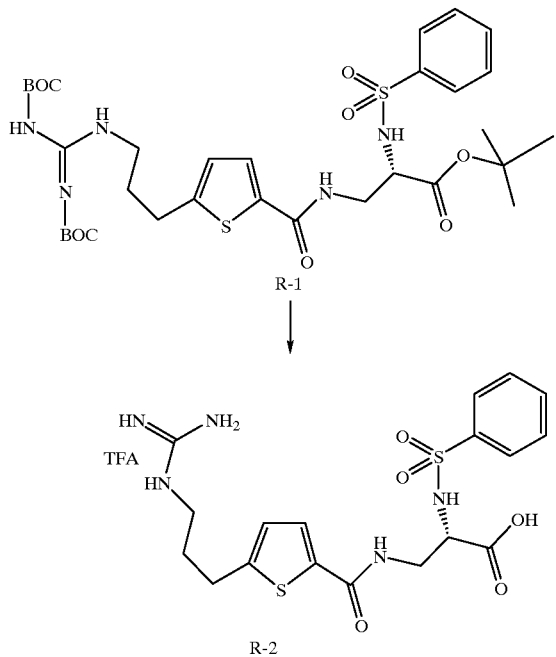

(S)-2-Benzenesulfonylamino-3-{[5-(3-(N,N-Bis-BOC-guanidino)-propyl)-thiophene-2-carbonyl]-amino}-propionic acid tert-butyl ester (R-1).

To a solution of compound P-4 (0.026 g, 0.037 mmol) in 0.5 mL of anhydrous methanol was added the 10% palladium/charcoal (0.026 g). The resulting mixture was stirred for 4 hrs at room temperature under an hydrogen atmosphere. This was followed by filtration of the mixture and evaporation of the solvent. Purification of the residue by flash chromatography (toluene 70%:ethyl acetate 30%) provided 0.014 g (52% yield) of compound R-1 as a clear oil.

$^1$H NMR (400 MHz, CDCl$_3$) d 1.31 (s, 9H), 1.52 (s, 9H), 1.53 (s, 9H), 2.00 (t, J=7.3 Hz, 2H), 2.92 (t, J=7.5 Hz, 2H), 3.57 (m, 3H), 3.90 (m, 2H), 5.71 (d, J=7.2 Hz, 1H), 6.55 (m, 1H), 6.84 (d, J=3.7 Hz, 1H), 7.39 (d, J=3.7 Hz, 1H), 7.52 (m, 2H), 7.59 (m, 1H), 7.88 (m, 2H), 8.54 (m, 1H), 11.52 (m, 1H).

(S)-2-Benzenesulfonylamino-3-{[5-(3-guanidino-propyl)-thiophene-2-carbonyl]-amino}-propionic acid, trifluoroacetic acid salt (R-2).

To a solution of compound R-1 (0.009 g, 0.013 mmol) in 0.85 mL of anhydrous dichloromethane was added 0.85 mL of trifluoroacetic acid. The resulting mixture was stirred for 4.5 hours at room temperature and the solvent was then evaporated. The residue was triturated with diethyl ether and dissolved in methanol. Evaporation of the solvent gave 7.2 mg (quantitative yield) of compound R-2 as a white powder.

$^1$H NMR (400 MHz, CD$_3$OD) d 2.00 (m, 2H), 2.96 (t, J=7.5 Hz, 2H), 3.26 (t, J=7.0 Hz, 2H), 3.48 (m, 1H), 3.70 (m, 1H), 4.19 (dd, J=8.4, 4.9 Hz, 1H), 6.89 (d, J=3.7 Hz, 1H), 7.46 (m, 4H), 7.83 (m, 2H)

SCHEME S

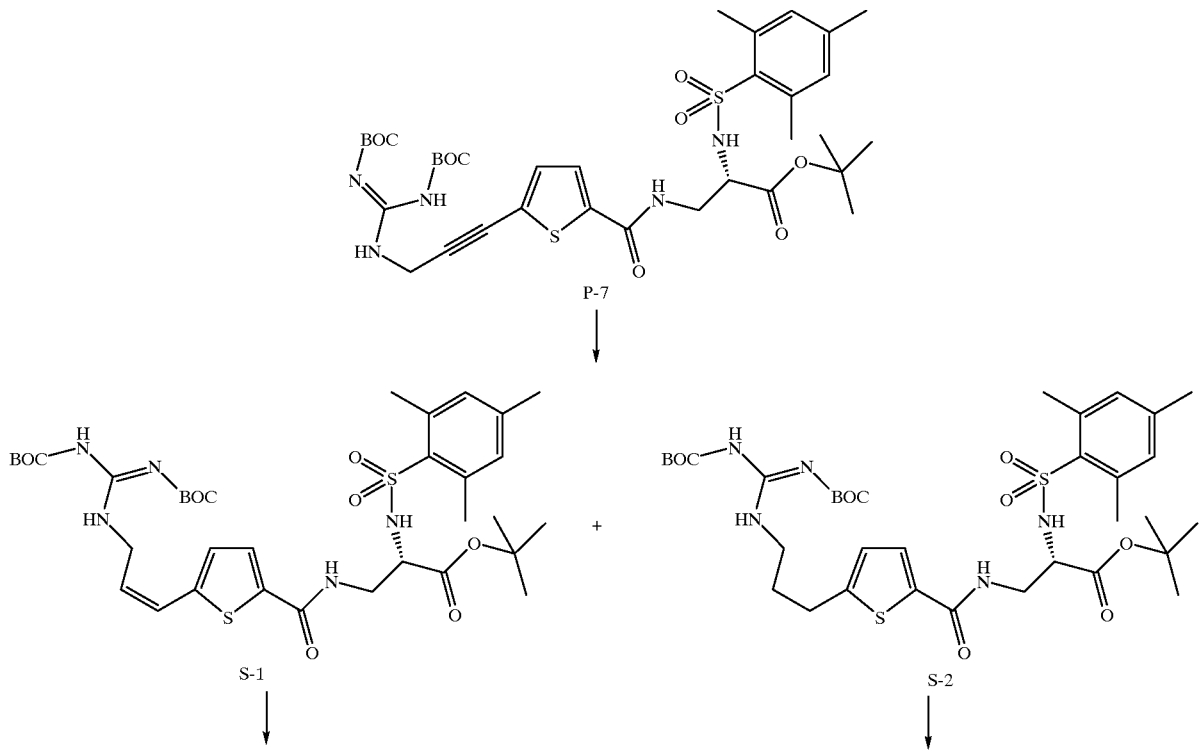

-continued

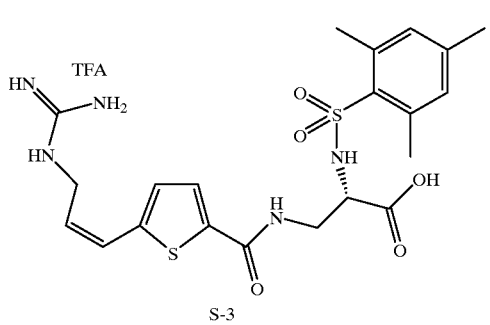
S-3

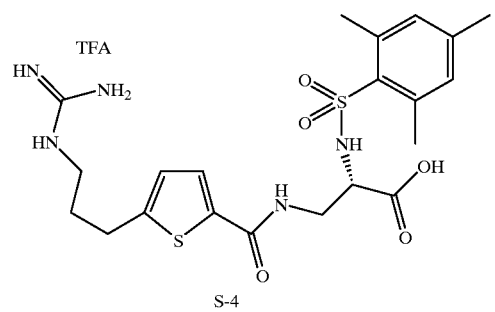
S-4

(S)-3-{[5-(3-(N,N-Bis-BOC-Guanidino)-(Z)-propenyl)-thiophene-2-carbonyl]-amino}-2-(2,4,6-trimethyl-benzenesulfonylamino)-propionic acid tert-butyl ester (S-1) and (S)-3-{[5-(3-(N,N-Bis-BOC-Guanidino)-propyl)-thiophene-2-carbonyl]-amino}-2-(2,4,6-trimethyl-benzenesulfonylamino)-propionic acid tert-butyl ester (S-2).

To a solution of compound P-7 (0.064 g, 0.086 mmol) in 2 mL of anhydrous tetrahydrofuran was added 5% palladium/charcoal (0.0193 g), three drops of thiophene and ethanol (1 mL). The resulting mixture was stirred for 40 minutes at room temperature under an hydrogen atmosphere. This was followed by the filtration of the mixture and evaporation of the solvent. Purification of the residue by flash chromatography (toluene 80%:ethyl acetate 20%) gave 8.8 mg (14% yield) of compound S-1 as a clear oil.

$^1$H NMR (400 MHz, CDCl$_3$) d 1.34 (s, 9H), 1.52 (s, 9H), 1.53 (s, 9H), 2.29 (m, 2H), 2.29 (s, 3H), 2.66 (s, 6H), 3.59 (m, 1H), 3.86 (m, 2H), 4.47 (d, J=5.1 Hz, 2H), 5.77 (m, 2H), 6.61 (d, J=11.8 Hz, 1H), 6.66 (m, 1H), 6.96 (s, 2H), 6.98 (d, J=3.8 Hz, 1H), 7.45 (d, J=3.8 Hz, 1H), 8.53 (m, 1H), 11.54 (m, 1H).

A second fraction contained 8.3 mg (13 % yield) of compound S-2 as a clear oil.

$^1$H NMR (400 MHz, CDCl$_3$) d 1.33 9s, 9H), 1.52 (s, 9H), 1.53 (s, 9H), 2.00 (m, 2H), 2.29 (s, 3H), 2.66 (s, 6H), 2.92 (t, J=7.6 Hz, 2H), 3.57 (m, 3H), 3.81 (m, 2H), 5.75 (d, J=7.0 Hz, 1H), 6.56 (d, J=5.6 Hz, 1H), 6.84 (d, J=3.7 Hz, 1H), 6.96 (s, 2H), 7.37 (d, J=3.7 Hz, 1H), 8.50 (m, 1H), 11.53 (m, 1H).

(S)-3-{[5-(3-Guanidino-(Z)-propenyl)-thiophene-2-carbonyl]-amino}-2-(2,4,6-trimethyl-benzenesulfonylamino)-propionic acid, trifluoroacetic acid salt (S-3).

To a solution of compound S-1 (8.8 mg, 0.012 mmol) in 1.5 mL of anhydrous dichloromethane was added 1.5 mL of trifluoroacetic acid. After the mixture was stirred overnight at room temperature, the solvents were evaporated. The residue was then triturated with diethyl ether and dissolved in methanol. Evaporation of the solvent gave 4.9 mg (69% yield) of compound S-3 as a white powder.

$^1$H NMR (400 MHz, CD$_3$OD) d 2.19 (s, 3H), 2.61 (s, 6H), 3.45 (m, 1H), 3.73 (m, 1H), 4.12 (m, 1H), 4.23 (m, 2H), 5.77 (m, 1H), 6.80 (d, J=11.8 Hz, 1H), 6.86 (s, 2H), 7.09 (d, J=3.9 Hz, 1H), 7.48 (d, J=3.9 Hz, 1H).

(S)-3-{[5-(3-Guanidino-propyl)-thiophene-2-carbonyl]-amino}-2-(2,4,6-trimethyl-benzenesulfonylamino)-propionic acid, trifluoroacetic acid salt (S-4).

To a solution of compound S-2 (0.0083 g, 0.011 mmol) in 1.5 mL of anhydrous dichloromethane was added 1.5 mL of trifluoroacetic acid. After the mixture was stirred overnight, the solvents were evaporated. The residue was then triturated with diethyl ether and dissolved in methanol. Evaporation of the solvent gave 5.7 mg (85 % yield) of compound S-4 as a white powder.

$^1$H NMR (400 MHz, CD$_3$OD) d 2.00 (m, 2H), 2.23 (s, 3H), 2.62 (s, 6H), 2.96 (t, J=7.6 Hz, 2H), 3.26 (t, J=7.0 Hz, 2H), 3.46 (m, 1H), 3.67 (m, 1H), 4.00 (m, 1H), 6.88 (d, J=3.8 Hz, 1H), 6.89 (s, 2H), 7.39 (d, J=3.7 Hz, 1H).

SCHEME T

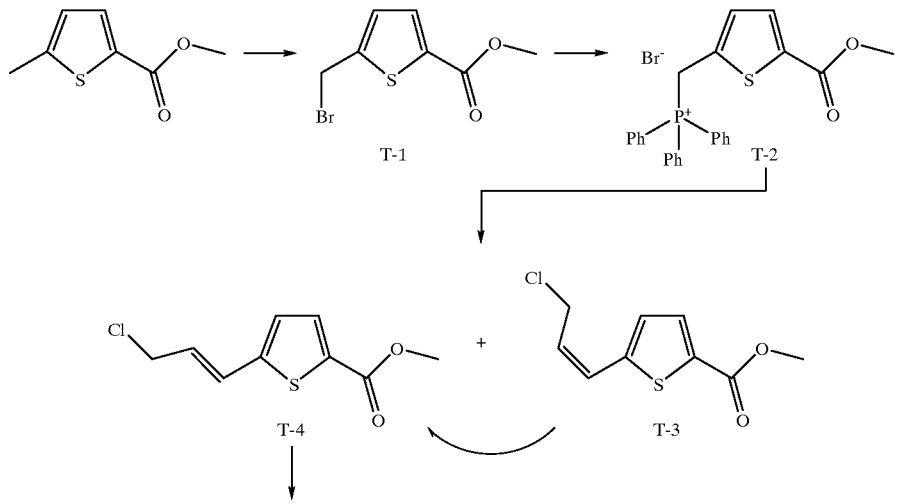

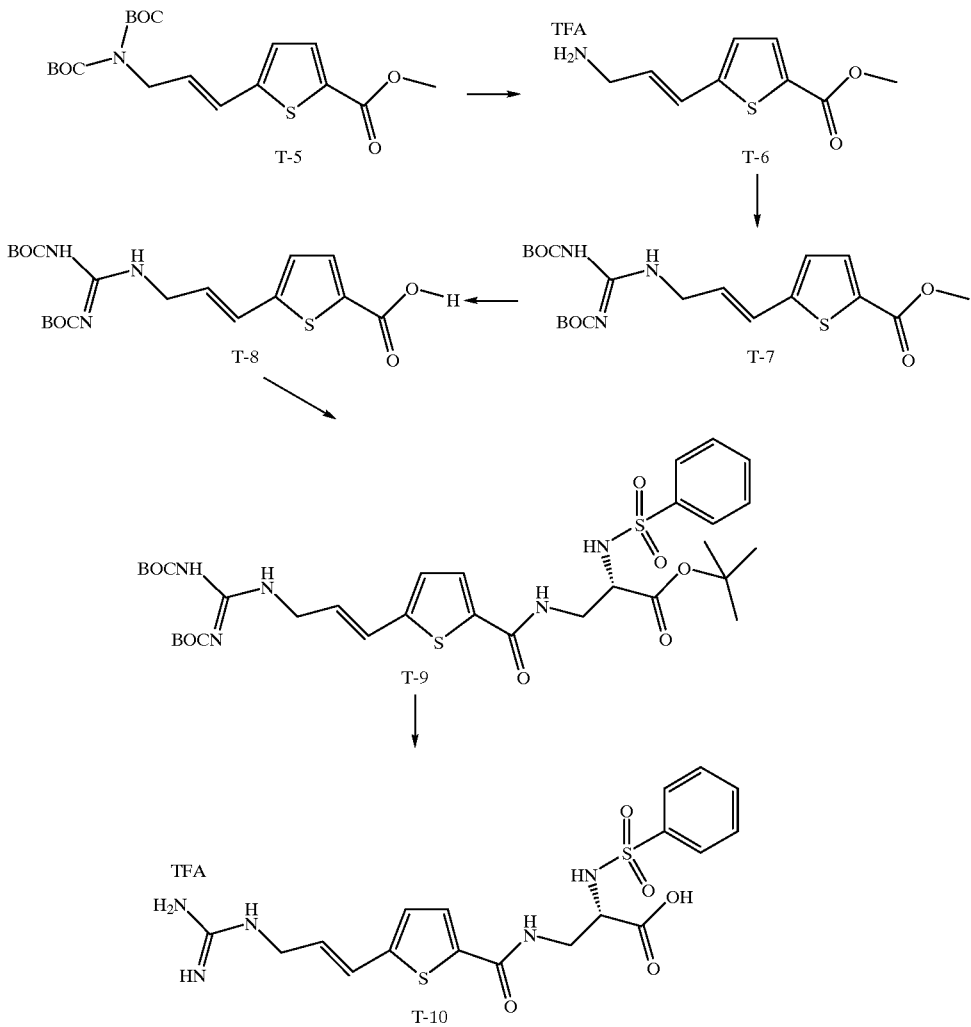

Preparation of 5-Bromomethyl-thiophene-2-carboxylic acid methyl ester (T-1).

5-Methyl-thiophene-2-carboxylic acid methyl ester (20.0 g, 0.13 mol) was dissolved in a suspension of N-bromosuccinimide (45.4 g, 0.26 mol) and 2,2'-aza-bis-isobutyronitrile (0.1 g, 0.61 mmol) in 1 L of carbon tetrachloride. The suspension was refluxed for 48 hours then cooled and the precipitate was filtered off. The filtrate was concentrated and the residue was purified on silica gel (100% hexanes then 9:1 Hexanes-Ethyl acetate) to provide a 26 g fraction containing mainly the di-brominated compound 5-dibromomethyl-thiophene-2-carboxylic acid methyl ester as a yellow oil and a more polar fraction (7.5 g) containing mainly compound T-1 (25% yield) as a yellow oil (70% purity).

$^1$H NMR (400 MHz, CDCl$_3$) d 3.90 (s, 3H), 4.69 (s, 2H), 7.11 (d, J=3.8 Hz, 1H), 7.65 (d, J=3.8 Hz, 1H).

Preparation of (5-Methoxycarbonyl-thiophen-2-ylmethyl)-triphenylphosphonium bromide (T-2).

Compound T-1 (7.6 g, 0.03 mol) was dissolved in 700 mL of anhydrous dichloromethane along with triphenylphosphine (12.7 g, 0.05 mol). The resulting solution was stirred at room temperature overnight then anhydrous diethyl ether was added and the precipitate was filtered and washed with more diethyl ether. The resulting solid was dried under vacuum to provide 8.7 g (64% yield) of compound T-2 as a white powder.

$^1$H NMR (400 MHz, DMSO-d6) d 3.76 (s, 3H), 5.68 (d, J=15.4 Hz, 2H), 6.84 (t, J=3.6 Hz, 1H), 7.64 (d, J=3.6 Hz, 1H), 7.71–7.8 (m, 12H), 7.92–7.96 (m, 3H).

Preparation of 5-(3-chloro-(Z)-propenyl)-thiophene-2-carboxylic acid methyl ester (T-3) and 5-(3-chloro-(E)-propenyl)-thiophene-2-carboxylic acid methyl ester (T-4).

A 1 M solution of lithium hexamethyl disilazane (6.6 mL, 6.6 mmol) in tetrahydrofuran was added slowly to a suspension of compound T-2 (2.9 g, 5.5 mmol) in 250 mL of anhydrous tetrahydrofuran (during the addition the reaction mixture went from a cloudy white to bright red). Upon completion of the addition the reaction mixture was left stirring at room temperature for 1 hour. During this time a solution of chloroacetaldehyde in dichloromethane was prepared by extraction of 100 mL of 50% aqueous chloroacetaldehyde with 300 mL dichloromethane then again with 200 mL dichloromethane the organic phases were combined then dried 1 hour over anhydrous magnesium sulfate then filtrated. This chloroacetaldehyde solution in dichloromethane was then rapidly added to the reaction mixture above until discoloration of the red solution. The reaction mixture was partitioned between water and dichloromethane, the layers were separated, the organic layer was washed with diluted hydrochloridric acid (100 mL, 0.01 M) then concentrated. The residue was purified by performing two sequential columns (95:5 hexanes-ethyl acetate) to provide 680 mg of mainly compound T-3 (88:12 Z:E) and 130 mg of compound (T-4)(95:5 E:Z) for a combined yield of 68%. Compound T-3 (yellow oil):

$^1$H NMR (400 MHz, CDCl3) d 3.92 (s, 3H), 4.41 (d, J=8.0 Hz, 2H), 5.97 (dt, J=8.0, 11.4 Hz, 1H), 6.67 (d, J=11.4 Hz, 1H), 7.07 (d, J=3.9 Hz, 1H), 7.74 (d, J=3.9 Hz, 1H). Compound T-4 (yellow oil):

$^1$H NMR (400 MHz, CDCl3) d 3.90 (S, 3H), 4.23 (d, J=7.0 Hz, 2H), 6.31 (dt, J=7.0, 15.5 Hz, 1H), 6.78 (d, J=15.5 Hz, 1H), 7.0 (d, J=3.9 Hz, 1H), 7.68 (d, J=3.9 Hz, 1H).

Preparation of 5-(3-Chloro-(E)-propenyl)-thiophene-2-carboxylic acid methyl ester (T-4) from 5-(3-chloro-(Z)-propenyl)-thiophene-2-carboxylic acid methyl ester (T-3).

An isomeric mixture containing mainly compound T-3 (650 mg, 3.0 mmol) was dissolved in 50 mL of chloroform (50.0 mL) along with iodine (600 mg, 2.4 mmol). The resulting dark violet solution was stirred at room temperature overnight. Aliquots of the reaction mixture could be checked by NMR to determine end point. Upon completion of the equilibration a solution of sodium bisulfite was added to the reaction mixture which turned clear. The organic layer was separated, dried (MgSO$_4$), filtered, and the filtrate was concentrated to provide 650 mg (100% yield) of compound T-4 as a yellow to orange oil.

$^1$H NMR (400 MHz, CDCl3) d 3.90 (s, 3H), 4.23 (d, J=7.0 Hz, 2H), 6.31 (dt, J=7.0, 15.5 Hz, 1H), 6.78 (d, J=15.5 Hz, 1H), 7.0 (d, J=3.9 Hz, 1H), 7.68 (d, J=3.9 Hz, 1H).

Preparation of 5-(3-bis-(tert-Butoxycarbonyl)amino-(E)-propenyl)-thiophene-2-carboxylic acid methyl ester (T-5).

To a solution of di-tert-butyl imino-dicarboxylate (784 mg, 3.6 mmol) in anhydrous dimethylformamide (6.0 mL) was added sodium hydride (60% in oil, 87 mg, 3.6 mmol) in one portion. The resulting mixture was stirred for 10 minutes and then compound T-4 (650 mg, 3.0 mmol) in anhydrous tetrahydrofuran (6 mL) was added in one portion. The reaction mixture turned dark brown with clumps and was left stirring overnight at room temperature. It was then concentrated and the residue was partitioned between ethyl acetate and water. The layers were separated and the organic layer was washed with aqueous ammonium chloride, dried (MgSO$_4$), filtered, and the filtrate was concentrated to provide 750 mg (63% yield) of compound T-5 as a clear yellow oil.

$^1$H NMR (400 MHz, CDCl3) d 1.53 (s, 18H), 3.89 (s, 3H), 4.33 (dd, J=1.1, 16.0 Hz, 2H), 6.22 (dt, J=6.1, 15.7 Hz, 1H), 6.63 (d, J=15.7 Hz, 1H), 6.94 (d, J=3.9 Hz, 1H), 7.66 (d, J=3.9 Hz, 1H).

Preparation of 5-(3-amino-(E)-propenyli-thiophene-2-carboxylic acid methyl ester trifluoroacetic acid salt (T-6).

Compound T-5 was dissolved in anhydrous dichloromethane (18.8 mL). Trifluoroacetic acid (18.8 mL) was added to the reaction mixture which was left stirring at room temperature overnight. The reaction mixture was then concentrated and the residue was triturated twice with anhydrous diethyl ether, separated then dried under vacuum to provide 580 mg (99% yield) of compound T-6 as an off-white powder.

$^1$H NMR (400 MHz, CD$_3$OD) d 3.74 (d, J=6.8 Hz, 2H), 3.89 (s, 3H), 6.28 (dt, J=6.8, 15.8 Hz, 1H), 7.00 (d, J=15.8 Hz, 1H), 7.17 (d, J=4.0 Hz, 1H), 7.71 (d, J=4.0 Hz, 1H).

5-(3-N,N-Bis-BOC-guanidino-(E)-propenyl)-thiophene-2-carboxylic acid methyl ester (T-7).

Compound T-6 (580 mg, 1.86 mmol) was dissolved in anhydrous acetonitrile (15.0 mL), with 1H-pyrazole-1-bis-(tert-butylcarboxy)-carboxamidine (607 mg, 1.96 mmol). Triethylamine (1 mL) was then added to the reaction mixture that was then left stirring at room temperature for 2.5 days. The reaction mixture was concentrated and the residue was purified on silica gel (95:5, hexanes:ethyl acetate) to provide 550 mg of compound T-7 as a pale yellow sticky solid.

$^1$H NMR (400 MHz, CDCl$_3$) d 1.53 (s, 9H), 1.54(s, 9H), 3.90 (s, 3H), 2.05 (m, 2H), 6.23 (dt, J=6.1, 15.7 Hz, 1H), 6.65 (d, J=15.8 Hz, 1H), 6.96 (d, J=3.9 Hz, 1H), 7.67 (d, J=3.9 Hz, 1H), 8.50 (s, 1H), 11.56 (s, 1H).

5-(3-big(tert-Butylcarbonyl)guanidino-(E)-propenyl)-thiophene-2-carboxylic acid (T-8).

To a solution of compound T-7 (525 mg, 1.2 mmol) in tetrahydrofuran (30 mL) was added a solution of lithium hydroxyde monohydrate (258 mg, 6.0 mmol) in water (60 mL). The reaction mixture became homogeneous and was left stirring at room temperature overnight. The tetrahydrofuran was evaporated under reduced pressure at room temperature and the resulting aqueous suspension was acidified and then extracted rapidly with ethyl acetate. The organic layer was washed with distilled water separated, dried (MgSO$_4$) and evaporated to provide 466 mg of compound T-8 as a yellow solid.

$^1$H NMR (400 MHz, CDCl$_3$) d 1.53 (s, 18H), 4.27 (t, J=5.0 Hz, 1H), 6.26 (d, J=15.8 Hz, 1H), 6.65 (d, J=15.8 Hz, 1H), 6.98 (d, J=3.9 Hz, 1H), 7.77 (d, J=3.9 Hz, 1H), 8.7 (s, 1H).

(S)-2-Benzenesulfonylamino-3-{[5-(3-N,N-Bis-BOC-guanidino-(E)-propenyl)-thiophene-2-carbonyl]-amino}-propionic acid tert-butyl ester (T-9).

Compound T-8 (40 mg, 0.09 mmol) was dissolved in anhydrous N,N-dimethylformamide (2.0 mL), with triethylamine (0.1 mL) and (S)-3-Amino-2-benzenesulfonylamino-propionic acid tert-butyl ester hydrochloride salt (45.4 mg, 0.14 mmol). O-(7-azabenzotriazol-1-yl)-N,N,N',N'-tetramethyluronium-hexafluorophosphate (51.3 mg, 0.14 mmol) was then added to this solution at room temperature in one portion. The reaction mixture was left stirring overnight and was then concentrated. The resulting residue was purified on silica gel (7:3, hexanes:ethyl acetate then 3:2, hexanes:ethyl acetate) to afford 47 mg (72% yield) of compound T-9 as a clear oil.

$^1$H NMR (400 MHz, CDCl$_3$) d 1.31 (s, 9H), 1.52 (s, 9H), 1.53 (s, 9H), 3.57 (m, 1H), 3.90 (m, 2H), 4.25 (dd, J=0.9, 6.2 Hz, 2H), 5.70 (d, J=7.2 Hz, 1H), 6.21 (dt, J=6.1, 15.8 Hz, 1H), 6.59 (t, J=5.3 Hz, 1H), 6.64 (d, J=15.8 Hz, 1H), 6.93 (d, J=3.9 Hz, 1H), 7.41 (d, J=3.9 Hz, 1H), 7.51 (m, 2H), 7.59 (m, 1H), 7.86 (m, 2H), 8.49 (bm, 1H), 11.56 (s, 1H).

(S)-2-Benzenesulfonylamino-3-{[5-(3-guanidino-(E)-propenyl)-thiophene-2-carbonyl]-amino}-propionic acid trifluoroacetic acid salt (T-10).

Compound T-9 (40 mg, 0.06 mmol) was dissolved in anhydrous dichloromethane (1.0 mL). Trifluoroacetic acid (1.0 mL) was added to the reaction mixture which was then stirred overnight at room temperature. The resulting mixture was concentrated and the residue was triturated in anhydrous diethyl ether and the resulting white powder was dried under vacuum providing 29.5 mg (92% yield) of compound T-10 as a white powder.

$^1$H NMR (400 MHz, CD$_3$OD) d 3.49 (m, 1H), 3.71 (dd, J=5.0, 13.6 Hz, 1H), 4.00 (dd, J=1.4, 5.7 Hz, 2H), 4.17 (dd, J=5.1, 8.5 Hz, 1H), 6.23 (dt, J=5.7, 15.8 Hz, 1H), 6.79 (d, J=15.8 Hz, 1H), 7.05 (d, J=3.9 Hz, 1H), 7.49 (m, 4H), 7.84 (m, 2H).

SCHEME U

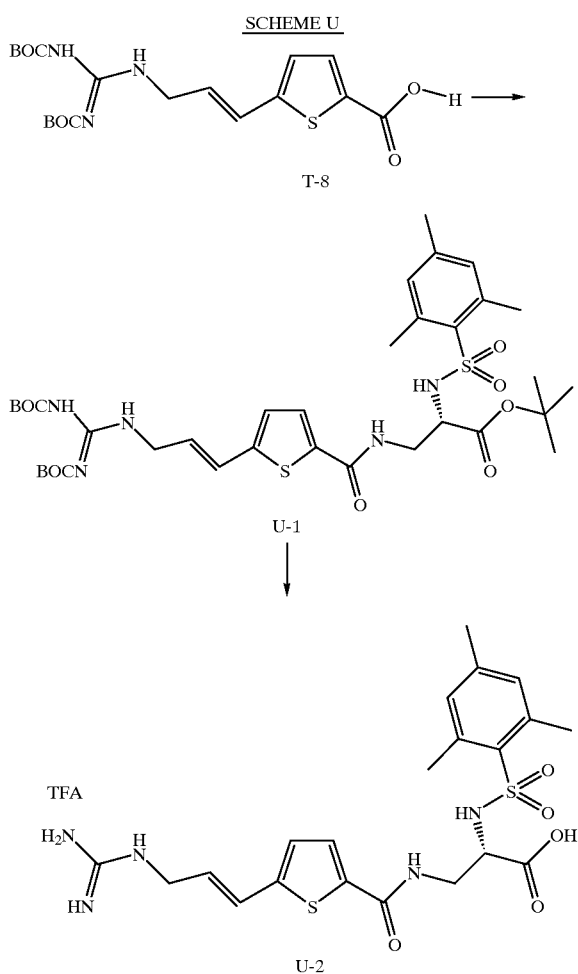

(S)-3-{[5-(3-N,N-Bis-BOC-guanidino-(E)-propenyl)-thiophene-2-carbonyl]-amino}-2-(2,4,6-trimethyl-benzenesulfonylamino)-propionic acid tert-butyl ester (U-1).

Compound T-8 (50 mg, 0.11 mmol) was dissolved in anhydrous N,N-dimethylformamide (2.0 mL), with triethylamine (0.1 mL) and (S)-3-amino-2-(2,4,6-trimethyl-benzenesulfonylamino)-propionic acid tert-butyl ester hydrochloride salt (64 mg, 0.17 mmol). O-(7-azabenzotriazol-1-yl)-N,N,N',N'-tetramethyluronium exafluorophosphate (64 mg, 0.17 mmol) was then added to this solution at room temperature in one portion. The reaction mixture was left stirring overnight. The reaction mixture was concentrated and the resulting residue was partitioned between water and ethyl acetate. The organic layer was separated, washed with diluted citric acid, water and saturated sodium bicarbonate solution, dried (MgSO$_4$), filtered and concentrated. The resulting residue was purified on silica gel (4:1, hexanes:ethyl acetate then 3:1, hexanes:ethyl acetate) to afford 67 mg (80% yield) of compound U-1 as a clear oil.

$^1$H NMR (400 MHz, CDCl$_3$) d 1.32 (s, 9H), 1.52 (s, 9H), 1.53 (s, 9H), 2.29 (s, 3H), 2.66 (s, 6H), 3.57 (m, 1H), 3.79 (m, 2H), 4.25 (t, J=5.3 Hz, 2H), 5.76 (d, J=7.1 Hz, 1H), 6.19 (dt, J=5.3, 15.7 Hz, 1H), 6.63 (m, 2H), 6.93 (d, J=3.8Hz, 1H), 6.95 (s, 2H), 7.40 (d, J=3.8Hz, 1H),(s, 1H), 8.52 (m, 1H), 11.60 (s, 1H).

(S)-3-{[5-(3-Guanidino-(E)-propenyl)-thiophene-2-carbonyl]-amino}-2-(2,4,6-trimethyl-benzenesulfonylamino)-propionic acid trifluoroacetic acid salts (U-2).

Compound U-1 (62 mg, 0.08 mmol) was dissolved in anhydrous dichloromethane (1.0 mL). Trifluoroacetic acid (1.0 mL) was added to the reaction mixture which was then stirred overnight. The reaction mixture was concentrated and the resulting residue was triturated in anhydrous diethyl ether and the resulting white powder was dried under vacuum providing 45 mg (90% yield) of compound U-2 as a white powder.

$^1$H NMR (400 MHz, CD$_3$OD) d 2.20 (s, 3H), 2.61 (s, 6H), 3.47 (m, 1H), 3.69 (dd, J=4.6, 13.3 Hz, 1H), 4.00 (m, 3H), 6.22 (dt, J=5.5,15.6 Hz 1H), 6.79 (d, J=15.6 Hz, 1H), 6.87 (s, 2H), 7.04 (d, J=3.9 Hz, 1H), 7.40 (d, J=3.9 Hz, 1H).

SCHEME V

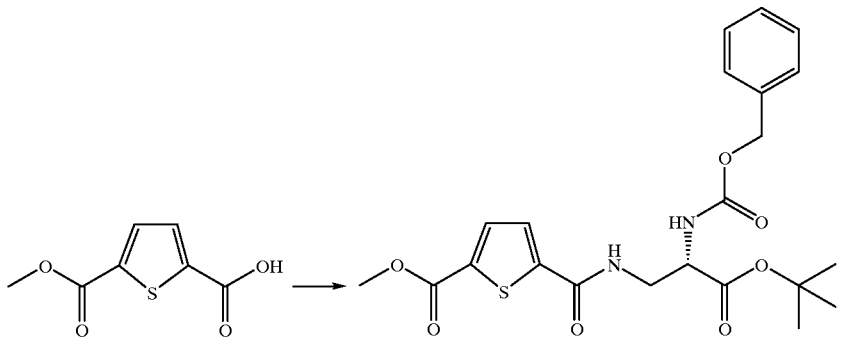

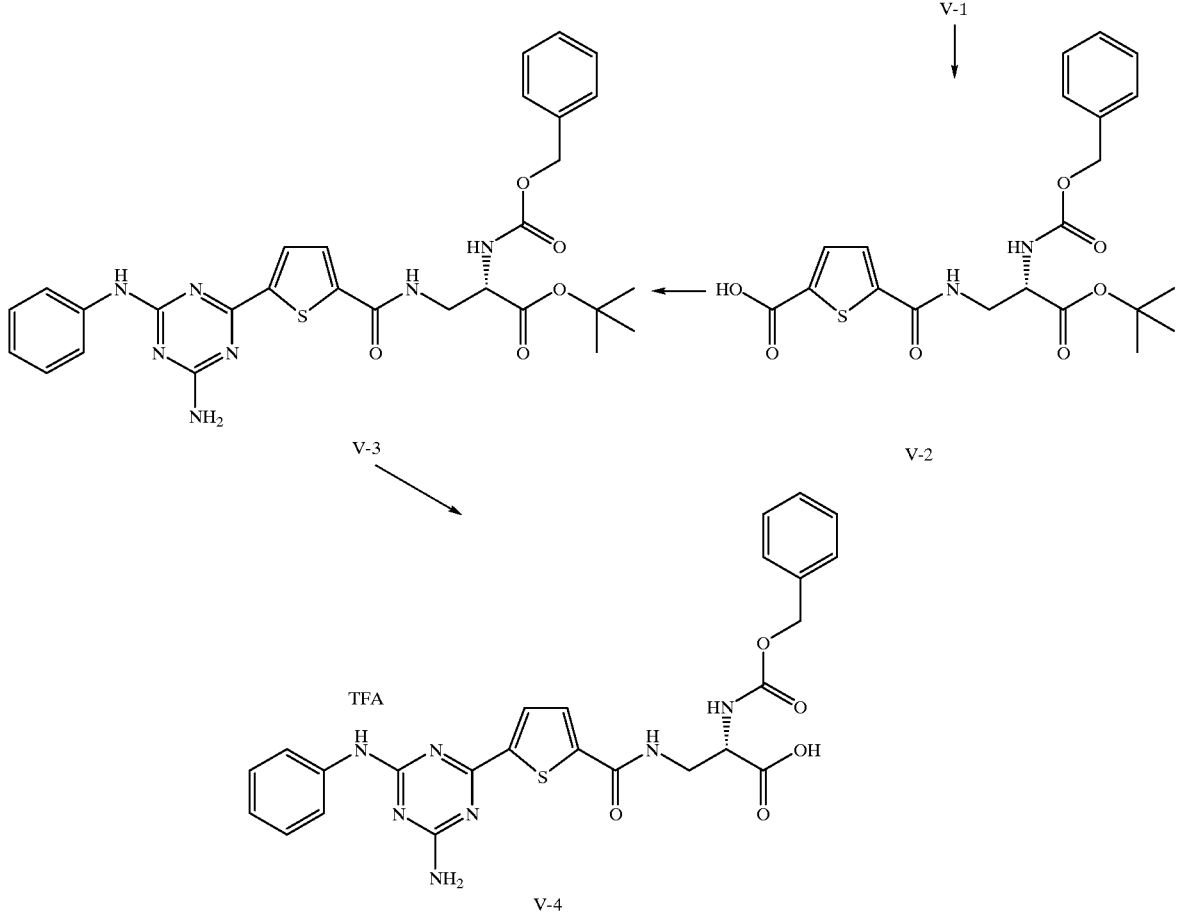

5-(2-(S)-Benzyloxycarbonylamino-2-tert-butoxycarbonyl-ethylcarbamoyl)-thiophene-2-carboxylic acid methyl ester (V-1).

Thiophene-2,5-dicarboxylic acid monomethyl ester (858 mg, 4.53 mmol), 2-(S)-Benzyloxycarbonyl-amino-2-tert-butoxycarbonyl-ethyl-ammonium chloride (1.50 g, 4.53 mmol) and N-methylmorpholine (2.00 mL, 18.2 mmol) were dissolved in 25 mL of anhydrous N,N-dimethylformamide. O-(7-Azabenzotriazol-1-yl)-N,N,N',N'-tetramethyluronium hexafluorophosphate (1.90 g, 4.99 mmol) was added in one portion and the resulting mixture was stirred at room temperature for 20 hours. The solvent was evaporated and a portion of 150 mL of ethyl acetate was added. The resulting organic phase was washed with a 10% aqueous solution of citric acid (2×100 mL), followed by saturated aqueous solution of sodium bicarbonate (2×100 mL) and brine (100 mL). The organic phase was then dried over magnesium sulfate and concentrated. The crude product was purified on silica gel (3:2 hexanes:ethyl acetate) to provide 1.86 g (88% yield) of compound V-1 as a white solid.

$^1$H NMR (400 MHz, CDCl3) d 1.48 (s, 9H) 3.67–3.92 (m, 2H) 3.92 (s, 3H) 4.43–4.48 (m, 1H) 5.11 (d, J=12.4 Hz, 1H) 5.15 (d, J=12.4 Hz, 1H) 5.91–5.93 (m, 1H), 7.24 (bs, 1H) 7.29–7.34 (m, 5H) 7.40 (d, J=3.9 Hz, 1H) 7.70 (d, J=3.8 Hz, 1H) $^{13}$C NMR (100 MHz, CDCl3) 27.8, 43.5, 52.5, 67.3, 83.6, 127.9, 128.0, 128.3, 128.5, 133.3, 135.9, 136.8, 144.2, 157.0, 161.4, 162.1, 168.7.

Preparation of 5-(2-(S)-Benzyloxycarbonylamino-2-tert-butoxycarbonyl-ethylcarbamoyl)-thiophene-2-carboxylic acid (V2).

Lithium hydroxide monohydrate (760 mg, 18.1 mmol) was added to a solution of compound V-1 (8.38 g, 18.1 mmol) in a mixture of tetrahydrofuran and water (115 mL/200 mL). The resulting mixture was stirred for 2.5 hours at room temperature. A portion of 300 mL of ethyl acetate was added followed by 300 mL of a saturated solution of aqueous sodium bicarbonate. The organic phase was recovered, dried with magnesium sulfate and concentrated to afford 1.59 g (19% yield) of starting compound V-1. The aqueous phase was acidified with a 10% aqueous solution of hydrochloric acid and extracted with 500 mL of ethyl acetate. This organic phase was then washed with brine and concentrated to provide 4.73 g of compound V-2 as a white solid.

$^1$H NMR (400 MHz, CDCl3) d 1.33 (s, 9H) 3.58 (t, J=6.1 Hz, 2H) 4.23 (dd, J=14.6, 6.5 Hz, 1H) 5.03 (d, J=12.6 Hz, 1H) 5.07 (d, J=12.6 Hz, 1H) 7.29–7.40 (m, 5H), 7.63–7.75 (m, 3H) 8.77 (t, J=5.8 Hz, 1H).

Preparation of 3-{[5-(4-Amino-6-phenylamino-[1,3,5]triazin-2-yl)-thiophene-2-carbonyl]-amino}-2-(S)-benzyloxycarbonylamino-propionic acid tert-butyl ester (V-3).

Compound V-2 (100 mg, 0.223 mmol), 1-phenylbiguanidine (43.0 mg, 0.245 mmol) and diisopropylethylamine (117 mL, 0.669 mmol were dissolved together in 1.5 mL of N,N-dimethylformamide. O-(7-Azabenzotriazol-1-yl)-N,N,N',N'-tetramethyluronium hexafluorophosphate (93.0 mg, 0.245 mmol) was added in one portion and the resulting mixture became red. After an overnight stirring at room temperature, the N,N-dimethylformamide was evaporated. The crude residue was diluted in ethyl acetate (50 mL), washed with water (50 mL), then with a saturated solution of sodium bicarbonate (2×50 mL) and brine (50 mL). The organic phase was then dried with magnesium sulfate and concentrated. Flash chromatographies (93:7 dichloromethane:methanol) and (3:2 ethyl acetate:hexanes) provided 74 mg of compound V-3.

$^{1}$H NMR (400 MHz, CDCl3) d 1.48 (s, 9H) 3.82 (bs, 2H) 4.45–4.65 (m, 1H) 5.10 (s, 2H) 5.65–6.40 (bs, 1H) 6.40–6.85 (bs, 1H), 7.08 (t, J=7.3 Hz, 2H) 7.20–7.55 (m, 9H) 7.66 (d, J=6.0 Hz, 2H) 7.70–8.50 (3 broad signals, 2H); $^{13}$C NMR (100 MHz, CDCl3) 27.8, 42.5, 54.7, 67.5, 83.4, 120.5, 123.2, 128.1, 128.2, 128.4, 128.6, 129.0, 130.0, 135.7, 138.5, 141.4, 146.0, 156.1, 156.6, 162.1, 164.1, 166.8, 169.7.

Preparation of 3-{[5-(4-Amino-6-phenylamino-[1,3,5]triazin-2-yl)-thiophene-2-carbonyl]-amino}-2-(S)-benzyloxycarbonylamino-propionic acid, trifluoroacetic acid salt (V-4).

Compound V-3 (72 mg, 0.122 mmol) was dissolved in 0.75 mL of dichloromethane. Trifluoroacetic acid (0.75 mL) was added and the resulting solution was stirred for 15 h at room temperature. The reaction mixture was concentrated to dryness. The crude oil obtained was triturated in ether (4 times), and filtered to give 52 mg (66% yield) of compound V-4 as a yellow powder.

$^{1}$H NMR (400 MHz, DMSO-d6) d 3.47–3.75 (m, 2H) 4.25–4.30 (m, 1H) 5.03 (d, J=12.8 Hz, 1H) 5.07 (d, J=12.7 Hz, 1H) 7.01 (t, J=7.3 Hz, 1H) 7.10–7.45 (m, 9H), 7.64 (d, J=8.2 Hz, 1H) 7.75 (d, J=3.8 Hz, 1H) 7.82 (d, J=8.0 Hz, 2H) 7.87 (d, J=3.7 Hz, 1H) 8.73 (bs, 1H) 9.62 (bs, 1H).

SCHEME W

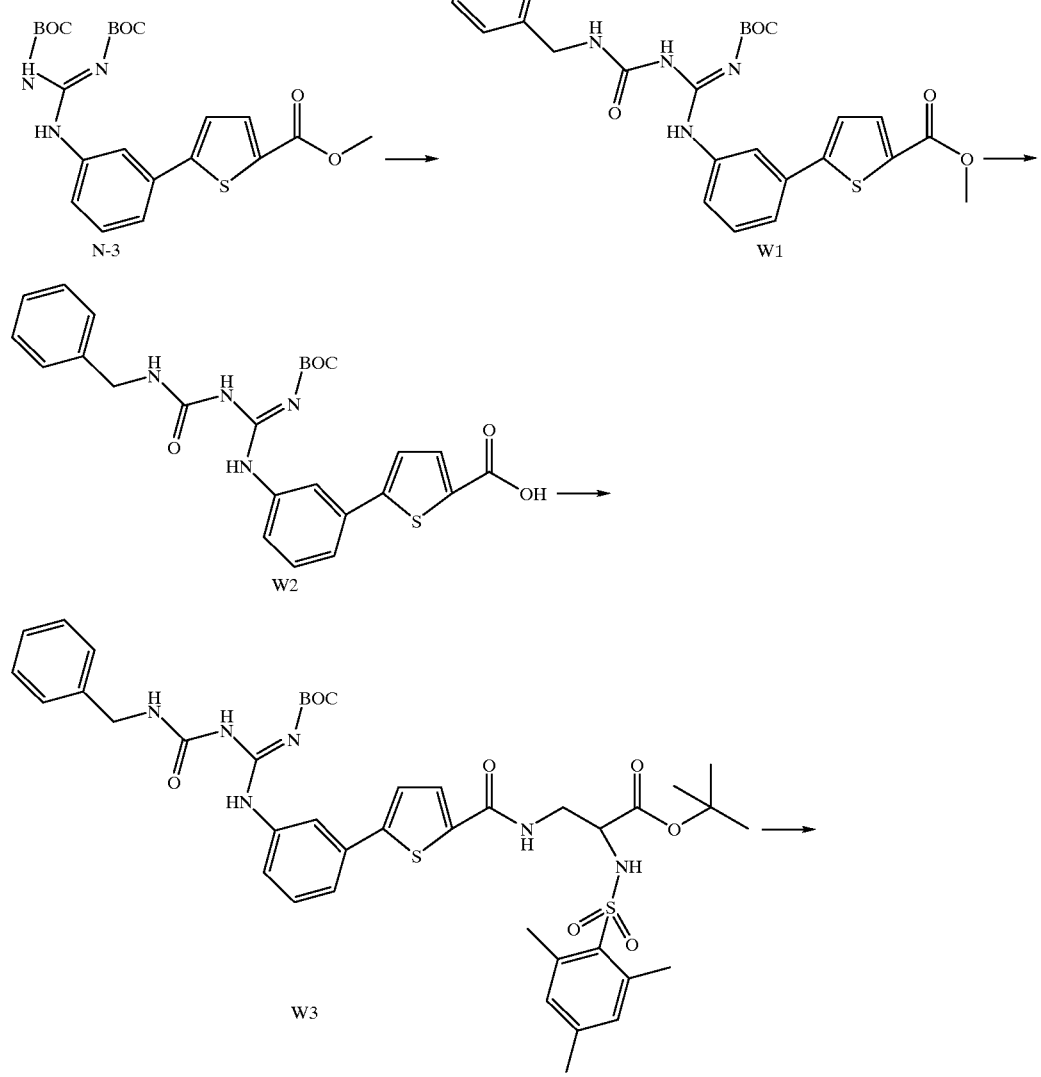

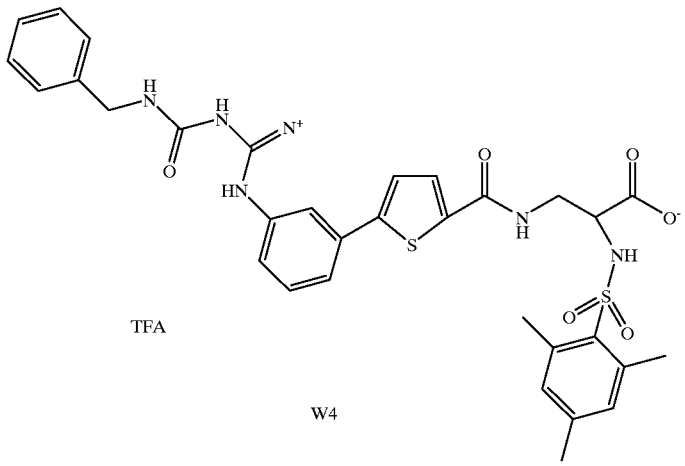

TFA

W4

5-(3-{[(3-Benzyl-ureido)-tert-butoxycarbonylimino-methyl]-amino}-phenyl)-thiophene-2-carboxylic acid methyl ester (W-1).

To a mixture of compound N-3 (50 mg, 0.11 mmol), dimethylaminopyridine (6 mg, 0.042 mmol), DIEA (0.02 ml) in THF or DME (7 mL), was added benzyl amine (0.02 ml, 0.16 mmol). The reaction was refluxed overnight. Solvent was then evaporated under reduced pressure. Purification of the residue on silica gel (1:1 hexanes:EtOAc) gave 47 mg (87% yield) of pure compound W-1.

$^1$HNMR (300 MHz, CDCl3) δ: 1.56 (s, 9H), 3.82 (s, 3H), 4.41 (d, 2H), 7.22–7.40 (m, 8H), 7.61–7.63(m, 1H), 7.77(d, 1H), 7.81 (d, 1H).

5-(3-{[(3-Benzyl-ureido)-tert-butoxycarbonylimino-methyl]-amino}-phenyl)-thiophene-2-carboxylic acid (W-2).

A mixture of compound W-1 (60 mg, 0.12 mmol) and Lithium hydroxide (45 mg, 1.8 mmol) in acetonitrile (5 mL) was stirred for 4 hrs at room temperature. The solvent was removed and the crude reaction product was taken up in ethyl acetate (20 mL). The solution was neutralized with acetic acid (1.0 mL). Solvent was than dried over sodium sulfate and evaporated. Purification of the residue on silica gel (10% MeOH-EtOAc) gave 0.152 g of pure compound W-2 (78% yield).

$^1$HNMR (300 MHz, CD$_3$OD) δ: 1.50 (s, 9H), 4.42 (d, 2H), 7.22–7.81 (m, 11H).

3-{[5-(3-{[(3-Benzyl-ureido)-tert-butoxycarbonylimino-methyl]-amino}-phenyl)-thiophene-2-carbonyl]-amino}-2-(2,4,6-trimethyl-benzenesulfonylamino)-propionic acid tert-butyl ester (W-3).

To a mixture of compound W-2 (45 mg, 0.091 mmol), 3-amino-2-(2,4,6-trimethyl-benzenesulfonylamino)-propionic acid 2-tert-butoxycarbonylamino-ethyl ester (40 mg, 0.093 mmol) and hydroxybenzotriazole (15 mg, 0.11 mmol) in DMF (7 mL) was added 1-(3-dimethylamino)propyl)-3-ethylcarbodiimide hydrochloride (22 mg, 0.11 mmol). The reaction was stirred overnight at room temperature. Insolubles were removed by filtration and the solvent was evaporated. Purification of the residue on silica gel (EtOAc) gave 61 mg of pure compound W-3.

$^1$HNMR (300 MHz, CDCl$_3$) δ: 1.36 (s, 9H), 1.52(s, 9H), 2.22 (s, 3H), 2.63 (s, 6H), 3.52 (m, 1H), 3.71–3.99(m, 2H), 4.42(d, 2H), 5.73 (m, 1H), 5.80(d, 1H), 6.71(m, 1H), 6.95(s, 2H), 7.20–7.45 (m, 8H), 7.46–7.81(m, 3H).

3-{[5-(3-{[(3-Benzyl-ureido)-imino-methyl]-amino}-phenyl)-thiophene-2-carbonyll-amino}-2-(2,4,6-trimethyl-benzenesulfonylamino)-propionic acid (W-4).

Compound W-3 (40 mg, 0.34 mmol) was mixed with a mixture of (1:1)TFA/CH$_2$Cl$_2$ (15 mL) and the reaction mixture was stirred at room temperature overnight. The solvent was evaporated and the residue was tritured with dry ether (2×15 mL). This gave 33 mg (87%) of pure trifluoroacetate salt of compound W-4.

$^1$HNMR (300 MHz, CD$_3$OD) δ: 2.20 (s, 3H), 2.29 (s, 6H), 3.50 (m, 1H), 3.66(m, 1H), 4.02(m, 1H), 4.42(s, 2H), 6.95(s, 2H), 7.24–7.77 (m, 11H).

Scheme X

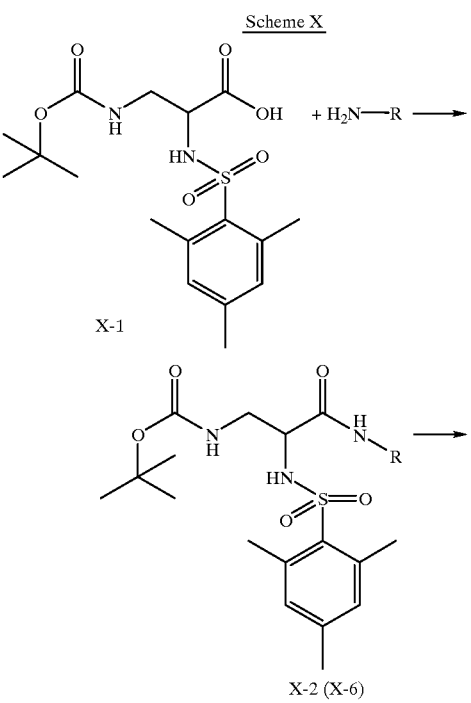

X-1

X-2 (X-6)

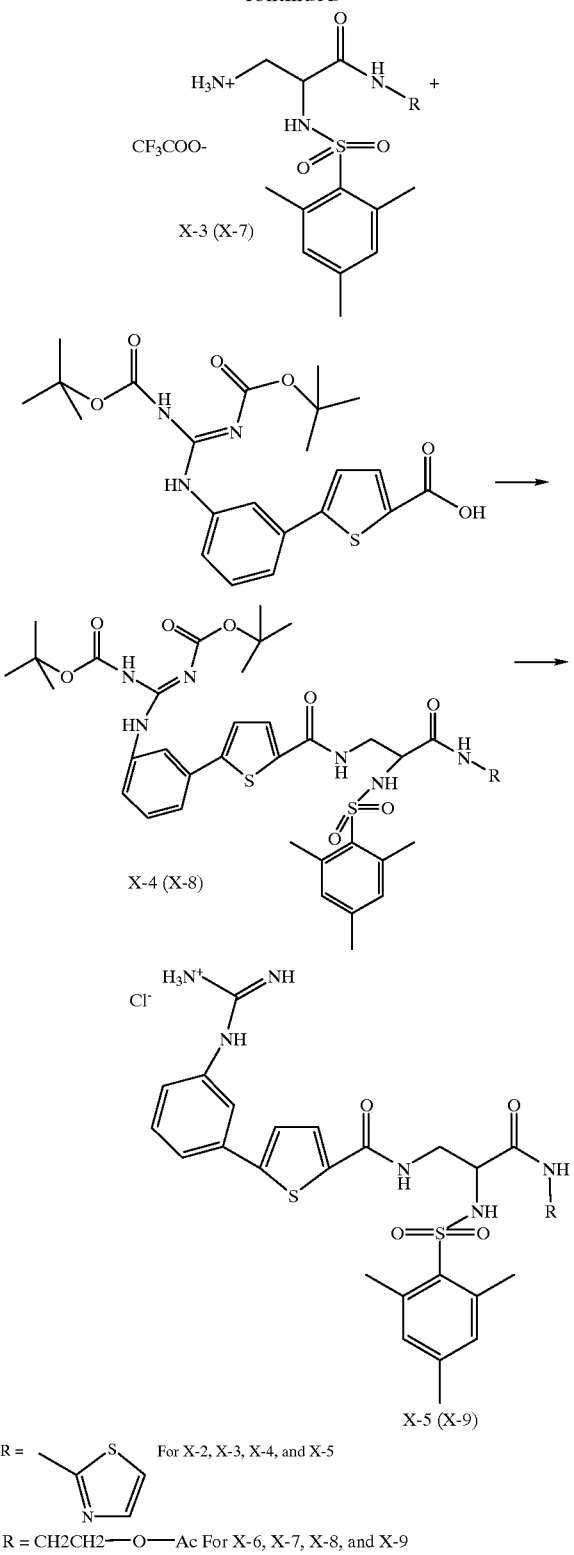

3-tert-Butoxycarbonylamino-2-(2,4,6-trimethyl-benzenesulfonylamino)-propionic acid (X-1).

Procedure: To a solution of 3-Amino-2-(2,4,6-trimethyl-benzenesulfonylamnino)-propionic acid (X-1)(2.65 g, 10.4 mmol) in what is this compound dioxane (20 mL) and water (10 mL) at 0° C. was added sodium hydroxide (1M in water) (10.4 mL, 10.4 mmol) and BOC anhydride (2.49 mg, 11.44 mmol). The mixture was stirred for 4 hours at room temperature then the solution was evaporated to 15 mL. The mixture was diluted in ethyl acetate washed with an aqueous solution of KHSO$_4$ 5%, and then an aqueous solution of HCl 10%, H$_2$O and brine. The organic phases was dry and characterized produce 3g of (X-1) (75% yield).

$^1$HNMR (400 MHz) (CD3OD) δ: 6.97 (s, 2H), 3.95–3.85 (m, 1H), 3.45–3.35 (m, 1H), 3.15–3.05 (m, 1H), 2.62 (s, 6H), 2.23 (s, 3H), 1.40 (s, 9H).

[2-(Thiazol-2-ylcarbamoyl)-2-(2,4,6-trimethyl-benzenesulfonylamino)-ethyl]-carbamic acid tert-butyl ester (X-2).

To a mixture of 3-tert-Butoxycarbonylamino-2-(2,4,6-trimethyl-benzenesulfonylamino)-propionic acid (X-1) (300 mg, 0.77 mmol), 2-aminothiazole(86 mg, 0.85 mmol), DMAP (11 mg, 0.09 mmol) in DMF (30 mL), was added 1-(3-dimethylamino) propyl-3-ethylcarbodiimide hydrochloride (165 mg, 0.86 mmol). The reaction was stirred overnight at room temperature. Insoluble particles were removed by filtration and the solvent was evaporated. Purification of the residue on silica gel (1:4 hexane:EtOAc) gave 217 mg (60%) of pure 2-(Thiazol-2-ylcarbamoyl)-2-(2,4,6-trimethyl-benzenesulfonylamino)-ethyl]-carbamic acid tert-butyl ester.

$^1$HNMR (300 MHz, CDCl$_3$) δ: 1.36 (s, 9H), 2.22 (s, 3H), 2.73 (s, 6H), 3.54 (m, 2H), 4.03(m, 1H), 6.95(s, 2H), 7.03 (d, 1H), 7.58 (d, 1H).

[2-(Thiazol-2-ylcarbamoyl)-2-(2,4,6-trimethyl-benzenesulfonylamino)-ethyl-ammonium trifluoroacetate salt (X-3).

2-(Thiazol-2-ylcarbamoyl)-2-(2,4,6-trimethyl-benzenesulfonylamino)-ethyl]-carbamic acid tert-butyl ester (105 mg, 0.223 mmol) was mixed with a mixture of (1:1) TFA/CH$_2$Cl$_2$ (15 mL) and the reaction mixture was stirred at room temperature overnight. The solvent was evaporated and the residue was tritured with dry ether (2×15 mL). This gave 70 mg (85%) of pure trifluoroacetate salt of 2-(Thiazol-2-ylcarbamoyl)-2-(2,4,6-trimethyl-benzenesulfonylamino)-ethyl-ammonium (X-3).

$^1$HNMR (300 MHz, CD$_3$OD) δ: 2.21 (s, 3H), 2.75 (s, 6H), 3.24 (m, 2H), 4.30(m, 1H), 6.95(s, 2H), 7.22 (d, 1H), 7.48 (d, 1H).

3-{[5-(3-N,N-tert-butoxycarbonylguanidino-phenyl)-thiophene-2-carbonyl]-amino}-2-(2,4,6-trimethyl-benzenesulfonylamino)-2-thiazolo propionamide (X-4).

To a mixture of 5-(3- N,N-ditertbutoxycarbonyl Guanidino-phenyl)-thiophene-2-carboxylic acid (X-3) (88 mg, 0.19 mmol), 2-(Thiazol-2-ylcarbamoyl)-2-(2,4,6-trimethyl-benzenesulfonylamino)-ethyl-amine (70 mg, 0.20 mmol), hydroxybenzotriazole (31 mg, 0.23 mmol) in DMF (30 mL), was added 1-(3-dimethylamino) propyl)-3-ethylcarbodiimide hydrochloride (45 mg, 0.23 mmol). The reaction was stirred overnight at room temperature. Insoluble particles were removed by filtration and the solvent was evaporated. Purification of the residue on silica gel (1:4 hexane:EtOAc) gave 108 mg (71%) of pure 3-{[5-(3-N,N-tert-butoxycarbonylguanidino-phenyl)-thiophene-2-carbonyl]-amino}-2-(2,4,6-trimethyl-benzenesulfonylamino)-2-thiazolo propionamide (X-4).

$^1$HNMR (300 MHz, CDCl$_3$) δ: 1.46(d, 18H), 2.22 (s, 3H), 2.63 (s, 6H), 3.28 (m, 2H), 4.30(m, 1H), 6.95(s, 2H), 7.22–7.83 (m, 8H).

5-(3-Guanidino-phenyl)-thiophene-2-carboxylic acid [2-(thiazol-2-ylcarbamoyl)-2-(2,4,6-trimethyl-benzenesulfonylamino)-ethyl]-amide hydrochloride salt (X-5).

3-{[5-(3-N,N-tert-butoxycarbonylguanidino-phenyl)-thiophene-2-carbonyl]-amino}-2-(2,4,6-trimethylbenzenesulfonylamino)-2-thiazolo propionamide (57 mg, 0.07 mmol) was mixed with a saturated solution of HCl/Ether (25 mL) and the reaction mixture was stirred at room temperature overnight. The solvent was evaporated and the residue was tritured with dry ether (2×25 mL). This gave 35 mg (82%) of pure HCl salt of 5-(3-Guanidino-phenyl)-thiophene-2-carboxylic acid [2-(thiazol-2-ylcarbamoyl)-2-(2,4,6-trimethyl-benzenesulfonylamino)-ethyl]-amide.

$^1$HNMR (300 MHz, CD$_3$OD) δ: 2.12 (s, 3H), 2.67 (s, 6H), 3.45–3.78 (m, 2H), 4.30(m, 1H), 6.95(s, 2H), 7.22–7.89 (m, 8H).

For production of the following compounds X-6 to X-9, reference is made to Scheme X. However, R for compounds X-6 to X-9 is -(CH$_2$)$_2$-O-Ac.

Acetic acid 2-[3-tert-butoxycarbonylamino-2-(2,4,6-trimethyl-benzenesulfonylamino)-propionylaminol-ethyl ester (X-6).

To a mixture of 3-tert-Butoxycarbonylamino-2-(2,4,6-trimethyl-benzenesulfonylamino)-propionic acid (X-1) (590 mg, 1.528 mmol), 2-acetoxyethanolamine(156 mg, 1.528 mmol), HOBT (248 mg, 1.834 mmol) in DMF (100 mL), was added 1-(3-dimethylamino) propyl)-3-ethylcarbodiimide hydrochloride (352 mg, 1.834 mmol). The reaction was stirred overnight at room temperature. Insoluble particles were removed by filtration and the solvent was evaporated. Purification of the residue on silica gel (1:4 hexane:EtOAc) gave 510 mg (72%) of pure Acetic acid 2-[3-tert-butoxycarbonylamino-2-(2,4,6-trimethyl-benzenesulfonylamino)-propionylamino]-ethyl ester (X-6).

$^1$HNMR (300 MHz, CDCl$_3$) δ: 1.42 (s, 9H), 2.10 (s, 3H), 2.32 (s, 3H), 2.75 (s, 6H), 3.33 (m, 2H), 3.45 (m, 2H), 3.70 (m, 1H), 4.17 (m, 2H), 5.40 (t,1H), 6.80 (t,1H), 6.95(s, 2H), 7.40 (t, 1H).

Acetic acid 2-[3-amino-2-(2,4,6-trimethyl-benzenesulfonylamino)-propionylamino]-ethyl ester (X-7).

2-(Thiazol-2-ylcarbamoyl)-2-(2,4,6-trimethyl-benzenesulfonylamino)-ethyl]-carbamic acid tert-butyl ester (X-6)(156 mg, 0.34 mmol) was mixed with a mixture of (1:1)TFA/CH$_2$Cl$_2$ (20 mL) and the reaction mixture was stirred at room temperature overnight. The solvent was evaporated and the residue was tritured with dry ether (2×15 mL). This gave 160 mg (96%) of pure trifluoroacetate salt of Acetic acid 2-[3-amino-2-(2,4,6-trimethyl-benzenesulfonylamino)-propionylamino]-ethyl ester (X-7).

$^1$HNMR (300 MHz, CD$_3$OD) δ: 2.11 (s, 3H), 2.41 (s, 3H), 2.75 (s, 6H), 3.01 (m, 2H), 3.24 (m, 3H), 3.82 (m, lH), 4.10(m, 2H), 7.05 (s, 2H).

3-([5-(3-N,N-tert-butoxycarbonylguanidino-phenyl)-thiophene-2-carbonyl]-amino}-2-(2,4,6-trimethyl-benzenesulfonylamino)-2-acetoxyethyl propionamide (X-8).

To a mixture of 5-(3-N,N-ditertbutoxycarbonyl Guanidino-phenyl)-thiophene-2-carboxylic acid (X-7) (152 mg, 0.32 mmol), Acetic acid 2-[3-amino-2-(2,4,6-trimethyl-benzenesulfonylamino)-propionylamino]-ethyl ester (N-4) (152 mg, 0.32 mmol), hydroxybenzotriazole (53 mg, 0.23 mmol) in DMF (70 mL), was added 1-(3-dimethylamino) propyl)-3-ethylcarbodiimide hydrochloride (74 mg, 0.23 mmol). The reaction was stirred overnight at room temperature. Insoluble particles were removed by filtration and the solvent was evaporated. Purification of the residue on silica gel (EtOAc) gave 160 mg (62%) of pure 3-{[5-(3-N,N-tert-butoxycarbonylguanidino-phenyl)-thiophene-2-carbonyl]-amino}-2-(2,4,6-trimethyl-benzenesulfonylamino)-2-acetoxyethyl propionamide (X-8).

$^1$HNMR (300 MHz, CDCl$_3$) δ: 1.46(d, 18H), 2.03 (s, 3H), 2.24 (s, 3H), 2.73 (s, 6H), 3.40–3.82 (m, 5H), 4.15(m, 2H), 6.95(s, 2H), 7.22–7.93 (m, 7H).

3-{[5-(3-Guanidino-phenyl)-thiophene-2-carbonyl]-amino}-2-(2,4,6-trimethyl-benzenesulfonylamino)-2-acetoxyethyl propionamide hydrochloride salt (X-9).

3-{[5-(3-N,N-tert-butoxycarbonylguanidino-phenyl)-thiophene-2-carbonyl]-amino}-2-(2,4,6-trimethyl-benzenesulfonylamino)-2-acetoxyethyl propionamide (X-8) (57 mg, 0.07 mmol) was mixed with a saturated solution of HCl/Ether (25 mL) and the reaction mixture was stirred for five hours than treated with a saturated solution of ammonia and kept at room temperature overnight. The solvent was evaporated and the residue was tritured with dry ether (2×25 mL). This gave 55 mg (72%) of pure HCl salt of 3-{[5-(3-Guanidino-phenyl)-thiophene-2-carbonyl]-amino}-2-(2,4,6-trimethyl-benzenesulfonylamino)-2-acetoxyethyl propionamide(X-9).

$^1$HNMR (300 MHz, CD$_3$OD) δ: 2.12 (s, 3H), 2.67 (s, 6H), 3.25–3.78 (m, 7H), 4.03(m, 1H), 6.95(s, 2H), 7.32–7.79 (m, 6H).

3-{[5-(3-Guanidino-phenyl)-thiophene-2-carbonyl]-amino}-2-(2,4,6-trimethyl-benzenesulfonylamino)-2-hydroxyethyl propionamide (X-9).

3-{[5-(3-Guanidino-phenyl)-thiophene-2-carbonyl]-amino}-2-(2,4,6-trimethyl-benzenesulfonylamino)-2-acetoxyethyl propionamide (X-9) was treated with excess methanolic ammonia resulting in the formation of 3-{[5-(3-Guanidino-phenyl)-thiophene-2-carbonyl]-amino}-2-(2,4,6-trimethyl-benzenesulfonylamino)-2-hydroxyethyl propionamide (X-9).

Scheme Y

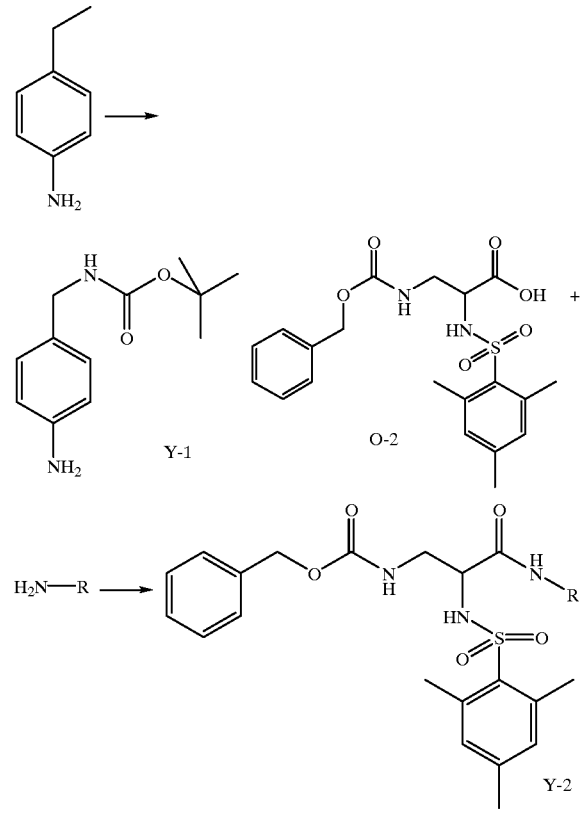

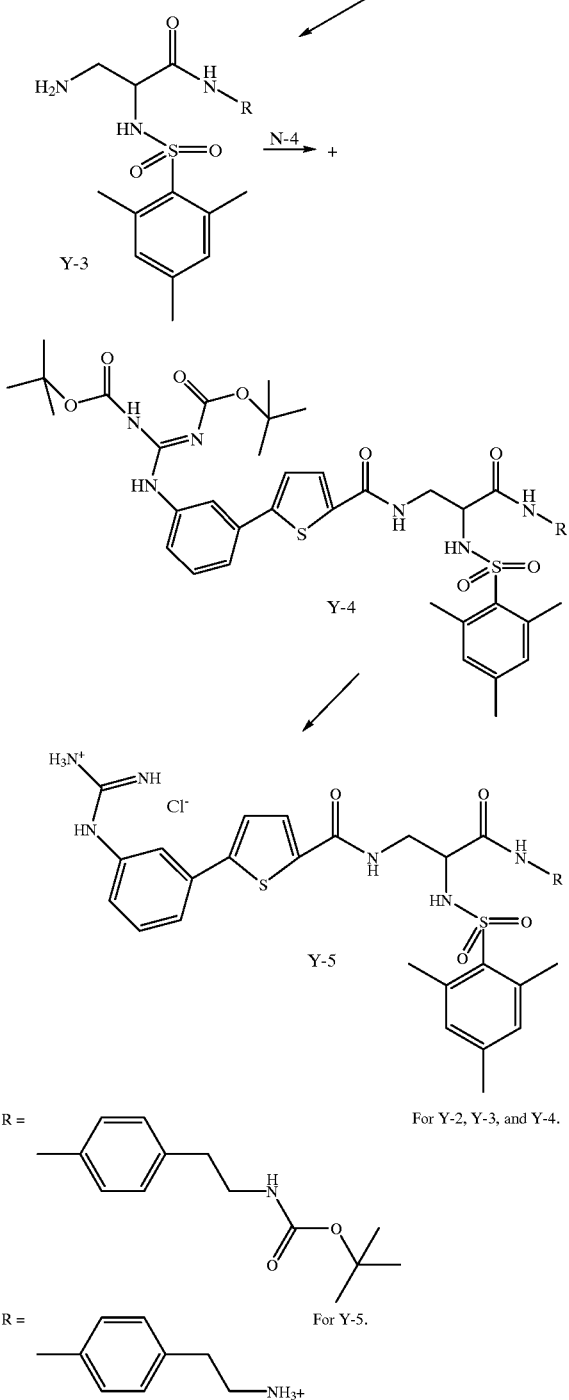

[2-(4-Amino-phenyl)-ethyl]-carbamic acid tert-butyl ester (Y-1).

To a mixture of 2-(4-Amino-phenyl)-ethylamine (300 mg, 2.2 mmol), ditertbutoxyanhydride (480 mg, 2.20 mmol), DMAP (54 mg, 0.44 mmol) DIEA (0.372 ml, 2.3 mmol) in DMF (80 mL), was stirred overnight at room temperature. Insoluble particles were removed by filtration and the solvent was evaporated.

Purification of the residue on silica gel (1:3 hexane:EtOAc) gave 270 mg (52%) of pure [2-(4-Amino-phenyl)-ethyl]-carbamic acid tert-butyl ester.

$^1$HNMR (300 MHz, CDCl$_3$) δ: 1.36 (s, 9H), 2.81 (t, 2H), 3.40 (m, 2H), 3.64 (bs, 1H), 4.63(bs, 1H), 6.72(d, 2H), 7.03 (d, 2H).

[2-[4-(2-tert-Butoxycarbonylamino-ethyl)-phenylcarbamoyl]-2-(2,4,6-trimethyl-benzenesulfonylamino)-ethyl]-carbamic acid benzyl ester (Y-2).

To a mixture of 3-tert-Butoxycarbonylamino-2-(2,4,6-trimethyl-benzenesulfonylamino)-propionic acid (200 mg, 0.51 mmol), [2-(4-Amino-phenyl)-ethyl]-carbamic acid tert-butyl ester (130 mg, 0.55 mmol), HOBT (82 mg, 0.612 mmol) in DMF (25 mL), was added 1-(3-dimethylamino) propyl)-3-ethylcarbodiimide hydrochloride (118 mg, 0.612 mmol). The reaction was stirred overnight at room temperature. Insoluble particles were removed by filtration and the solvent was evaporated. Purification of the residue on silica gel (1:4 hexane:EtOAc) gave 144 mg (42%) of pure [2-[4-(2-tert-Butoxycarbonylamino-ethyl)-phenylcarbamoyl]-2-(2,4,6-trimethyl-benzenesulfonylamino)-ethyl]-carbamic acid benzyl ester (Y-2).

$^1$HNMR (300 MHz, CDCl$_3$) δ: 1.42 (s, 9H), 2.20 (s, 3H), 2.75 (s, 6H), 2.82 (m, 2H), 3.33 (m, 2H), 3.45 (m, 2H), 3.75 (m,1H), 4.77 (s, 1H), 5.02 (s, 2H), 5.60 (s,1H), 6.95(s, 2H), 7.00–7.43 (m, 9H).

(2-{4-[3-Amino-2-(2,4,6-trimethyl-benzenesulfonylamino)-prop-ionylamino]-phenyl}-ethyl)-carbamic acid tert-butyl ester (Y-3)

To a methanolic solution of [2-[4-(2-tert-butoxycarbonylamino-ethyl)-phenylcarbamoyl]-2-(2,4,6-trimethyl-benzenesulfonylamino)-ethyl]-carbamic acid benzyl ester (105 mg, 0.164 mmol) was added Pd/C under a hydrogen atmosphere. The reaction mixture was stirred at room temperature overnight. The catalyst was removed, the solvent was evaporated and the residue was used in the next step without further purification. This gave 80 mg (95%) of pure (2-{4-[3-Amino-2-(2,4,6-trimethyl-benzenesulfonylamino)-propionylamino]-phenyl}-ethyl)-carbamic acid tert-butyl ester (Y-3).

$^1$HNMR (300 MHz, CD$_3$OD) δ: 1.4 (s, 9H), 2.21 (s, 3H), 2.41 (m, 2H), 2.75 (s, 6H), 2.78–3.00 (m, 4H), 3.33 (m, 1H), 6.90(s, 2H), 7.22–7.39 (m, 4H).

3-{[5-(3-N,N-tert-butoxycarbonylguanidino-phenyl)-thiophene-2-carbonyl]2(4-(3-amino}-2-(2,4,6-trimethyl-benzenesulfonylamino)-propionylamino)-phenyl)-ethyl)-carbamic acid tert-butyl ester (Y-4).

To a mixture of 5-(3-N,N-ditertbutoxycarbonyl Guanidino-phenyl)-thiophene-2-carboxylic acid (75 mg, 0.166 mmol), (2-{4-[3-Amino-2-(2,4,6-trimethyl-benzenesulfonylamino)-propionylamino]-phenyl}-ethyl)-carbamic acid tert-butyl ester (80 mg, 0.166 mmol), hydroxybenzotriazole (27 mg, 0.199 mmol) in DMF (70 mL), was added 1-(3-dimethylamino) propyl)-3-ethylcarbodiimide hydrochloride (40 mg, 0.199 mmol). The reaction was stirred overnight at room temperature. Insoluble particles were removed by filtration and the solvent was evaporated. Purification of the residue on silica gel (1:1 hexane:EtOAc) gave 110 mg (70%) of pure-{[5-(3-N, N-tert-butoxycarbonylguanidino-phenyl)-thiophene-2-carbonyl]2(4-(3-amino}-2-(2,4,6-trimethyl-benzenesulfonylamino)-propionylamino)-phenyl)-ethyl)-carbamic acid tert-butyl ester.

$^1$HNMR (300 MHz, CDCl$_3$) δ: 1.46 (s, 9H), 1.55(d, 18H), 2.23 (s, 3H), 2.67 (s, 6H), 2.82 (m, 2H), 3.34 (m, 2H), 3.55–3.82 (m, 2H), 4.44 (bs, 1H), 6.85(s, 2H), 7.12–7.66 (m, 8H), 7.76 (d, 1H), 7.89 (d, 1H).

5-(3-Guanidino-phenyl)-thiophene-2-carboxylic acid [2-[4-(2-amino-ethyl)-phenylcarbamoyl]-2-(2,4,6-trimethyl-benzenesulfonylamino)-ethyl]-amide hydrochloride salt (Y-5).

2-{4-[3-Amino-2-(2,4,6-trimethyl-benzenesulfonylamino)-propionylamino]-phenyl}-ethyl)-carbamic acid tert-butyl ester (Y-4) (70 mg, 0.07 mmol) was mixed with a saturated solution of HCl/Ether (25 mL) and the reaction mixture was stirred at room temperature overnight. The solvent was evaporated and the residue was tritured with dry ether (2×25 mL). This gave 48 mg (90%) of pure HCl salt of 5-(3-Guanidino-phenyl)-thiophene-2-carboxylic acid [2-(thiazol-2-ylcarbamoyl)-2-(2,4,6-trimethyl-benzenesulfonylamino)-ethyl]-amide hydrochloride salt (Y-5).

$^1$HNMR (300 MHz, CD$_3$OD) δ: 2.12 (s, 3H), 2.68 (s, 6H), 2.98 (m, 2H), 3.22 (m, 2H), 3.45(m, 2H), 4.20(m, 1H), 6.90(s, 2H), 7.22–7.89 (m, 10H).

Scheme Z

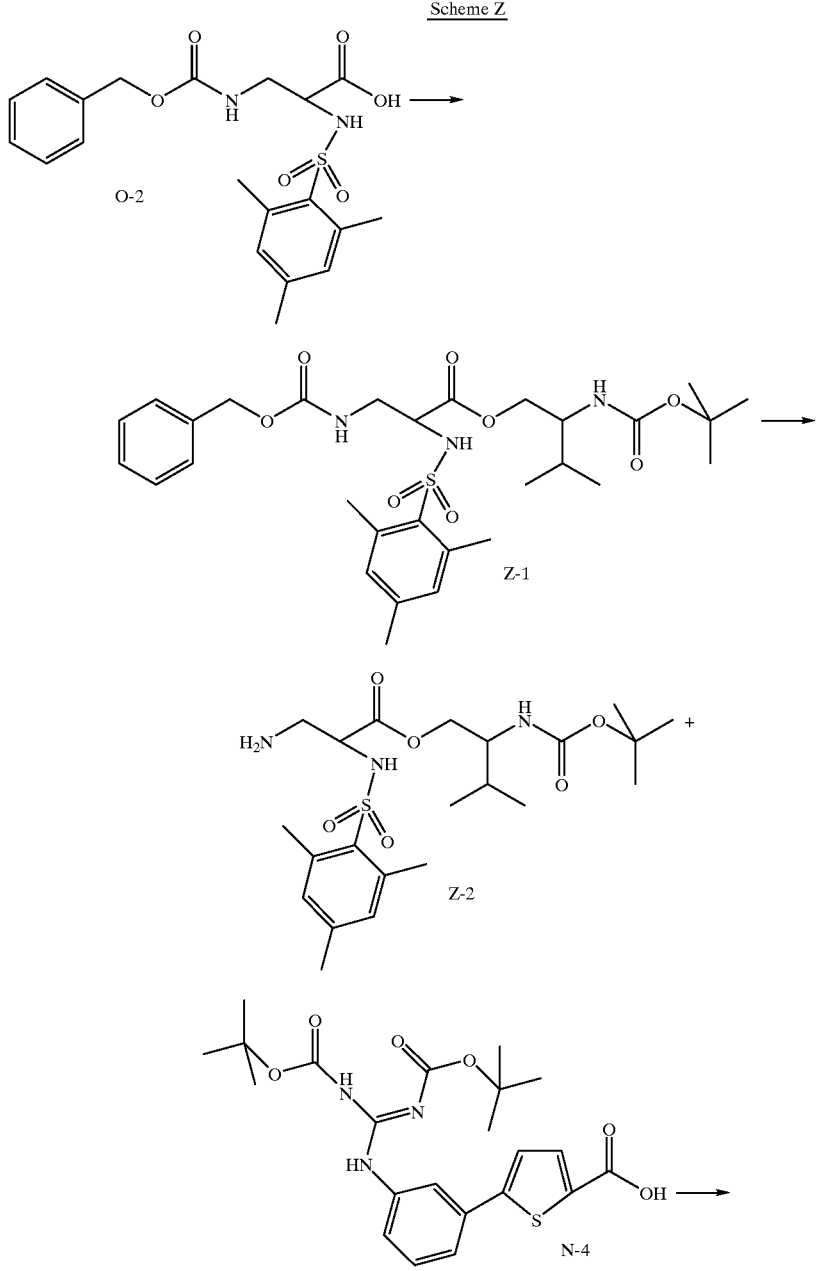

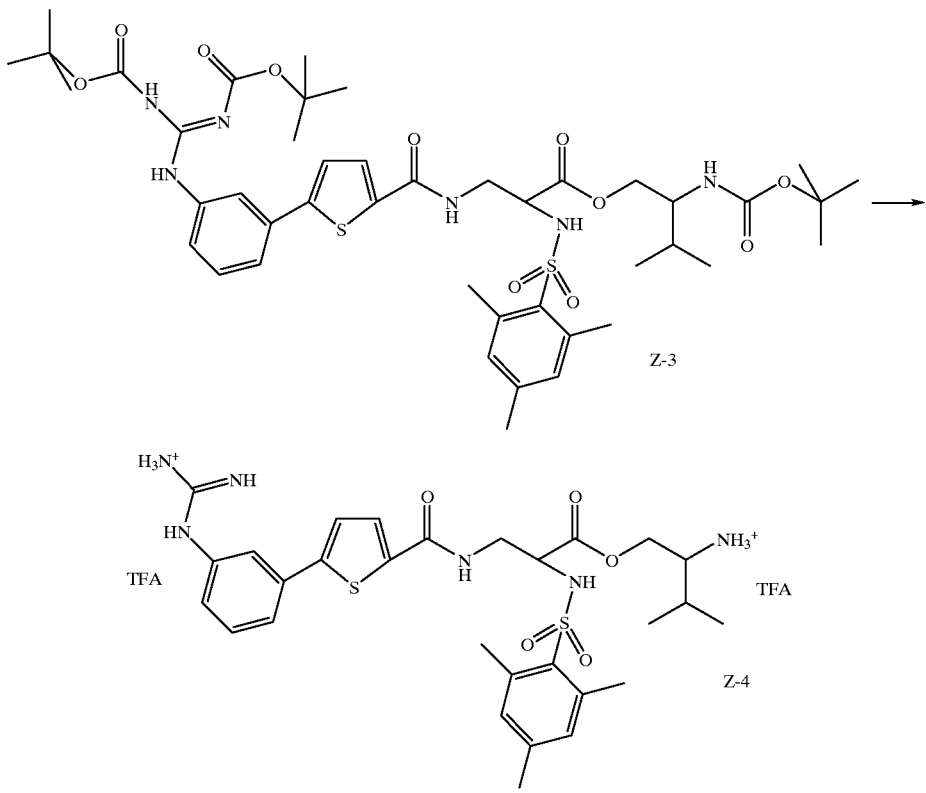

3-Benzyloxycarbonylamino-2-(2,4,6-trimethyl-benzenesulfonylamino)-propionic acid 2-tert-butoxycarbonylamino-3-methyl-butyl ester (Z-1).

To a mixture of 3-benzyloycarbonylamino-2-(2,4,6-trimethyl-benzenesulfonylamnino)-propionic acid (400 mg, 0.95 mmol), valinol (242 mg, 1.18 mmol), BOP (521 mg, 1.18 mmol) in DMF (100 mL), was added triethylamine (0.32 ml). The reaction was stirred 5 h at room temperature. Insoluble particles were removed by filtration and the solvent was evaporated. Purification of the residue on silica gel (1:1 hexane:EtOAc) gave 280 mg (40%) of pure 3-Benzyloxycarbonylamino-2-(2,4,6-trimethyl-benzenesulfonylamino)-propionic acid 2-tert-butoxycarbonylamino-3-methyl-butyl ester (Z-1).

$^1$HNMR (300 MHz, CD$_3$OD) δ: 0.88 ((d, 6H), 1.41 (s, 9H), 1.52 (m,1H), 2.32 (s, 3H), 2.70 (s, 6H), 2.89 (m, 3.43 (m, 2H), 3.75 (m, 3H), 5.01 (s, 2H), 6.98 (s, 2H), 7.39 (m, 5H).

3-Amino-2-(2,4,6-trimethyl-benzenesulfonylamino)-propionic acid 2-tert-butoxycarbonylamino-3-methyl-butyl ester (Z-2).

To a mixture of 3-Benzyloxycarbonylamino-2-(2,4,6-trimethyl-benzenesulfonylamino)-propionic acid 2-tert-butoxycarbonylamino-3-methyl-butyl ester (Z-1) (280 mg, 0.46 mmol methanol (70 ml), was added Pd/C. The reaction was stirred under hydrogen atmosphere overnight at room temperature. Catalyst was removed by filtration and the solvent was evaporated. Purification of the residue on silica gel (1:2 hexane:EtOAc) gave 120 mg (56%) of pure 3-Amino-2-(2,4,$^6$-trimethyl-benzenesulfonylamino)-propionic acid 2-tert-butoxycarbonylamino-3-methyl-butyl ester (Z-2).

$^1$HNMR (300 MHz, CD$_3$OD) δ: 0.89 (d, 6H), 1.41 (s, 9H), 1.54 (m,1H), 2.36(s, 3H), 2.70 (s, 6H), 2.89 (m, 3.43 (m, 2H), 3.75 (m, 3H), 6.98 (s, 2H).

3-{[5-(3-N,N-tert-butoxycarbonylguanidino-phenyl)-thiophene-2-carbonyl]2(4-(3-amino}-2-(2,4,6-trimethyl-benzenesulfonylamino)-2-tert-butoxycarbonylamino-3-methyl-butyl ester (Z-3).

To a mixture of 5-(3-N,N-ditertbutoxycarbonyl Guanidino-phenyl)-thiophene-2-carboxylic acid 40 mg, 0.087 mmol), 3-Amino-2-(2,4,$^6$-trimethyl-benzenesulfonylamino)-propionic acid 2-tert-butoxycarbonylamino-3-methyl-butyl ester (40 mg, 0.086 mmol), hydroxybenzotriazole (14 mg, 0.1 mmol) in DMF (15 mL), was added 1-(3-dimethylamino) propyl)-3-ethylcarbodiimide hydrochloride (20 mg, 0.1 mmol). The reaction was stirred overnight at room temperature. Insoluble particles were removed by filtration and the solvent was evaporated. Purification of the residue on silica gel (EtOAc) gave 51 mg (66%) of pure 3-{[5-(3-N,N-tert-butoxycarbonylguanidino-phenyl)-thiophene-2-carbonyl]2(4-(3-amino}-2-(2,4,6-trimethyl-benzenesulfonylamino)-2-tert-butoxycarbonylamino-3-methyl-butyl ester (Z-3).

$^1$HNMR (300 MHz, CDCl$_3$) δ: 0.89 (d, 6H), 1.41 (s, 9H), 1.55 (2xs, 18H), 1.80 (m,1H), 2.36(s, 3H), 2.70 (s, 6H), 3.56–3.78 (m, 3H), 3.89 (m, 1H), 4.15 (m, 1H), 4.4 (bs, 1H), 4.82 (bs, 1H), 6.98 (s, 2H), 7.40 s, 2H), 7.33–7.42 (m, 3H), 7.81 (s, 1H).

3-{[5-(3-Guanidino-phenyl)-thiophene-2-carbonyl]-amino}-2-(2,4,6-trimethyl-benzenesulfonylamino)-propionic acid 2-amino-3-methyl-butyl ester trifluoroacetate salt (Z-4).

3-{[5-(3-N,N-tert-butoxycarbonylguanidino-phenyl)-thiophene-2-carbonyl]2(4-(3-amino}-2-(2,4,6-trimethyl-benzenesulfonylamino)- 2-tert-butoxycarbonylamino-3- methyl-butyl ester (51 mg, 0.056 mmol) was mixed with a solution of TFA/CH₂CL₂ (15 mL) and the reaction mixture was stirred at room temperature overnight. The solvent was evaporated and the residue was tritured with dry ether (2×25 mL). This gave 38 mg (81%) of pure TFA salt of 3-{[5-(3-Guanidino-phenyl)-thiophene-2-carbonyl]-amino}-2-(2,4, 6-trimethyl-benzenesulfonylamino)-propionic acid 2-amino-3-methyl-butyl ester.

$^1$HNMR (300 MHz, CD$_3$OD) δ: 1.11 (d, 6H), 2.10 (m,1H), 2.22 (s, 3H), 2.70 (s, 6H), 3.56 (m, 1H), 3.89 (m, 1H), 4.15–4.55 (m, 3H), 6.98 (s, 2H), 7.40–7.88 (m, 6H).

Scheme AA

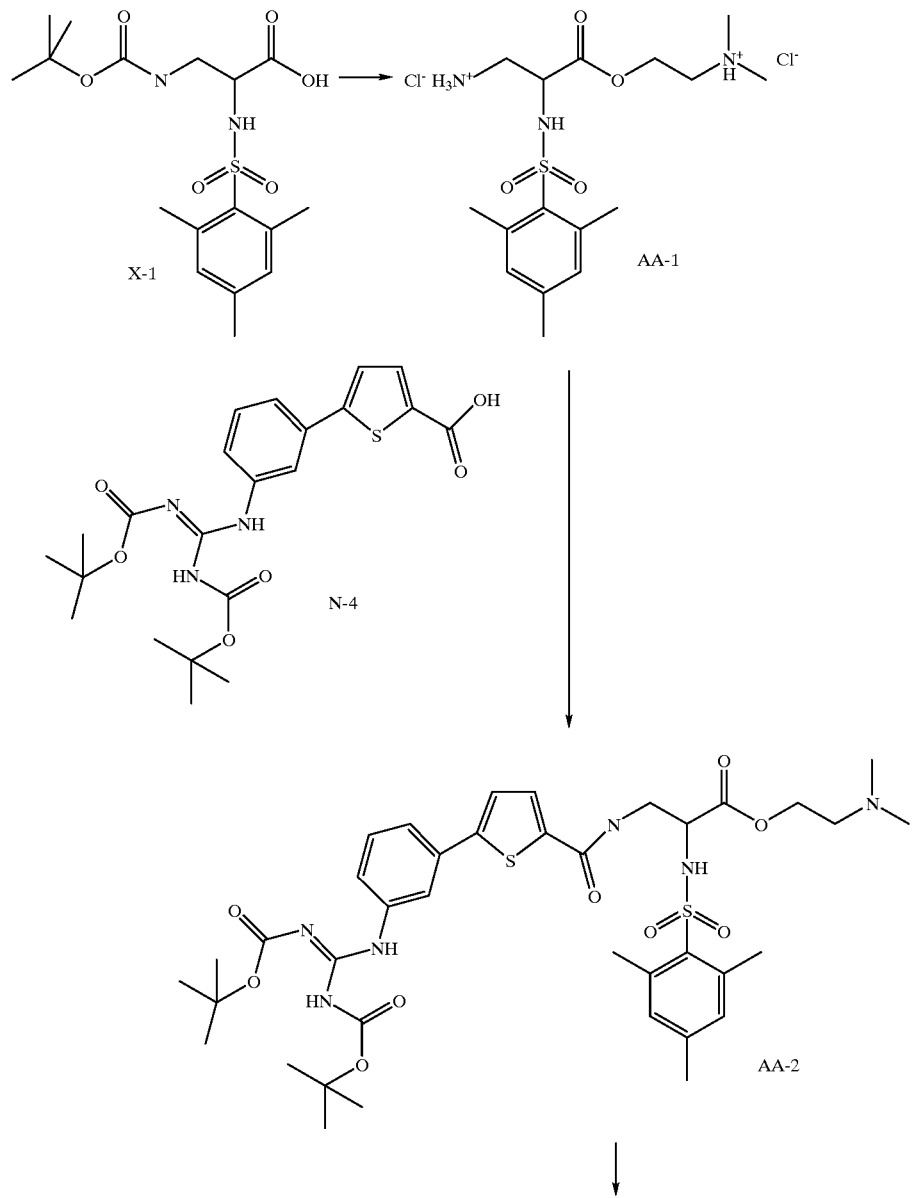

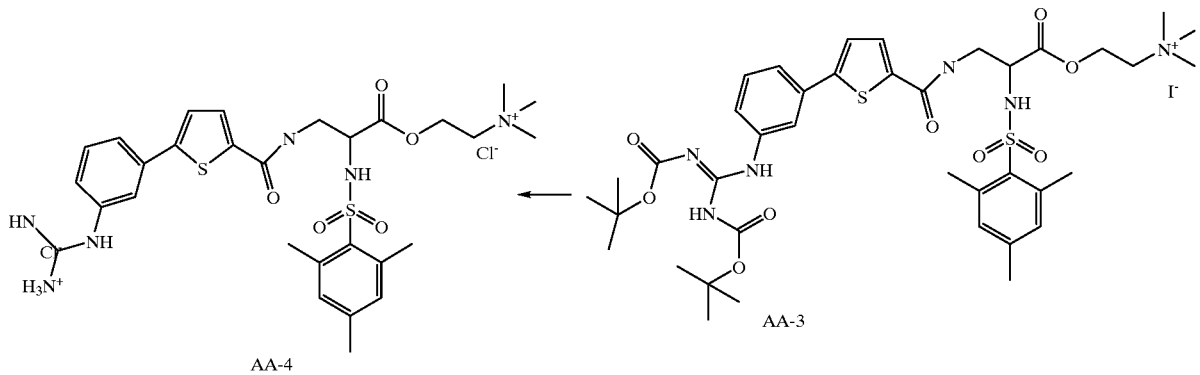

AA-4

AA-3

3-Amino-2-(2,4,6-trimethyl-benzenesulfonylamino)-propionic acid 2-dimethylamino-ethyl ester dihydrochloric salt (AA-1).

To a solution of dimethylaminoethanol (0.32 mL, 3.23 mmol), triethylamine (0.76 mL, 5.46 mmol) and 3-tert-Butoxycarbonylamino-2-(2,4,6-trimethyl-benzenesulfonylamino)-propionic acid (1 g, 2.58 mmol) in dimethylformamide (10 mL) is added BOP (1.42 g, 3.23 mmol). The solution is stirred overnight at room temperature. Dilute with ethyl acetate extract with water 2x, NaHCO3 2x, Brine, water then brine. Dry with $Na_2SO_4$. Take the crude solution in HCl/Dioxane 4M stir at room temperature for 4 hrs. Triturate in ether overnight dry under vacuum this afford 1.03 g of the title compound with purity >90%.

$^1$H NMR (400 MHz)(CD3OD) δ: 7.09 (s, 2H), 4.41–4.37 (m, 1H), 4.28–4.23 (m, 2H), 3.53–3.45 (m, 2H), 3.30–3015 (m, 2H), 2.88 (s, 3H), 2.86 (s, 3H), 2.60 (s, 6H), 2.33 (s, 3H). 3-{[5-(3-bis-Boc-Guanidino-phenyl)-thiophene-2-carbonyl]-amino}-2-(2,4,6-trimethyl-benzenesulfonylamino)-propionic acid 2-dimethylamino-ethyl ester (AA-2).

To a solution of 3-Amino-2-(2,4,6-trimethyl-benzenesulfonylamino)-propionic acid 2-dimethylamino-ethyl ester dihydrochloric salt (AA-1) (100 mg, 0.22 mmol) in DMF (2 mL) at room temperature is added triethylamine (0.12 mL, 0.88 mmol) then the solution is stirred 30 min. Add simultaneoustly 5-(3-bisBOCGuanidino-phenyl)-thiophene-2-carboxylic acid (98 mg, 0.22 mmol), HOBT (32 mg, 0.24 mmol) and EDCI (46 mg, 0.24 mmol) then stir 48 hrs at room temperature. The solution is evaporated to dryness and the residue is dissolved in a minimum of $CH_2Cl_2$ and purified using flash chromatography (50% accept/hexane to 20% MeOH/80% accept). Giving the title compound in 87% yield.

$^1$HNMR (400 MHz) (CD3OD) δ: 7.94 (s, 1H), 7.55–7.28 m, 5H), 6.85 (s, 2H), 4.31 (t, 2H, J=5 Hz), 4.21–4.18 (m, 1H), 3.73–3.62 (m, 1H), 3.58–3.48 (m, 1H), 3.24–3,21 (m, 2H), 2.81 (s, 6H), 2.60 (s, 6H), 2.15 (s, 3H), 1.54 (s, 18H). {2-[3-{[5-(3-Guanidino-phenyl)-thiophene-2-carbonyl]-amino}-2-(2,4,6-trimethyl-benzenesulfonylamino)-propionyloxy]-ethyl}-trimethyl-ammonium; iodide (AA-3).

To a solution of 3-{[5-(3-bis-BOC-Guanidino-phenyl)-thiophene-2-carbonyl]-amino}-2-(2,4,6-trimethyl-benzenesulfonylamino)-propionic acid 2-dimethylamino-ethyl ester (153 mg, 0.19 mmol) in acetone (2 mL) at room temperature is added methyl iodide (0.06 mL, 1 mmol). The flask is covered with foil paper to avoid contact with light and the solution is stirred overnight. The mixture is evaporated to dryness then triturate using ether then dichloromethane. The solid is dried under vacuum overnight to afford 80 mg of the title compound.

$^1$HNMR (400 MHz) (CD3OD) δ8.00 (s, 1H), 7.57–7.40 m, 5H), 6.86 (s, 2H), 4.57 (m, 2H), 4.25–4.21 (m, 1H), 3.77–3.69 (m, 3H), 3.58–3.46 (m, 2H), 3.28 (s, 9H), 2.61 (s, 6H), 2.13 (s, 3H), 1.60 (s, 9H), 1.49 (s, 9H).

{2-[3-{[5-(3-Guanidino-phenyl)-thiophene-2-carbonyl]-amino}-2-(2,4,6-trimethyl-benzenesulfonylamino)-propionyloxy]-ethyl}-trimethyl-amnonium; iodide (AA-4).

{2-[3-{[5-(3-Guanidino-phenyl)-thiophene-2-carbonyl]-amino}-2-(2,4,6-trimethyl-benzenesulfonylamino)-propionyloxy]-ethyl}-trimethyl-ammonium; iodide (80 mg, 0.084 mmol) was mixed with a solution of HCl/Dioxane 4M (4 mL) and stir at room temperature overnight. Evaporate to dryness then triturate in ether and in dichloromethane dry under vacuum. It yielded 40 mg.

$^1$HNMR (400 MHz) (CD3OD) δ:8.51–8.45 (m, 1H), 7.71 (d, 1H, J=8 Hz), 7.62 (s, 1H), 7.57 (d, 1H, J=8 Hz), 7.39 (s, 1H), 7.32 (d, 1H, J=8 Hz), 6.85 (s, 2H), 5.51 (s, 1H), 4.65–4.50 (m, 2H), 4.26–4.23 (m, 1H), 3.78–3.68 (m, 3H), 3.55–3.50 (m, 2H), 3.28 (s, 9H), 2.61 (s, 6H), 2.13 (s, 3H).

Scheme AB

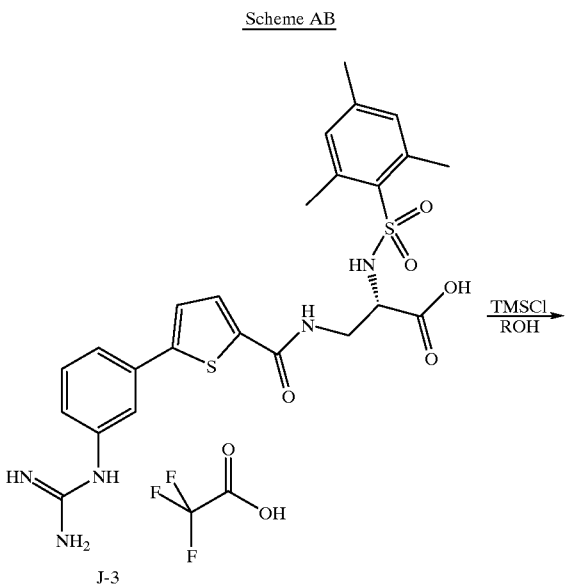

J-3

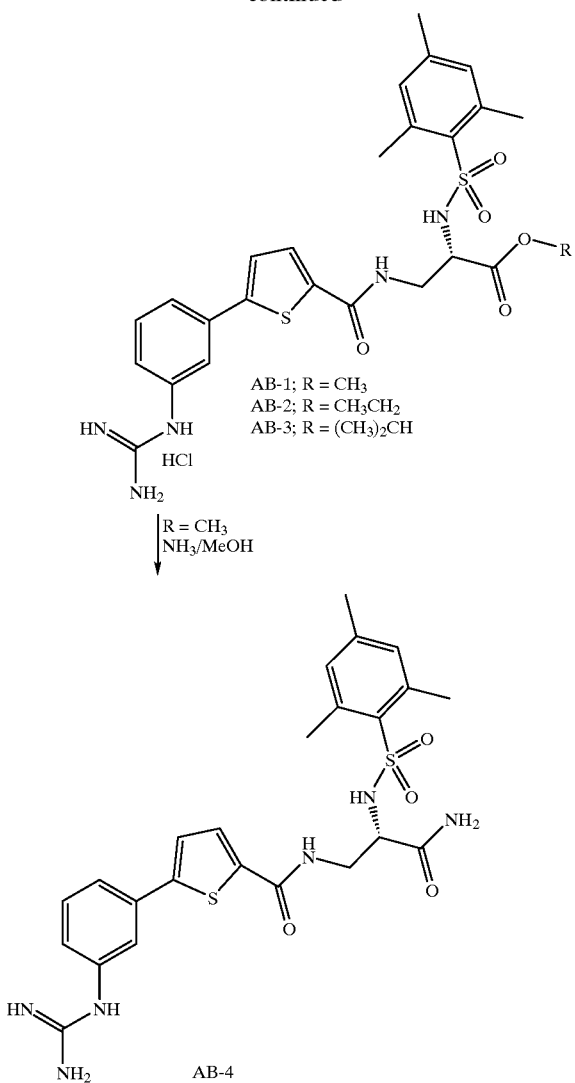

AB-1; R = CH₃
AB-2; R = CH₃CH₂
AB-3; R = (CH₃)₂CH

R = CH₃
NH₃/MeOH

AB-4

5-(3-Guanidino-phenyl)-thiophene-2-carboxylic acid [2-carbamoyl-2-(2,4,6-trimethyl-benzenesulfonylamino)-ethyl]-carboxylic acid methyl ester (AB-1).

Trimethyl silyl chloride (1 mL) was added to a solution of the acid (J-3) (104 mg, 0.18 mmol) in ethanol (4 mL) and the mixture stirred at room temperature for 15 hours. All the solvent was evaporated to dryness and the solid triturated in ether. Freeze-drying of the suspension afforded 87 mg (84%) of clean ester (AB-1).

¹HNMR (400 MHz, DMSO-d6): 9.85 (s, 1H), 8.61 (s, 1H), 8.29 (d, J=9.0 Hz, 1H), 7.65–7.50 (m, 9H), 7.23 (d, J=7.0 Hz, 1H), 6.91 (s, 2H), 4.04 (m, 1H), 3.52 (m, 1H), 3.39 (s, 3H), 3.31 (m, 1H), 2.17 (s, 3H)

5-(3-Guanidino-phenyl)-thiophene-2-carboxylic acid [2-carbamoyl-2-(2,4,6-trimethyl-benzenesulfonylamino)-ethyl]-carboxylic acid ethyl ester (AB-2).

Trimethyl silyl chloride (1 mL) was added to a solution of the acid (J-3) (102 mg, 0.18 mmol) in ethanol (4 mL) and the mixture stirred at room temperature for 15 hours. All the solvent was evaporated to dryness and the solid triturated in ether. Freeze-drying of the suspension afforded 88 mg (82%) of clean ester (AB-2).

¹HNMR (400 MHz, DMSO-d6): 9.90 (s, 1H), 8.63 (d, J=5.5 Hz, 1H), 8.28 (d, J=9.5 Hz, 1H), 7.65–7.50 (m, 9H), 7.23 (d, J=7.0 Hz, 1H), 6.93 (s, 2H), 4.02 (q, J=8.0 Hz, 1H), 3.77 (q, J=7.0 Hz, 2H), 2.18 (s, 3H), 0.96 (t, J=7.0 Hz, 3H).

5-(3-Guanidino-phenyl)-thiophene-2-carboxylic acid [2-carbamoyl-2-(2,4,6-trimethyl-benzenesulfonylamino)-ethyl]-carboxylic acid isopropyl ester (AB-3).

Trimethyl silyl chloride (1 mL) was added to a solution of the acid (J-3) (106 mg, 0.19 mmol) in ethanol (4 mL) and the mixture stirred at room temperature for 15 hours. All the solvent was evaporated to dryness and the solid triturated in ether. Freeze-drying of the suspension afforded 104 mg (91%) of clean ester.

¹HNMR (400 MHz, DMSO-d6): 9.89 (s, 1H), 8.64 (s, 1H), 8.25 (d, J=10.0 Hz, 1H), 7.65–7.50 (m, 9H), 7.22 (d, J=8.0 Hz, 1H), 6.93 (s, 2H), 4.57 (m, 1H), 4.10 (m, 1H), 3.99 (m, 1H), 3.52 (m, 1H), 2.18 (s, 3H), 0.91 (d, J=5.5 Hz, 6H).

5-(3-Guanidino-phenyl)-thiophene-2-carboxylic acid [2-carbamoyl-2-(2,4,6-trimethyl-benzenesulfonylamino)-ethyl]-amide hydrochloride salt (AB-4).

5-(3-Guanidino-phenyl)-thiophene-2-carboxylic acid [2-carbamoyl-2-(2,4,6-trimethyl-benzenesulfonylamino)-ethyl]-carboxylic acid (80 mg, 0.156 mmol) (AB-1) was mixed with a solution of TMSCl (0.08 ml, 0.856 mmol), CH₃OH (25 mL). The reaction mixture was stirred at room temperature overnight. The solvent was evaporated and the residue was tritured with dry ether (2×25 mL). This gave 77 mg (97%) of pure methyl ester. This compound was then treated with a saturated solution of ammoniac in methanol (30 ml). Solvent was than evaporated and the residue was treated with a saturated solution of HCl/ether (25 ml). The solvent was evaporated and the residue was again tritured with dry ether (2×30 mL) to give pure 5-(3-Guanidino-phenyl)-thiophene-2-carboxylic acid [2-carbamoyl-2-(2,4,6-trimethyl-benzenesulfonylamino)-ethyl]-amide hydrochloride salt (AB-4).

¹HNMR (300 MHz, CD₃OD) δ: 2.12 (s, 3H), 2.73 (s, 6H), 3.36 (m, 1H), 3.69 (m, 1H), 4.15 (m, 1H), 6.88 (s, 2H), 7.30–7.78 (m, 6H).

SCHEME AC

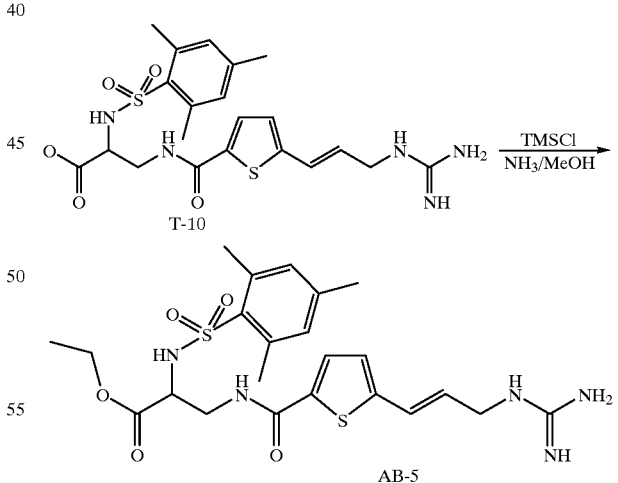

5-(3-Guanidino-phenyl)-thiophene-2-carboxylic acid [2-carbamoyl-2-(2,4,6-trimethyl-benzenesulfonylamino)-ethyl]-amide hydrochloride salt (AC-1).

5-(3-Guanidino-phenyl)-thiophene-2-carboxylic acid [2-carbamoyl-2-(2,4,6-trimethyl-benzenesulfonylamino)-ethyl]-carboxylic acid (AB-4) (80 mg, 0.156 mmol) was mixed with a solution of TMSC1 (0.08 ml, 0.856 mmol), CH₃OH (25 mL). The reaction mixture was stirred at room temperature overnight. The solvent was evaporated and the residue was tritured with dry ether (2×25 mL). This gave 77 mg (97%) of pure methyl ester. This compound was then treated with a saturated solution of ammoniac in methanol (30 ml). Solvent was than evaporated and the residue was treated with a saturated solution of HCl/ether (25 ml). The solvent was evaporated and the residue was again tritured with dry ether (2×30 mL) to give pure 5-(3-Guanidino-phenyl)-thiophene-2-carboxylic acid [2-carbamoyl-2-(2,4,6-trimethyl-benzenesulfonylamino)-ethyl]-amide hydrochloride salt (AC-1).

$^1$HNMR (300 MHz, CD$_3$OD) δ: 2.12 (s, 3H), 2.73 (s, 6H), 3.36 (m, 1H), 3.69 (m, 1H), 4.15 (m, 1H), 6.88 (s, 2H), 7.30–7.78 (m, 6H).

Example 2

Biolooical Assays

Assay 1. Fibrinogen Binding to Immobilized $α_{IIb}β_3$ and $α_vβ_3$
(Solid-Phase Assays)

The wells of plastic microtiter plates were coated overnight at 4° C. with purified active $α_{IIb}β_3$ (Calbiochem) or placental $α_vβ_3$ at 0.5 ug/mL (100 uL/well) in a buffer containing 150 mM NaCl, 20 mM Tris, pH 7.4, 1 mM MgCl$_2$, 0.2 mM MnCl$_2$, and including 1 mM CaCl$_2$ for $α_{IIb}β_3$ Blocking of nonspecific sites was achieved by incubating the wells with 35 mg/mL bovine serum albumin (BSA) for at least 2 hours at 37° C. Biotinylated-fibrinogen (10 nM) was added in 0.2 mL binding buffer (100 mM NaCl, 50 mM Tris, pH 7.4, 1 mM MgCl$_2$, 0.2 mM MnCl$_2$ and 1 mg/mL BSA including 1 mM CaCl$_2$ for $α_{IIb}β_3$) to the wells in triplicate in the absence or presence of increasing concentrations of compounds of interest (0.001–100 uM) and further incubated for 2 hours at 37° C. Nonbound fibrinogen was removed by five washes with binding buffer. Avidin conjugated to alkaline phosphatase (Sigma), diluted in binding buffer, was added and incubated for two hours at 37° C. The plates were washed five times with binding buffer, and after addition of the substrate PNPP (Pierce), the enzyme activity was measured by the absorbance at 405 nm. The concentration of inhibitor required to inhibit 50% of biotinylated-fibrinogen binding was defined as IC$_{50}$ determined by a nonlinear, sigmoidal dose response variable slope from the GraphPad Prism software. The results of the $α_vβ_3$ and $α_{IIb}β_3$ assays are reported in Table 1.

TABLE 1

Solid Phase Assay: $α_vβ_3$ and $α_{IIb}β_3$

| Compound Number | IC$_{50}$ (nM) $α_vβ_3$ | IC$_{50}$ (nM) $α_{IIb}β$ | Selectivity |
|---|---|---|---|
| E-2 | 2.7 | 0.55 | 0.2 |
| F-2 | 8.2 | 0.25 | 0.03 |
| K-3 | 1.5 | 1.4 | 1 |
| M-3 | 1.9 | 1.1 | 0.6 |
| U-2 | 0.5 | 0.54 | 1 |
| X-5 | 360 | N/A | N/A |
| X-9 | 346.7 | N/A | N/A |
| AB-4 | 36.3 | N/A | N/A |
| AB-2 | 104.3 | N/A | N/A |
| AC-1 | 290 | N/A | N/A |

Assay 2. Cell Attachment

The wells of 96-well plates (Immunolon) were coated, by incubation overnight at 4° C., with 5 ug/mL vitronectin, 2 ug/mL osteopontin, or fibronectin or 10 mg/mL BSA in PBS. The protein solution was flicked out and the wells were blocked with 10 mg/mL BSA (0.1 mL) for 1–2 hours at 37° C. Cells HT29, K562, or K562 transfected with $α_vβ_3$ (Blystone et al., 1994) were loaded with a fluorescent marker, 5-chloromethylfluorescein diacetate (Molecular Probes, Eugene, OR) for 1 hour at 37° C., then incubated in fresh medium without the fluorescent marker for 1 hour. Cells were lifted with trypsin-EDTA and washed two times with Hank's balanced salt solution minus cations (Sigma) supplemented with 1 mM MgCl$_2$ Cells (75,000 cells/well) were added to coated plates in triplicate and allowed to attach at 37° C. for 1 hour in the presence or absence of specific antibodies (5 ug/mL) or 10-fold dilutions of compounds of interest starting at 10 uM. Nonadherent cells were removed by gentle washing twice with PBS. The adherent cells were solubilized with 1% triton x-100 and detected using a fluorescence plate reader (DYNEX Technologies). The number of attached cells was calculated based upon standard curves for each cell line used in the experiment. Non-specific cell attachment (attachment to wells coated with BSA) was always less than 5%. The results are presented in Table 2.

TABLE 2

Cell attachment assay

| Compound number | IC50 (nM) $α_vβ_3$ | IC50 (nM) $α_vβ_5$ | IC50 (nM) $α_5β_1$ |
|---|---|---|---|
| E-2 | 0.18 | 72 | 640 |
| F-2 | 2.9 | 11 | 71 |
| K-3 | 2.8 | 6.4 | 80 |
| M-3 | 0.018 | 1.6 | 34 |
| U-2 | 1.5 | 6 | 6.1 |

Assay 3. Cytotoxicity (MTT)

The wells of microtiter plates were seeded with 2000 cells/well T24, 2500 cells/well HT29 or 5000 cells/well HMVEC (Cell Systems) in 100 uL, followed by an overnight culture for cell adhesion. The next day, the media is supplemented with 100 uL of 10-fold dilution of compound of interest starting at 10 uM. Following culture for 72 hours, 3-(4, 5-dimethyl-2-thiazolyl)-2, 5-diphenyltetrazolium bromide (MTT; Sigma) at 2 mg/mL was added to each well (50 uL/well) and further incubated for 4 hours at 37° C. The medium was flicked out and 200 uL of a 1:1 solution of ethanol:acetone followed by 25 uL of glycine buffer (0.1 M glycine, 0.1M NaCl, pH 10.5) is added and the color measured by the absorbance at 570 nm. The results are presented in Table 3.

TABLE 3

Cytotoxicity Assay
(HMVEC selectivity)

| Compound number | IC$_{50}$ (uM) HMVEC | IC$_{50}$ (uM) HT29 | IC$_{50}$ (uM) B16F10 |
|---|---|---|---|
| E-2 | 0.20 | >10 | 1.3 |
| F-2 | 0.031 | 4.6 | 0.19 |
| K-3 | 0.045 | 5.1 | 0.32 |
| M-3 | 0.14 | 6.9 | 0.26 |
| U-2 | 0.026 | 4.8 | 0.18 |

Assay 4. Chick Chorioallantoic Membrane (CAM)

A) Shell-less Embryo Culture

Fertilized white leghorn chicken eggs (SPAFAS Inc., Norwich, Conn.) were received at day 0 and incubated for 3 days at 37 C with constant humidity. On day 3, eggs were rinsed with 70% ethanol and opened into 100 mm² tissue culture coated Petri dishes under aseptic conditions. The embryos were then returned to a humidified 38 C incubator for 7–9 additional days.

B) Mesh Assay

Vitrogen (Collagen Biomaterials, Palo Alto, Calif.) at a final concentration of 0.73 mg/mL and Matrigel (Becton Dickinson, Bedford, Mass.) at a final concentration of 10 mg/mL was directly pipetted onto Nylon meshes with 250 µm² openings which were cut into 4 mm×4 mm squares and autoclaved. Polymerization of meshes were under aseptic conditions, on bacteriological Petri dishes. The polymerization conditions for each substrate were identical; after mixing with or without 250 µg of VPF/VEGF$_{165}$ (Peprotech, Rocky Hill, N.J.) and/or compounds of interest, 40 µL were pipetted onto each mesh in a bacteriological Petri dish. The Petri dish was placed in a humidified 37 C incubator with 5% $CO_2$ for 30 minutes to allow polymerization followed by an incubation at 4° C. for 2 hours.

In a tissue culture enclosure, meshes were placed onto the periphery of the CAM of a day 12–14 embryo, excluding areas containing major vessels. The embryos were then returned to the humidified 38° C. incubator with 3% $CO_2$ for 24 to 48 additional hours.

C) Visualization and Quantification of Vessels

Embryos were removed from the incubator and meshes were viewed under a dissecting microscope for gross evaluation. Injection of 400 µL FITC dextran, MW 2,000,000 (Sigma, St. Louis, Mo.) through glass microcapillary tubes by infusion into the umbilical vein was performed at a rate of 200 µl per minute. The FITC dextran was allowed to circulate for 5 minutes and 3.7% formaldehyde in PBS was applied directly on each mesh. The embryos were then incubated at 4° C. for 5 minutes and the meshes were dissected off the CAM and fixed in 3.7% formaldehyde for 10 minutes to overnight.

After fixation, meshes were mounted on slides with 90% glycerol in PBS and visualized on an inverted fluorescence microscope. A Nikon Diaphot with a Sony DXC-151A camera attached to the side port was used for capture of images and analysis was with the NIH Image 1.61 software program. For each mesh, 5 random staggered images (approximately 600 µm each) were captured. The areas of high intensity were highlighted and measured. Results are expressed as ability to suppress capillary formation after subtraction from negative control. Values were calculated as % inhibition, considering 100% the capillary density achieved by VPF in the presence of vitrogen alone minus the background levels in the absence of VPF. Negative values indicated angiogenic stimulation above the VPF positive control. Results for the cam assay showed significant inhibition values for some of the compounds tested.

While particular embodiments of the invention have been described, it will also be apparent to these of ordinary skill in the art that various modifications, including the preparation of certain analogs, can be made without departing from the spirit and scope of the invention. Accordingly, it is not intended that the invention be limited except by the appended claims.

What is claimed is:

1. A compound of formula I:

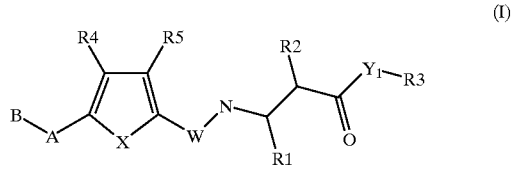

and pharmaceutically acceptable salts thereof, wherein:
X is selected from the group consisting of O and S;
$Y_1$ is selected from the group consisting of O, S and N;
W is selected from the group consisting of carbonyl and sulfonyl;
R1 and R2 are independently selected from the group consisting of H, $C_{5-10}$aryl, $C_{5-10}$arylsulfonylamino, $C_{5-10}$cycloalkylsulfonylamino, $C_{5-10}$arylamino and $C_{5-10}$aryl$C_{1-6}$alkyl with the proviso that R1 and R2 are not both H;
R3 is selected from the group consisting of H, $C_{1-8}$alkyl, $C_{1-8}$alkylamino $C_{0-8}$alkyl, $C_{1-8}$alkoxy, $C_{1-8}$alkylepoxy $C_{1-8}$alkyl$C_{1-8}$alkyl-$Y_2$C(O)$Y_3$—$C_{0-8}$alkyl, $C_{5-8}$aryl, $C_{5-8}$aryl$C_{0-8}$alkyl-$Y_2$C(O)$Y_3$—$C_{0-8}$alkyl, $C_{5-8}$aryl, $C_{1-8}$alkyl$C_{5-8}$aryl, and $C_{5-8}$aryl$C_{1-8}$alkyl, wherein $Y_2$ and $Y_3$ are independently O or N;
R4 and R5 are independently selected from the group consisting of H, halogen, $C_{1-6}$alkyl and $C_{1-6}$alkoxy;
A is selected from the group consisting of $C_{1-6}$alkyl, $C_{2-6}$alkenyl, $C_{2-6}$alkynyl, $C_{5-10}$aryl, $C_{3-10}$cycloakyl; and
B is selected from the group consisting of amino, $C_{1-6}$aminoalkyl, $C_{5-10}$arylamino, guanidino, $C_{1-6}$guanidinoalkyl, cyclic guanidino, urea, cyclic urea.

2. The compound of claim 1, wherein X is S.

3. The compound of 1, wherein R1 and R2 are represented by the formula N—$Y_4$—R6 wherein
$Y_4$ is selected from the group consisting of —$CO_2$—, —$SO_2$— and —$(CH_2)_{0-2}$—;
R6 is selected from the group consisting of:

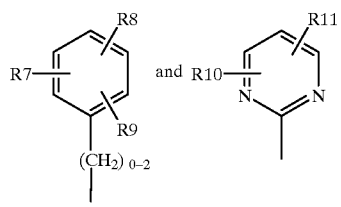

wherein R7, R8, R9, R10, R11 are independently selected from the group consisting of H, $C_{1-6}$alkyl, $C_{1-6}$alkoxy and halogen.

4. The compound of claim 2, wherein R4 and R5 are H.

5. The compound of claim 2, wherein W is carbonyl.

6. The compound of claim 2, wherein R1 is H and R2 is $C_{5-10}$arylsulfonylamino.

7. The compound of claim 5, wherein R1 is H and R2 is selected from the group consisting of phenylsulfonylamino and trimethylphenylsulfonylamino.

8. The compound of claim 2, wherein R1 is H and R2 is $C_{5-10}$aralkyl.

9. The compound of claim 7, wherein R1 is H and R2 is benzyloxycarbonyl.

10. The compound of claim 2, wherein R1 is H and R2 is $C_{5-10}$arylamino.

11. The compound of claim 8, wherein R1 is H and R2 is pyrimidinylamino.

12. The compound of claim 2, wherein A is $C_{1-6}$alkyl.

13. The compound of claim 12, wherein A is —$(CH_2)_3$—.

14. The compound of claim 2, wherein A is $C_{2-6}$alkenyl.

15. The compound of claim 14, wherein A is —$(CH_2)_{0-2}$—C=C—$(CH_2)_{0-2}$—.

16. The compound of claim 15, wherein A is —CH=CH—$CH_2$—.

17. The compound of claim 2, wherein A is $C_{2-6}$alkynyl.

18. The compound of claim 17, wherein A is —$(CH_2)_{0-2}$—C≡C—$(CH_2)_{0-2}$—.

19. The compound of claim 18, wherein A is —C≡C—$CH_2$—.

20. The compound of claim 2, wherein A is $C_{5-10}$aryl.

21. The compound of claim 20, wherein A is selected from the group consisting of:

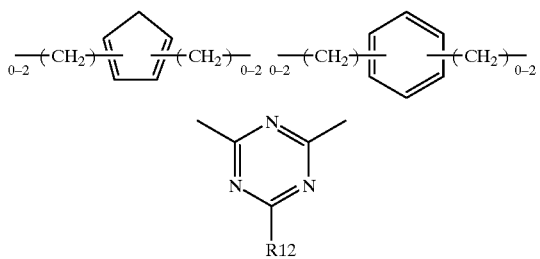

wherein $R_{12}$ is selected from the group consisting of H, $C_{1-6}$ alkyl, $C_{1-6}$alkoxy and $NH_2$.

22. The compound of claim 21, wherein A is selected from the group consisting of:

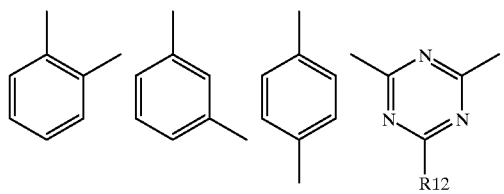

wherein $R_{12}$ is selected from the group consisting of H and $NH_2$.

23. The compound of claim 2, wherein B is selected from the group consisting of guanidino and $C_{1-6}$guanidinoalkyl.

24. The compound of claim 2, wherein B is selected from the group consisting of amino, $C_{1-6}$aminoalkyl, $C_{5-10}$arylamino.

25. The compound of claim 1, wherein either R1 or R2 are H with the proviso that both R1 and R2 are not H.

26. The compound of claim 1, wherein $Y_1$ is —NH—.

27. The compound of claim 1, wherein $Y_1$ is —C—.

28. The compound of claim 1, wherein R3 is selected from the group consisting of H, halogen, $C_{1-18}$alkyl, $C_{1-18}$alkylamino $C_{0-18}$alkyl, $C_{1-18}$hydroxyalkyl, $C_{1-18}$alkylether, $C_{1-18}$alkylthioether, $C_{1-18}$alkyl-$Y_2C(O)Y_3$—$C_{0-18}$alkyl, $C_{1-18}$alkyl-$C(O)Y_3$—$C_{0-18}$alkyl, $C_{1-18}$alkyl-$Y_2C(O)$—$C_{0-18}$alkyl, $C_{5-12}$aryl, $C_{5-12}$aryl$C_{0-18}$alkyl-$Y_2C(O)Y_3$—$C_{0-18}$alkyl, $C_{1-18}$alkyl$C_{5-12}$aryl, $C_{5-12}$aryl$C_{1-18}$alkyl, —C(O) $C_{1-18}$alkenyl, $C_{0-18}$alkyl-$C_{3-12}$cycloalkyl, $C_{1-18}$haloalkyl, and $C_{1-18}$alkynyl, wherein $Y_2$ and $Y_3$ are independently O, S or N.

29. The compound of claim 1, wherein R3 is selected from the group consisting of H, halogen, $C_{1-10}$alkyl, $C_{1-10}$alkylamino $C_{0-10}$alkyl, $C_{1-10}$hydroxyalkyl, $C_{1-10}$alkylether, $C_{1-10}$alkylthioether, $C_{1-10}$alkyl-$Y_2C(O)Y_3$—$C_{0-10}$alkyl, $C_{1-10}$alkyl-$C(O)Y_3$—$C_{0-10}$alkyl, $C_{1-10}$alkyl-$Y_2C(O)$-$C_{0-10}$alkyl, $C_{5-12}$aryl, $C_{5-12}$aryl$C_{0-10}$alkyl-$Y_2C(O)Y_3$—$C_{0-10}$alkyl, $C_{1-10}$alkyl$C_{5-12}$aryl, $C_{5-12}$aryl$C_{1-18}$alkyl, —C(O) $C_{1-10}$alkenyl, $C_{0-10}$alkyl-$C_{3-12}$cycloalkyl, $C_{1-18}$haloalkyl, and $C_{1-10}$alkynyl, wherein $Y_2$ and $Y_3$ are independently O, S or N, wherein $Y_2$ and $Y_3$ are independently O, S or N.

30. The compound of claim 1, wherein R3 is selected from the group consisting of H, halogen, $C_{1-18}$alkyl, $C_{1-18}$alkylamino $C_{0-18}$alkyl, $C_{1-18}$hydroxyalkyl, $C_{1-18}$alkylether, $C_{1-18}$alkyl-$C(O)Y_3$—$C_{0-18}$alkyl, $C_{1-18}$alkyl-$Y_2C$ (O)—$C_{0-18}$alkyl, $C_{5-12}$aryl, $C_{1-18}$alkyl$C_{5-12}$aryl, $C_{5-12}$aryl$C_{1-18}$alkyl, —$C(O)C_{1-18}$alkenyl, $C_{0-18}$alkyl-$C_{3-12}$cycloalkyl, and $C_{1-18}$haloalkyl, wherein $Y_2$ and $Y_3$ are independently O, S or N.

31. The compound of claim 1, wherein R3 is selected from the group consisting of H, $C_{1-18}$alkyl, $C_{1-18}$alkylamino $C_{0-18}$alkyl, $C_{1-18}$hydroxyalkyl, $C_{1-18}$alkylether, $C_{5-12}$aryl, $C_{1-18}$alkyl$C_{5-12}$aryl, and $C_{5-12}$aryl$C_{1-18}$alkyl.

32. The compound of claim 1, wherein R3 is selected from the group consisting of H, $C_{1-18}$alkyl, $C_{1-18}$alkylamino$C_{0-18}$alkyl, $C_{1-18}$hydroxyalkyl, and $C_{1-18}$alkylether.

33. The compound of claim 1, wherein R3 is $C_{1-18}$alkyl.

34. The compound of claim 1, wherein R3 is selected from the group consisting of $C_{1-18}$alkyl-$Y_2C(O)Y_3$—$C_{0-18}$alkyl, $C_{1-18}$alkyl-$C(O)Y_3$—$C_{0-18}$alkyl, $C_{1-18}$alkyl-$Y_2C(O)$ $C_{0-18}$alkyl, $C_{5-12}$aryl $C_{0-18}$alkyl-$Y_2C(O)Y_3$—$C_{0-18}$alkyl, wherein $Y_2$ and $Y_3$ are independently O, S or N.

35. The compound of claim 1, wherein $Y_1$ is —NH— and R3 is $C_{1-18}$alkyl.

36. The compound of claim 1, wherein $Y_1$ is —O— and R3 is $C_{1-18}$alkyl.

37. The compound of claim 1, wherein R3 is H.

38. The compound of claim 1, wherein R3 is selected from the group consisting of $C_{5-12}$aryl, $C_{1-18}$alkyl$C_{5-12}$aryl, and $C_{5-12}$aryl $C_{1-18}$alkyl.

* * * * *